US007662573B2

(12) United States Patent
Ling et al.

(10) Patent No.: US 7,662,573 B2
(45) Date of Patent: Feb. 16, 2010

(54) METHODS FOR EVALUATING OSTEOARTHRITIS RISK

(75) Inventors: Shari M. Ling, Ellicott City, MD (US); Lorah Perlee, Wilton, CT (US); Velizar T. Tchernev, Sofia (BG); Serguei Lejnine, Mercer Island, WA (US); Dhavalkumar D. Patel, Chapel Hill, NC (US); Luigi Ferrucci, Baltimore, MD (US); Ming Zhan, Germantown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 274 days.

(21) Appl. No.: 11/573,711

(22) PCT Filed: Aug. 12, 2005

(86) PCT No.: PCT/US2005/028871

§ 371 (c)(1),
(2), (4) Date: Feb. 14, 2007

(87) PCT Pub. No.: WO2006/023412

PCT Pub. Date: Mar. 2, 2006

(65) Prior Publication Data

US 2007/0225206 A1    Sep. 27, 2007

Related U.S. Application Data

(60) Provisional application No. 60/602,334, filed on Aug. 18, 2004.

(51) Int. Cl.
*G01N 33/53* (2006.01)
*C07K 14/435* (2006.01)
*C12P 19/34* (2006.01)
*C12Q 1/68* (2006.01)

(52) U.S. Cl. .................. 435/7.1; 435/7.2; 435/91.1; 435/91.2; 435/183; 435/6; 530/350; 530/351

(58) Field of Classification Search .................. None
See application file for complete search history.

(56) References Cited

U.S. PATENT DOCUMENTS 6,902,887 B1    6/2005    Berka et al.
2004/0209307 A1*  10/2004    Valkirs et al. .......... 435/7.1

FOREIGN PATENT DOCUMENTS

EP         1 477 571 A1    11/2004
WO    WO 2004/024892 A2    3/2004

OTHER PUBLICATIONS

Singh et al. Proceedings of the New Zealand Society of Animal Production. 2004. 64: 8-10.*
Liu et al. Clinical Immunology. 2004. 112: 225-230.*
Coleman, R.A. Drug Discovery Today. 2003. 8: 233-235.*
Saetre et al. Molecular Brain Research. 2004. 126: 198-206.*
Haynes et al. Electrophoresis. 1998. 19: 1862-1871.*
Gokmen-Polar et al. Cancer Research. 2001. 61: 1375-1381.*
Geisler et al. Cell Tissue Research. 1997. 289: 173-183.*
Accession No. 2004-329477, Database WPI Week 200430, Derwent Publications Ltd., London, GB.
Aigner et al., "Functional Genomics of Osteoarthritis," *Pharmacogenomics* 3:635-650 (2002).
Garnero et al., "Biomarkers in Osteoarthritis," *Curr. Opin. Rheumatol.* 15:641-646 (2003).
Huang et al., "Simultaneous Detection of Multiple Cytokines from Conditioned Media and Patient's Sera by an Antibody-Based Protein Array System," *Anal. Biochem.* 294:55-62 (2001).
Kingsmore and Patel, "Multiplexed Protein Profiling on Antibody-Based Microarrays by Rolling Circle Amplification," *Curr. Opin. Biotechnol.* 14:74-81 (2003).
Kurhijärvi et al., "Circulating Form of Human Vascular Adhesion Protein-1 (VAP-1): Increased Serum Levels in Inflammatory Liver Diseases," *J. Immunol.* 161:1549-1557 (1998).
Lohmander et al., "Metalloproteinases, Tissue Inhibitor, and Proteoglycan Fragments in Knee Synovial Fluid in Human Osteoarthritis," *Arthritis Rheum.* 36:181-189 (1993).
Naito et al., "Measurement of Matrix Metalloproteinases (MMPs) and Tissue Inhibitor of Metalloproteinases-1 (TIMP-1) in Patients with Knee Osteoarthritis: Comparison with Generalized Osteoarthritis," *Rheumatol.* 38:510-515 (1999).
Otterness et al., "An Analysis of 14 Molecular Markers for Monitoring Osteoarthritis: Segregation of the Markers into Clusters and Distinguishing Osteoarthritis at Baseline," *Osteoarthritis and Cartilage* 8:180-185 (2000).
Otterness et al., "An Analysis of 14 Molecular Markers for Monitoring Osteoarthritis. Relationship of the Markers to Clinical End-Points," *Osteoarthritis and Cartilage* 9:224-231 (2001).
Perlee et al., "Development and Standardization of Multiplexed Antibody Microarrays for Use in Quantitative Proteomics," *Proteome Science* 2:9 (2004).
Schweitzer et al., "Multiplexed Protein Profiling on Microarrays by Rolling-Circle Amplification," *Nature Biotechol.* 20:359-365 (2002).
Shah et al., "A Role for IL-15 in Rheumatoid Arthritis?," *Nature Med.* 4:643 (1998).

(Continued)

*Primary Examiner*—Carla Myers
(74) *Attorney, Agent, or Firm*—Klarquist Sparkman, LLP

(57) ABSTRACT

Methods are provided for evaluating osteoarthritis (OA), for example for diagnosing OA, to confirm a diagnosis of OA, to assess or prognose progression of OA, determining the severity of a subject who has OA, and determining a subject's risk of developing OA in the future, as are arrays and kits that can be used to practice the methods. In particular examples, the method includes determining an amount of activity (such as an amount of protein present or an amount of expression) of OA risk-related molecules, such as soluble vascular adhesion protein 1 (sVAP-1) or interleukin-15 (IL-15). Also provided are methods of identifying one or more compounds that alter the activity of an OA-related molecule, thereby identifying potential anti-osteoarthritis drugs.

25 Claims, 8 Drawing Sheets

OTHER PUBLICATIONS

Sharif et al., "Increased Serum C Reactive Protein May Reflect Events that Precede Radiographic Progression in Osteoarthritis of the Knee," *Ann. Rheum. Dis.* 59:71-74 (2000).

Spector et al., "Low-Level Increases in Serum C-Reactive Protein are Present in Early Osteoarthritis of the Knee and Predict Progressive Disease," *Arthritis Rheum.* 40:723-727 (1997).

Thurkow et al., "Increased Expression of IL-15 in the Synovium of Patients with Rheumatoid Arthritis Compared with Patients with Yersinia-Induced Arthritis and Osteoarthritis," *J. Pathol.* 181:444-450 (1997).

Yang et al., "Detection and Significance of Plasminogen Activator Inhibitor in Synovial Tissue, Synovial Fluid and Plasma from Patients with Rheumatoid Arthritis," *Zhonghua Nei Ke Za Zhi.* 39:690-693 (Abstract only).

Ling et al., "Serum Protein Signatures Detect Early Radiographic Osteoarthritis," *Osteoarthritis Cartilage* 17:43-48, 2009.

Belcher et al., "Plasminogen Activators and Their Inhibitors in Synovial Fluids from Normal, Osteoarthritis, and Rheumatoid Arthritis Knees," *Ann. Rhem. Dis.* 55:230-236 (1996).

Harada et al., "Production of Interleukin-7 and Interleukin-15 by Fibroblast-Like Synoviocytes from Patients with Rheumatoid Arthritis," *Arthritis. Rheum.* 42:1508-1516 (1999).

Klimiuk et al., "Serum Cytokines in Different Histological Variants of Rheumatoid Arthritis," *J. Rheumatol.* 28:1211-1217 (2001).

Ohta et al., "Expression of Matrix Metalloproteinase 7 (Matrilysin) in Human Osteoarthritic Cartilage," *Lab. Invest.* 78:79-87 (1998).

Oleksyszyn and Augustine, "Plasminogen Modulation of IL-1 Stiumulated Degradation in Bovine and Human Articular Cartilage Explants. The Role of the Endogenous Inhibitors: PAI-1, $\alpha_2$-Antiplasmin, $\alpha_1$-PI, $\alpha_2$-Macroglobulin and TIMP," *Inflamm. Res.* 45:464-472 (1996).

Ziolkowska et al., "High Levels of IL-17 in Rheumatoid Arthritis Patients: IL-15 Triggers in Vitro IL-17 Production Via Cyclosporin A-Sensitive Mechanism," *J. Immunol.* 164:2832-2838 (2000).

\* cited by examiner

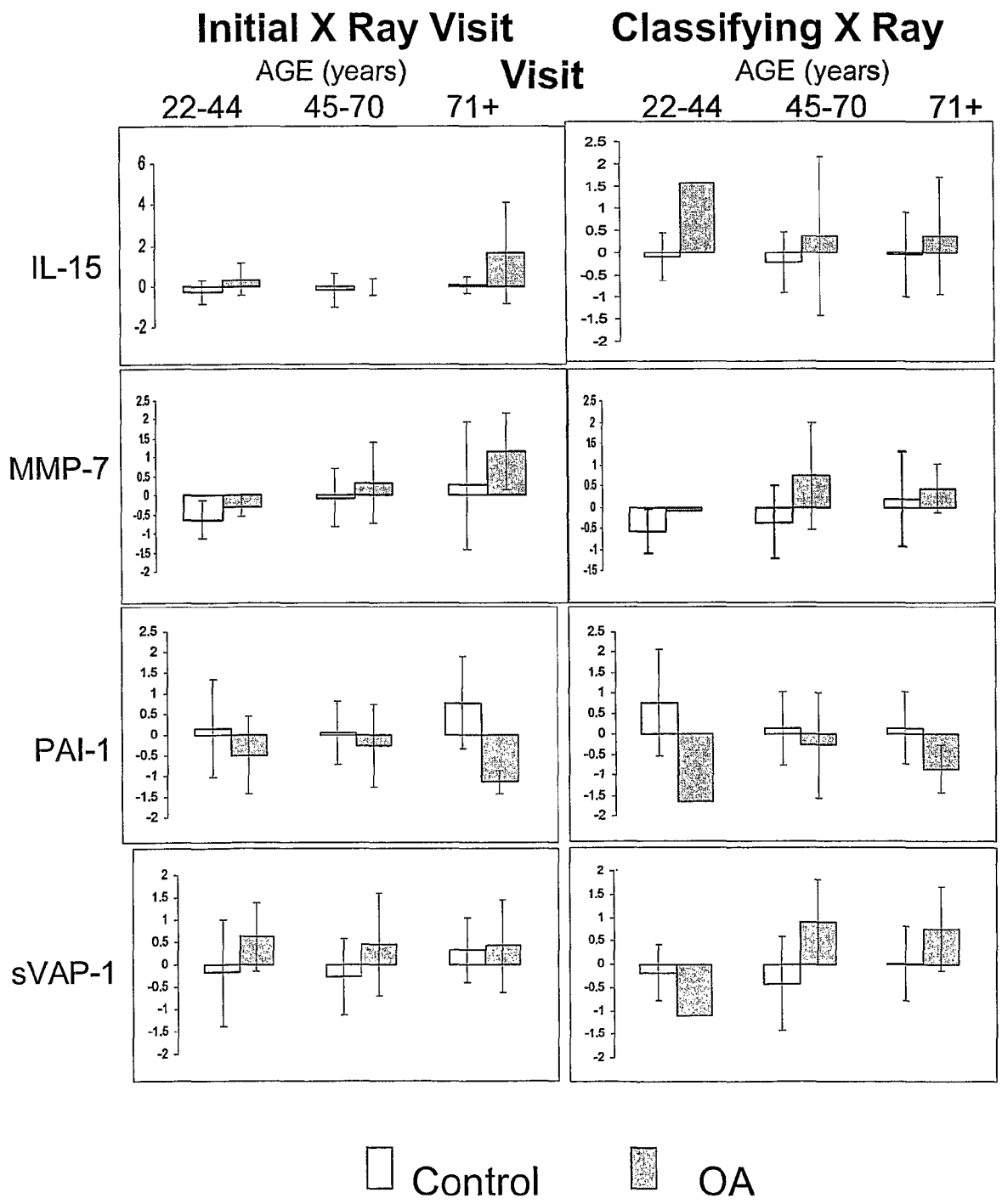
FIGS. 6A-G

METHODS FOR EVALUATING OSTEOARTHRITIS RISK

CROSS REFERENCE TO RELATED APPLICATIONS

This is the U.S. National Stage of International Application No. PCT/US2005/028871, filed Aug. 12, 2005, which was published in English under PCT Article 21(2), which in turn claims the benefit of U.S. Provisional Application No. 60/602,334 filed Aug. 18, 2004, herein incorporated by reference in its entirety.

FIELD

The disclosure relates to methods of evaluating osteoarthritis, as well as methods of identifying compounds that alter the activity of an osteoarthritis-related molecule, as well as arrays and kits that can be used to practice the disclosed methods.

BACKGROUND

Osteoarthritis (OA) is a degenerative joint disease characterized by a fragmentation and erosion of the articular cartilage, which becomes soft, frayed and thinned with alteration of the subchondral bone, hypertrophy of the bone, including outgrowths of marginal osteophytes and changes accompanied by pain and stiffness, and finally by loss of function. Osteoarthritis mainly affects the weight bearing joints. When clinically evident, osteoarthritis is a major cause of morbidity and disability, especially for the elderly, due to joint pain, morning stiffness, and limitation of movement and commonly involves the neck, lower back, knees, hips and joints of the fingers (Lawrence et al., *Arthritis Rheum.*, 41:778-99, 1998; Ling et al., *J. Am. Geriatr. Soc.* 46:216-25, 1998). Osteoarthritis can also develop in joints that have suffered injury or trauma in the past, or have been subjected to prolonged heavy use.

Conventional radiography is generally considered the gold standard for the diagnosis and classification of OA, despite its insensitivity to predict clinical symptoms and its insensitivity to detect early disease or subtle changes over time (Lethbridge-Cejku et al., *Arthritis Care Res.* 8:182-83, 1995; Altman et al., *Arthritis Rheum.* 30:1214-25, 1987). The search for biomarkers measured in synovial fluid, serum, or urine that can be used for diagnosis or for predicting the clinical course of the disease has intensified over recent years. Initial studies focused on cartilage precursors, constituents and degradation products (Bruyere et al., *J Rheumatol.* 30:1043-50, 2003; Dragomir et al., *Osteoarthritis Cartilage* 10:687-91, 2002; Lohmander et al., *Arthritis. Rheum.* 42:534-44, 1999; Poole, *Arthritis. Rheum.* 46:2549-52, 2002; Poole et al., *J. Immunol. Meth.* 294:145-53, 2004; Clark et al., *Arthritis. Rheum.* 42:2356-64, 1999; Vilim et al., *Osteoarthritis Cartilage* 10:707-13, 2002). However, identification of other OA markers is needed, because currently available markers only reflect cartilage and bone damage that have already occurred. Therefore, the identification of markers that reflect early events, predisposition to OA, or factors involved in the continued disease process, would be useful for example to identify patients that could benefit from early intervention of OA. In addition, identification of OA biomarkers may permit the identification of novel therapeutic targets.

SUMMARY

New methods are disclosed for evaluating osteoarthritis (OA). The inventors have identified multiple osteoarthritis markers that can be used to analyze OA. Samples from subjects followed longitudinally for many years and whose phenotype is well characterized, were analyzed using a multiplexed antibody-based protein microarray to measure 169 soluble serum proteins. It was observed that knee and hand OA development could be characterized by detectable changes in serum proteins. Markers relevant to the development of OA, as well as markers that were present with established OA, were identified. Therefore, the disclosed OA risk-related markers can be used to determine whether a subject will develop OA in the future, to diagnose or confirm a diagnosis of OA, to assess or prognose progression of OA, to determine the severity of OA, to identify those subjects that will more likely benefit from a particular OA therapy, or combinations thereof.

The disclosed methods allow one to screen many OA risk-related molecules (such as OA-risk related proteins or nucleic acid molecules) simultaneously and serially. In some examples, only a relatively small amount of biological sample (such as a biological liquid, for example blood, serum, or urine) is needed. Changes in the amount of protein were observed for at least 10 proteins, at least 13 proteins, at least 16 proteins, or at least 17 proteins depending on the sensitivity and specificity of the algorithm used, and the parameter analyzed.

In a particular example, subjects who had OA showed increased amounts of interleukin-15 (IL-15), soluble vascular adhesion protein 1 (sVAP-1), metalloproteinase-7 (MMP-7), interleukin 1 alpha (IL-1α), IL-2, macrophage inhibitory protein (MIP)-1α, B-lymphocyte chemokine (BLC), 6-chemokine (Ckine), fibroblast growth factor (FGF)-7, granulocyte macrophage colony stimulating factor (GM-CSF), insulin-like growth factor binding protein (IGFBP)-2, neurotrophin-4 (NT4), ICAM-3, vascular endothelial (VE)-cadherin, and tissue inhibitors of metalloproteinases 1 (TIMP-1), and decreased amounts of plasminogen activating inhibitor-1 (PAI-1). In another particular example, subjects who had OA showed increased amounts of macrophage inflammatory protein 1β (MIP-1β), urokinase-type plasminogen activator receptor (UPAR), vascular cell adhesion molecule-1 (VCAM-1), IL-2, IGFBP-4, ICAM-3, monokine induced by interferon γ (MIG), MMP-7, myeloid progenitor inhibitory factor 1 (MPIF-1), TGFβ receptor III (TGF-β RIII) (and in some examples also 6-Ckine), and decreased amounts of macrophage inflammatory protein 1δ (MIP-1δ), eotaxin 2 (Eot2), and thymus and activation regulated chemokine (TARC).

In a particular example, subjects who did not have OA initially, but developed OA at a later date, showed increased amounts of IL-15, sVAP-1, MMP-7, and decreased amounts of PAI-1, D-dimer 5 (DD5), DD6, Eot2, intercellular adhesion molecule-1 (ICAM-1), MMP-2, and P-selectin at a time prior to developing OA, for example when OA was not detectable by x-ray. In another particular example, subjects who did not have OA initially, but developed OA at a later date, showed increased amounts of MIP-1β, UPAR, VCAM-1, hemofiltrate CC chemokine 1 (HCC1), leptin, MMP-7, brain-derived neurotrophic factor (BDNF), 6-Ckine, TGF-β RIII and ICAM-3, and decreased amounts of macrophage inflammatory protein 1δ (MIP-1δ), epidermal growth factor (EGF), and prolactin.

In one example, the method of evaluating OA risk in a subject includes detecting patterns of increased activity of an OA risk-associated molecule, decreased activity of an OA risk-associated molecule, or both. Such patterns of activity can be detected at the nucleic acid level (such as quantitation of mRNAs associated with protein expression) or the protein level (such as quantitative detection of proteins). Certain methods involve not only detection of patterns of expression, but detection of the magnitude of expression (increased, decreased, or both), wherein such patterns are associated with the subject having OA or risk of developing OA, or is associated with predicted clinical sequelae, such as severity or progression of OA.

The disclosed methods can be performed on a subject suspected of having OA, for example prior to or after radiographic investigation. In another example, the method is performed on a subject known to have OA, for example to monitor progression of OA, to determine the severity of OA, or to confirm a radiologic diagnosis of OA. In another example the disclosed methods are performed as screening of a subject for disease, for example as part of a screen for a disease in a subject who is neither known to have nor be a risk of having OA.

In one example, the method of evaluating OA includes determining whether a subject has changes in the activity of one or more OA risk-associated molecule that comprise, consist essentially of, or consist of, sequences (such as a DNA, RNA or protein sequence) shown in Tables 8 and 10-13, wherein the presence of differential activity in one or more OA risk-related molecules indicates that the subject has an increased OA risk, such as an increased risk of developing OA in the future, or a diagnosis of OA. In particular examples, the method of evaluating OA includes determining whether a subject has changes in the activity of two or more OA risk-associated molecules (such as three or more, four or more, five or more, or six or more) that comprise, consist essentially of, or consist of, sequences shown in Tables 8 and 10-13, wherein the presence of differential activity in at least 2, at least 3, at least 4, at least 5, or at least 6 OA risk-related molecules indicates that the subject has an increased OA risk, such as an increased risk of developing OA in the future, or a diagnosis of OA.

In one example, the one or more, two or more, three or more, or four or more OA risk-associated molecules include interleukin-15 (IL-15) or soluble vascular adhesion protein 1 (sVAP-1), wherein the method includes determining whether there is an upregulation of at least IL-15 or determining whether there is a downregulation of at least sVAP-1. In another example, the at least four OA risk-related molecules further include matrix metalloproteinase-7 (MMP-7) and plasminogen activating inhibitor-1 (PAM-1), and wherein the method further includes determining whether there is an upregulation of at least MMP-7 and PAM-1. In yet another example, the at least four OA risk-related molecules further include macrophage inflammatory protein 1β (MIP-1β), macrophage inflammatory protein 1δ (MIP-1δ), urokinase-type plasminogen activator receptor (UPAR), and vascular cell adhesion molecule-1 (VCAM-1), and wherein the method includes determining whether there is an upregulation of at least MIP-1β, UPAR, and VCAM-1 and a deregulation of at least MIP-1δ. In yet another example, the at least four OA risk-related molecules further include MIP-1β, MIP-1δ, UPAR, VCAM-1, 6-Ckine, ICAM-3 and TGF-β RIII, and wherein the method includes determining whether there is an upregulation of at least MIP-1β, UPAR, VCAM-1, 6-Ckine, ICAM-3 and TGF-β RIII, and a deregulation of at least MIP-1δ.

In one example, the method of evaluating OA risk includes determining whether the subject has an increased risk of developing OA in the future. In one example, such a method includes determining whether there is an upregulation of at least IL-15, sVAP-1 and MMP-7 and determining whether there is a downregulation of at least PAI-1, D-dimer 5 (DD5), DD6, eotaxin 2 (Eot2), intercellular adhesion molecule-1 (ICAM-1), MMP-2, and P-selectin, wherein the presence of downregulation of PAI-1, DD5, DD6, Eot2, ICAM-1, MMP-2, and P-selectin and the presence of upregulation of IL-15, MMP-7 and sVAP-1 indicates that the subject has an increased risk of developing OA in the future. In another example, such a method includes determining whether there is upregulation of at least MIP-1β, UPAR, VCAM-1, 6-Ckine, ICAM-3, BDNF, HCC1, leptin, MMP-7, and TGF-β RIII, and a downregulation of at least MIP-1δ, prolactin, and EGF, and wherein the presence of upregulation of MIP-1β, UPAR, VCAM-1, 6-Ckine, ICAM-3, BDNF, HCC1, leptin, MMP-7, and TGF-β RIII and the downregulation of MIP-1δ, prolactin, and EGF, indicates that the subject is at risk for developing OA in the future. In such examples, the subject may have no radiological evidence of OA, or may have no clinical symptoms of OA.

In one example, the method of evaluating OA risk includes determining whether the subject has OA. In one example, such a method includes further determining whether there is upregulation of at least interleukin 1 alpha (IL-1α), IL-2, macrophage inhibitory protein (MIP)-1α, B-lymphocyte chemokine (BLC), 6-chemokine (Ckine), fibroblast growth factor (FGF)-7, granulocyte macrophage colony stimulating factor (GM-CSF), insulin-like growth factor binding protein (IGFBP)-2, neurotrophin-4 (NT4), ICAM-3, vascular endothelial (VE)-cadherin, and tissue inhibitors of metalloproteinases 1 (TIMP-1), wherein the presence of downregulation of PAI-1, and the presence of upregulation of IL-15, MMP-7, sVAP-1, IL-1α, IL-2, MIP-1α, BLC, 6-Ckine, FGF-7, GM-CSF, IGFBP-2, NT4, ICAM-3, VE-cadherin, and TIMP-1, indicates that the subject has OA. In another example, such a method includes further determining whether there is upregulation of at least MMP-1β, UPAR, 6-Ckine, VCAM-1, ICAM-3, TGF-β RIII, IL-2, IGFBP-4, MIG, MMP-7, MPIF-1, and downregulation of at least MIP-1δ, Eot2, and TARC, wherein the presence of upregulation of at least MIP-1β, UPAR, 6-Ckine, VCAM-1, ICAM-3, TGF-β RIII, IL-2, IGFBP-4, MIG, MMP-7, MPIF-1, and the downregulation of at least MIP-1δ, Eot2, and TARC, indicates that the subject has OA.

In one example, the method of evaluating OA risk includes determining progression of OA in a subject. The method can include determining whether there is upregulation of one or more molecules listed in Tables 8 and 10-13, or downregulation of one or more molecules listed in Tables 8 and 10-13. For example, the amount of OA-risk associated molecule activity in samples obtained at two different times can be compared. If the activity of the OA-risk associated molecule at the later time point continues to have differential activity, or has a greater magnitude of differential activity, this indicates that OA is progressing. In contrast, if the activity of the OA-risk associated molecule at the later time point no longer has differential activity, or has a lower magnitude of differential activity, this indicates that OA is not progressing or that the progression is slowing. In another example, the amount of OA-risk associated molecule activity in a sample is compared to a reference value or a control. If the activity of the OA-risk associated molecule in the test sample has a greater magnitude of differential activity than the control or reference value representing no OA, this indicates that OA is progressing. In contrast, if the activity of the OA-risk associated molecule in the test sample has a statistically similar amount of differential activity than the control or reference value representing no OA, this indicates that OA is not progressing or that the progression is slowing.

In particular examples, OA risk-associated molecules comprise, consist essentially of, or consist of, IL-15 or sVAP-1 in combination with one or more of MMP-7, PAI-1, DD5, DD6, Eot2, ICAM-1, MMP-2, P-selectin, IL-1α, IL-2, MIP-1α, BLC, 6-Ckine, FGF-7, GM-CSF, IGFBP-2, NT4, ICAM-3, VE-cadherin, TIMP-1, MIP-1β, MIP-1δ, UPAR, VCAM-1, BDNF, EGF, HCC1, leptin, prolactin, IGFBP-4, MIG, MPIF-1, TARC, and TGF-β RIII, or IL-15 or sVAP-1 in combination with any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 of these molecules. For example, OA-associated molecules can comprise, consist essentially of, or consist of, 2 o more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, or 36 or more of the molecules listed in Tables 8 and 10-13. Any of the identified molecules can be used in combination with such sets or subsets of molecules.

In a particular example, evaluating OA includes detecting differential activity in at least one OA risk-related molecule of the subject, such as any combination of at least one, at least two, at least three, or at least four proteins (or the corresponding nucleic acids) listed in any of Tables 8 and 10-13 that includes IL-15 or sVAP-1, wherein the presence of differential activity of at least one, at least two, at least three, or at least four OA risk-related molecules indicates that the subject has OA or is at risk for developing OA in the future. In particular examples, the at least two, at least three or at least four OA risk-related molecules include IL-15 or sVAP-1 in combination with at least one of MMP-7, PAM-1, DD5, DD6, Eot2, ICAM-1, MMP-2, P-selectin, IL-1α, IL-2, MIP-1α, BLC, 6-Ckine, FGF-7, GM-CSF, IGFBP-2, NT4, ICAM-3, VE-cadherin, TIMP-1, MIP-1β, MIP-1δ, UPAR, VCAM-1, BDNF, EGF, HCC1, leptin, prolactin, IGFBP-4, MIG, MPIF-1, TARC, or TGF-β RIII optionally in combination with determining if the subject has altered activity of any other combination of other OA risk-associated molecules, such as any combination of at least 3 other molecules (for example any combination of at least 4, at least 5, at least 6, at least 7, at least 8, at least 9, at least 10, at least 11 at least 12, at least 13, at least 14, at least 15, at least 16, at least 17, at least 18, at least 19, at least 20, at least 21 at least 22, at least 23, at least 24, at least 25, at least 26, at least 27, at least 28, at least 29, at least 30, at least 31, at least 32, at least 33, or even at least 34 of the OA risk-associated molecules listed in Tables 8 and 10-13.

In a particular example, differential activity is detected by determining if the subject has increased activity of at least one of IL-15, sVAP-1, MMP-7, IL-1α, IL-2, MIP-1α, BLC, 6-Ckine, FGF-7, GM-CSF, IGFBP-2, NT4, ICAM-3, VE-cadherin, TIMP-1, MIP-1β, UPAR, VCAM-1, TGF-β RIII, BDNF, HCC, leptin, IGFBP-4, MIG, and MPIF-1. In another example, differential activity is detected by determining if the subject has decreased activity of at least one of PAI-1, DD5, DD6, Eot2, ICAM-1, MMP-2, P-selectin, MIP-1δ, EoT2, and TARC. For example, differential expression can be detected by determining if the subject has increased amounts of IL-15, sVAP-1, MMP-7, IL-1α, IL-2, MIP-1α, BLC, 6-Ckine, FGF-7, GM-CSF, IGFBP-2, NT4, ICAM-3, VE-cadherin, TIMP-1, MIP-1β, UPAR, VCAM-1, TGF-β RIII, BDNF, HCC, leptin, IGFBP-4, MIG, and MPIF-1, and determining if the subject has decreased amounts of PAI-1, DD5, DD6, Eot2, ICAM-1, MMP-2, P-selectin, MIP-1δ, EoT2, and TARC in a sample obtained from the subject, such as a serum sample.

In one example, the method includes determining if the subject has an increase in activity in IL-15, sVAP-1 and any combination of at least more two of the molecules listed in Tables 10-11, for example an increase in at least 3, at least 4, at least 5, at least 6, at least 7, at least 8, at least 9, at least 10, at least 11, at least 12, at least 13, at least 14, at least 15, or at least 16 of the molecules listed in Tables 10-11. An increase in activity of any combination of four or more of the molecules listed in Tables 10-11 indicates that the subject has OA. Any one of the OA risk-associated molecules in Tables 10-11 can be combined with any other combination of the OA risk-associated molecules in Tables 10-11 to produce a combination or subcombination of OA risk-associated molecules (such as nucleic acids or proteins).

In another example, the method includes determining if the subject has a decrease in activity in PAI-1 in combination with any of at least more two of the molecules listed in Tables 12-13, for example an decrease in at least 3, at least 4, at least 5, at least 6, at least 7, at least 8, at least 9, or at least 10 of the molecules listed in Tables 12-13. A decrease in activity of any combination of four or more of the molecules listed in Tables 12-13 indicates that the subject has an increased risk of developing OA in the future. Any one of the OA risk-associated molecules in Tables 12-13 can be combined with any other combination of the OA risk-associated molecules in Tables 12-13 to produce a combination or subcombination of OA risk-associated molecules (such as nucleic acids or proteins).

In some examples, the amount of OA risk-related molecule activity in the subject is compared to a reference value, such as the amount of activity of the OA risk-related molecule (such as an amount of protein present or an amount of gene expression) expected for a subject who has no OA and no risk of OA, wherein an increase or decrease in activity in any combination of one or more OA risk-related molecules listed in Tables 8 and 10-13 (such as two or more, three or more, or four or more OA risk-related molecules listed in Tables 8 and 10-13) compared to the reference value (such as a value range) indicates that the subject has OA or has a risk of developing OA in the future. In one example, the reference value is a range for activity for each target OA risk-related molecules in subjects of the same gender and in the same age range as the test subject. For example, a statistically significant difference between the test subject value and the reference value, such as a p value ≦0.05, or a magnitude of change of at least 25%, at least 50%, at least 75%, at least 100%, or at least 400%, indicates that the molecule has differentially activity in the test subject.

The disclosed methods can further include administering to a subject a treatment to avoid or reduce injury if the presence of differential activity indicates that the subject has OA or has an increased risk of developing OA. For example, a change in the activity in at least four OA risk-related molecules, such as a combination that includes IL-15 or sVAP1, in combination with at least two, at least three or at least four other molecules listed in Tables 8 and 10-13, indicates that the subject has OA or is at risk for developing OA and may need administration of an appropriate therapy (such as administration of glucosamine or an anti-inflammatory agent). In some examples, the amount of differential activity in the subject is compared to reference value (such as a value range) of activity in a subject who has no OA risk or has no OA, wherein a significant change in the activity in at least four OA risk-related molecules listed in Tables 8 and 10-13, compared to the reference value, indicates that the subject would benefit from therapy to treat or prevent OA.

In particular examples, differential expression is detected following the onset of clinical signs and symptoms that indicate OA. Examples of such signs and symptoms include, but are not limited to: pain in the joint, swelling of the joint, stiffness in the joint, limited motion of the joint, deformity of the joints, cracking or "creaking" (crepitation) of the joints accompanied by pain, and other effects on the joint recognized by those of skill in the art.

In one example, the test sample to be analyzed includes OA risk-related proteins. In particular examples detecting differential activity includes quantitating the amount of at least four OA risk-related proteins present in the sample obtained from the test subject. For example, the method can include measuring a quantity of at least four OA risk-related proteins in the sample, wherein a difference in the quantity of the at least four OA risk-related proteins in the sample relative to a quantity of a reference value for each of the at least four OA risk-related proteins in a subject not having OA risk, is differential activity in those at least four OA risk-related molecules. In some examples, the sample from the subject is applied to an array that permits detection of the proteins, such as an array containing antibodies that can detect at least four different OA risk-associated proteins, such as those listed in Tables 8 and 10-13. In particular examples, rolling circle amplification is used to detect and quantitate proteins from the sample that have specifically bound to antibodies on an array.

In other particular examples, the OA risk-related molecules include isolated OA risk-related nucleic acid molecules, such as mRNA or cDNA molecules. The isolated nucleic acid molecules can be detected and quantitated, for example by contacting the nucleic acid molecules to an array, for example an array that includes oligonucleotide probes capable of hybridizing to at least four OA risk-associated genes, such as those listed in Tables 8 and 10-13.

Also provided herein are arrays that include molecules that permit evaluation of OA. Such arrays in particular examples permit quantitation of OA risk-related nucleic acid or protein sequences present in a sample, such as a sample that includes serum proteins. In one example, the array consists essentially of, or consists of, antibodies that recognize at least four OA-risk related proteins, such as those listed in Table 8 and 10-13. In particular examples, the array consists essentially of, or consists of, antibodies that recognize any combination of at least 4 of the proteins listed in any of Tables 8 and 10-13, for example 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 of the proteins listed in any of Tables 8 and 10-13. In some examples, the array can further include one or more control antibodies. Kits including such arrays are also disclosed.

Also provided in the present disclosure are methods of identifying one or more agents that alter the activity (such as the activity) of an OA risk-related molecule (for example a gene or protein), such as one or more of those listed in Tables 8 and 10-13. Such identified molecules are candidate anti-osteoarthritis drugs.

If desired, multiple test agents and multiple OA risk-related molecules can be screened at the same time. In one example, the method is used to screen the effect of one test agent on multiple OA risk-related molecules simultaneously (such as all of the OA risk-related molecules listed in Table 8, 10, 11, 12, or 13). In another example, the method is used to screen the effect of multiple test agents on one OA risk-related molecule, such as one of the molecules listed in Tables 8 and 10-13 (for example IL-15 or PAI-1). In particular examples, the identified agent alters the activity of an OA risk-related molecule that is upregulated or downregulated prior to developing OA, or after OA has developed. For example, the agent can normalize activity of an OA risk-related molecule that is upregulated or downregulated following development of OA, such as by increasing the activity of an OA risk-related molecule that is down-regulated following OA (such as PAI-1), or decreasing activity of an OA risk-related molecule that is upregulated following OA (such as IL-2). In another example, the agent can normalize activity of an OA risk-related molecule that is upregulated or downregulated prior to development of OA, such as by increasing the activity of an OA risk-related molecule that is down-regulated prior to development of OA (such as Eot2), or decreasing activity of an OA risk-related molecule that is upregulated prior to development of OA (such as IL-15 or sVAP-1). The disclosed methods can be performed in vitro (for example in a cell culture) or in vivo (such as in a mammal).

In one example, the test agent is an agent in pre-clinical or clinical trials or approved by a regulatory agency (such as the Food and Drug Administration, FDA), to treat OA. For example, the method can be used to determine if the agent alters the activity of one or more OA risk-related molecules that modifies response to treatment and can predict the best responders.

In another example, the method is used to identify a particular class of agents, such as those that are effective against inflammation. For example, one or more test agents can be screened using the methods disclosed herein, and differential expression of the disclosed inflammation-related genes (or proteins) measured, such as IL-15. Test agents that alter the activity of one or more disclosed inflammation-related molecules are candidates for treatment of inflammation.

Also provided are methods of treating a mammal who has OA or who has an increased risk of developing OA in the future, wherein the method includes administering the agent identified using the disclosed screening methods to the mammal.

The foregoing and other features of the disclosure will become more apparent from the following detailed description of several embodiments.

BRIEF DESCRIPTION OF THE FIGURES

FIGS. 6A-G are graphs showing the z-scores of four differentially expressed proteins between OA and control samples. Series plots of four proteins (Interleukin-15 [IL-15], matrix metalloproteinase [MMP]-7, plasminogen activating inhibitor [PAI]-1, soluble vascular adhesion protein [s-VAP]-1) whose expressions are significantly different between OA and healthy samples at initial X ray and diagnostic X ray visit time. The X-axis is three age groups and Y-axis represents the protein expression values on the MSI microarray chips and Z score of the corresponding values. At three age groups, raw values and z scores of expression data of the proteins at different visit times were plotted separately and by the total average.

DETAILED DESCRIPTION OF SEVERAL EMBODIMENTS

Abbreviations and Terms

Figure 1:
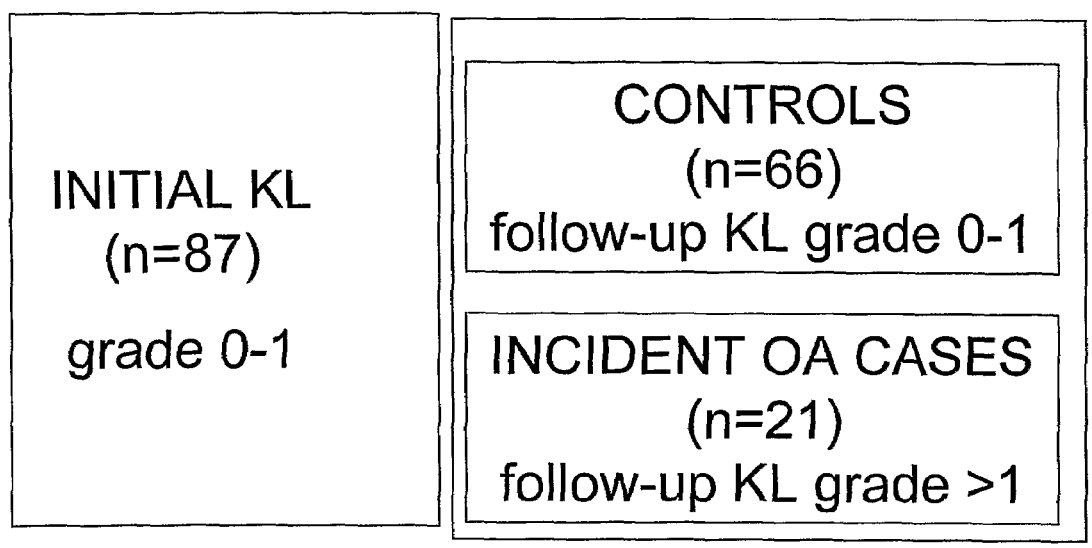
FIG. 1 is a schematic drawing illustrating the study design and sample selection. Fasting serum samples concurrent to the x-ray used to classify participants as "incident knee OA" or "control" were evaluated. A third sample obtained from each "control" obtained approximately 5 years prior to the initial x-ray was also evaluated. Controls also had no radiographic evidence of hand OA.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising an OA risk-related molecule" includes single or plural OA risk-related molecules and is considered equivalent to the phrase "comprising at least one OA risk-related molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

OA: osteoarthritis
RCA: rolling circle amplification

Administration: To provide or give a subject an agent by any effective route. Exemplary routes of administration include, but are not limited to, oral, injection (such as intra-articular, subcutaneous, intramuscular, intradermal, intraperitoneal, and intravenous), sublingual, rectal, transdermal (either directly over the joint or systemically), intranasal, vaginal and inhalation routes.

Amplifying a nucleic acid molecule: To increase the number of copies of a nucleic acid molecule, such as a gene or fragment of a gene, for example a region of an OA-associated gene. The resulting products are called amplification products.

An example of in vitro amplification is the polymerase chain reaction (PCR), in which a biological sample obtained from a subject is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Anti-inflammatory agent: Agents that decrease or prevent inflammation. Anti-inflammatory agents can have one or more analgesic, antipyretic or anti-inflammatory effects. Examples include, but are not limited to, nonsteroidal anti-inflammatory drugs (NSAIDs) that act as non-selective inhibitors of cyclooxygenase (such as aspirin, ibuprofen, naproxen, etodolac, fenoprofen calcium) or those that selectively inhibit cyclooxygenase-2 (COX-2) or COX-3 (such as acetaminophen). Administration of anti-inflammatory agents is one treatment for OA, for example to reduce pain and swelling in the affected joint. Other agents used to treat OA are glucosamine and chondroitin sulfate and their derivatives, caspases, tetracycline derivatives, inhibitors and modulators of matrix metallo proteinases and IL-1 (such as IL-1 converting enzyme inhibitors), inducible nitric oxide synthetase (iNOS), P38, MEK-1/2, and peroxisome-proliferator activated receptors (PPARs).

Array: An arrangement of molecules, such as biological macromolecules (such as proteins or nucleic acid molecules) or biological samples (such as tissue sections), in addressable locations on or in a substrate. A "microarray" is an array that is miniaturized so as to require or be aided by microscopic examination for evaluation or analysis.

The array of molecules ("features") makes it possible to carry out a very large number of analyses on a sample at one time. In certain example arrays, one or more molecules (such as an oligonucleotide probe or antibody) will occur on the array a plurality of times (such as twice), for instance to provide internal controls. The number of addressable locations on the array can vary, for example from at least four, to at least 10, at least 16, at least 20, at least 30, at least 50, at least 75, at least 100, at least 150, at least 200, at least 300, at least 500, at least 1000, at least 10,000, or more.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies that specifically bind to OA risk-associated proteins, such as any combination of at least four of those listed in Tables 8 and 10-13, such as at least 4, at least 5, at least 6, at least 7, at least 8, at least 9, at least 10, at least 14, at least 16, at least 20, at least 25, at least 30, or at least 35 of the proteins listed in any of Tables 8 and 10-13.

An array can include nucleic acid molecules, such as oligonucleotide sequences that are at least 15 nucleotides in length, such as about 15-40 nucleotides in length. In particular examples, an array includes oligonucleotide probes or primers which can be used to detect OA risk-associated sequences, such as any combination of at least four of those listed in Tables 8 and 10-13, such as at least 4, at least 5, at least 6, at least 7, at least 8, at least 9, at least 10, at least 14, at least 16, at least 20, at least 25, at least 30, at least 35, or at least of the sequences listed in any of Tables 8 and 10-13.

Binding or specific binding: An association between two substances or molecules, such as the hybridization of one nucleic acid molecule to another (or itself), the association of an antibody with a peptide, or the association of a protein with another protein or nucleic acid molecule.

An oligonucleotide molecule binds or stably binds to a target nucleic acid molecule (such as an OA risk-related cDNA or mRNA) if a sufficient amount of the oligonucleotide molecule forms base pairs or is hybridized to its target nucleic acid molecule, to permit detection of that binding. Binding can be detected by any procedure known to one skilled in the art, such as by physical or functional properties of the target: oligonucleotide complex. For example, binding can be detected functionally by determining whether binding has an observable effect upon a biosynthetic process such as expression of a gene, DNA replication, transcription, translation, and the like. Physical methods of detecting the binding of complementary strands of nucleic acid molecules, include but are not limited to, s DNase I or chemical footprinting, gel shift and affinity cleavage assays, Northern blotting, dot blotting and light absorption detection procedures. For example, the method can include detecting a signal, such as a detectable label, present on one or both nucleic acid molecules.

An antibody specifically binds to a target protein (such as an OA risk-related protein) if the antibody binds substantially only to the target protein and does not substantially bind to other proteins in a sample containing the target protein. Such specificity can be determined using methods known in the art, such as Western blotting, enzyme-linked immunosorbent assays (ELISA), immunodiffusion assays, in situ immunoassays (for example, using colloidal gold, enzyme or radioisotope labels), agglutination assays, immunoelectrophorectic assays, radioallergosorbent tests (RAST), fluorescent microscopy, flow cytometry, grid, dot or tissue blots; dip-stick assays, or antibody arrays.

Clinical indications of osteoarthritis: One or more signs or symptoms associated with a subject having OA. Particular examples include, but are not limited to: pain (commonly in the hands, hips, knees, or feet, and sometimes in the spine), tenderness and occasional swelling of the joint, stiffness (for example, that lasting less than 1 hour) after long periods of inactivity (such as in the morning after a night's sleep or after sitting for a long time), limited motion of the joint, deformity of the joint (usually in later stages of osteoartritis), cracking or "creaking" (crepitation) of the joints accompanied by pain, and other effects on the joint recognized by those of skill in the art.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair (such as a nucleic acid molecule obtained from a subject) with the bases in a second nucleic acid strand (such as a nucleic acid molecule on an array, for example one that can hybridize to an OA risk-related nucleic acid molecule). Complementarity is described by percentage, that is, the proportion of nucleotides that form base pairs between two strands or within a specific region or domain of two strands. For example, if 10 nucleotides of a 15-nucleotide oligonucleotide form base pairs with a targeted region of a nucleic acid molecule, that oligonucleotide is said to have 66.67% complementarity to the region of nucleic acid targeted.

In the present disclosure, "sufficient complementarity" means that a sufficient number of base pairs exist between an oligonucleotide molecule and a target nucleic acid sequence (such as an OA risk-related sequence, for example any of the sequences listed in Tables 8 and 10-13) to achieve detectable binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. Methods Enzymol. 100:266-285, 1983, and by Sambrook et al. (ed.), Molecular Cloning: A Laboratory Manual, 2nd ed., vol. 1-3, Cold Spring Harbor Laboratory Press, Cold Spring Harbor, N.Y., 1989.

DNA (deoxyribonucleic acid): A long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a peptide.

Differential activity: A difference, such as an increase or decrease, in the expression of a gene (such as an OA-risk related gene) into messenger RNA, the conversion of mRNA to a protein, the biological activity of a protein, the amount of a protein, or combinations thereof. In some examples, the difference is relative to a control or reference value, such as an amount of gene expression or protein present that is expected in a subject who currently does not have OA, and is not at risk for developing OA, or an amount expected in a subject who has OA or a risk of developing OA in the future. Detecting differential activity can include measuring a change in gene expression. In a specific example, detecting differential activity includes determining a relative amount of protein present.

Controls or standards for comparison to a sample, for the determination of differential activity, can include samples believed to be normal (in that they are not altered for the desired characteristic, for example a sample from a subject who has no OA or no risk of developing OA) as well as laboratory values, even though possibly arbitrarily set, keeping in mind that such values can vary from laboratory to laboratory. Laboratory standards and reference values can be set based on a known or determined population value and can be supplied in the format of a graph or table that permits comparison of measured, experimentally determined values.

Downregulated or inactivation: When used in reference to the expression or biological activity of a protein, refers to any process that decreases production of the protein (for example a decrease in transcription of a gene or translation of mRNA), as well as any process that decreases the biological activity of the protein.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability. Examples of processes that decrease the activity of a protein include those that degrade a protein, or interfere with the ability of the protein to interact with one or more targets.

Gene downregulation includes any detectable decrease in the production of a gene product, such as an OA risk-related gene product. In certain examples, production of a gene product decreases by at least 4-fold, for example at least 5-fold or at least 10-fold, as compared to a control (such an amount of gene expression in a normal cell of the same type). In one example, a control is a relative amount of gene expression or protein expression in a biological sample, such as serum, in a subject who has no current OA and no detectable risk of OA.

Protein downregulation or inactivation includes any detectable decrease in a protein, such as an OA risk-related protein. In certain examples, the amount of detectable OA risk-related protein decreases by at least 4-fold, for example at least 5-fold or at least 10-fold, as compared to a control (such an amount of the same protein in a normal cell of the same type). In one example, a control is a relative amount of protein present in a biological sample, such as serum, in a subject who has no current OA and no detectable risk of OA.

Evaluating osteoarthritis: To determine an OA state of a subject, for example, to determine whether a subject is at increased risk for developing OA in the future, determining whether a subject has OA (such as of the knee or hand), to confirm the diagnosis of OA, to determine the severity of OA in a subject, to determine the likely recovery of a subject who has OA, to determine an appropriate therapy for a subject who has OA or is at increased risk for developing OA, to monitor the progression of OA in a subject, or combinations thereof.

Expression: The process by which the coded information of a gene is converted into an operational, non-operational, or structural part of a cell, such as the synthesis of a protein.

Gene expression profile (or fingerprint): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs; in some examples, as few as one or two genes provides a profile, but more genes can be used in a profile, for example at least 3, at least 4, at least 5, at least 6, at least 7, at least 8, at least 8, at least 10, at least 12, at least 13, at least 14, at least 15, at least 16, at least 18, at least 20, at least 25, or at least 30 or more. A gene expression profile (also referred to as a fingerprint) can be linked to a tissue or cell type (such as serum), to a particular stage of normal tissue growth or disease progression (such as OA), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who has no OA). In one example, a gene expression profile in a subject is determined from an array (such as a nucleic acid or protein array).

Hybridization: To form base pairs between complementary regions of two strands of DNA, RNA, or between DNA and RNA, thereby forming a duplex molecule, for example forming a duplex molecule between a nucleic acid molecule obtained from a subject and an OA risk-associated nucleic acid molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

| Very High Stringency (detects sequences that share 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share 80% identity or greater) | |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

-continued

Low Stringency
(detects sequences that share greater than 50% identity)

Hybridization: 6x SSC at RT to 55° C. for 16-20 hours
Wash at least twice: 2x-3x SSC at RT to 55° C. for 20-30 minutes each.

Interleukin (IL)-15: A pleiotropic pro-inflammatory cytokine that participates in the innate and adaptive immune system. IL-15 promotes the activation of T cells, neutrophils and macrophages and induces production of inflammatory cytokines IL-17, IL-6 and tumor necrosis factor. In some examples, IL-15 is essential to the development, homeostasis, function and survival of natural killer (NK) cells.

The term IL-15 includes any IL-15 gene, cDNA, mRNA, or protein from any organism and that is an IL-15 that can activate T cells, neutrophils and macrophages. IL-15 sequences are publicly available. For example, GenBank Accession Nos: Y09908 and CAA71044 disclose human IL-15 nucleic acid and protein sequences, respectively and GenBank Accession Nos: U14332 and AAA75377 disclose mouse IL-15 nucleic acid and protein sequences, respectively.

In one example, a IL-15 sequence includes a full-length wild-type (or native) sequence, as well as IL-15 allelic variants, variants, fragments, homologs or fusion sequences that retain the ability to activate T cells, neutrophils and macrophages. In certain examples, L-15 has at least 80% sequence identity, for example at least 85%, at least 90%, at least 95%, or at least 98% sequence identity to a native IL-15. In other examples, IL-15 has a sequence that hybridizes under very high stringency conditions (for example, see above) to a sequence set forth in GenBank Accession No. Y09908 or U14332, and retains IL-15 activity. In yet other examples, an IL-15 protein has a sequence that can bind to an IL-15 antibody.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. In one example, the biological component is serum which has been isolated from a subject, for example from a blood sample obtained from the subject.

Label: An agent capable of detection, for example by ELISA, spectrophotometry, flow cytometry, or microscopy. For example, a label can be attached to a nucleic acid molecule or protein (indirectly or directly), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Matrix metalloproteinase (MMP)-7: A secreted protease that can act on the extracellular matrix and thereby regulate cell migration and tissue repair. Also referred to in the art as matrilysin. In some examples, MMP-7 proteolytically activates anti-bacterial peptides such as pro-defensins.

The term MMP-7 includes any MMP-7 gene, cDNA, mRNA, or protein from any organism and that is an MMP-7 that can function to regulate cell migration and tissue repair. MMP-7 sequences are publicly available. For example, GenBank Accession Nos: AY795972 and AAV40839 disclose human MMP-7 nucleic acid and protein sequences, respectively and GenBank Accession Nos: NM_010810 and NP_034940 disclose mouse MMP-7 nucleic acid and protein sequences, respectively.

In one example, a MMP-7 sequence includes a full-length wild-type (or native) sequence, as well as MMP-7 allelic variants, variants, fragments, homologs or fusion sequences that retain the ability to regulate cell migration and tissue repair. In certain examples, MMP-7 has at least 80% sequence identity, for example at least 85%, at least 90%, at least 95%, or at least 98% sequence identity to a native MMP-7. In other examples, MMP-7 has a sequence that hybridizes under very high stringency conditions to a sequence set forth in GenBank Accession No. AY795972 or NM_010810, and retains MMP-7 activity. In yet other examples, an MMP-7 protein has a sequence that can bind to an MMP-7 antibody.

Nucleic acid array: An arrangement of nucleic acids (such as DNA or RNA) in assigned locations on a matrix, such as that found in cDNA arrays, or oligonucleotide arrays.

Nucleic acid molecule: A deoxyribonucleotide or ribonucleotide polymer including, without limitation, cDNA, mRNA, genomic DNA, and synthetic (such as chemically synthesized) DNA. The nucleic acid molecule can be double-stranded or single-stranded. Where single-stranded, the nucleic acid molecule can be the sense strand or the antisense strand. In addition, nucleic acid molecule can be circular or linear.

The disclosure includes isolated nucleic acid molecules that include specified lengths of an OA risk-related nucleotide sequence, for example those that encode the proteins listed in Tables 8 and 10-13. Such molecules can include at least 10, at least 15, at least 20, at least 25, at least 30, at least 35, at least 40, at least 45 or at least 50 consecutive nucleotides of these sequences or more, and can be obtained from any region of an OA risk-related nucleic acid molecule.

Nucleotide: Includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example an OA risk-related nucleic acid sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15 or 20 nucleotides.

Oligonucleotide probe: A short sequence of nucleotides, such as at least 8, at least 10, at least 15, at least 20, at least 21, at least 25, or at least 30 nucleotides in length, used to detect the presence of a complementary sequence by molecular hybridization. In particular examples, oligonucleotide probes include a label that permits detection of oligonucleotide probe:target sequence hybridization complexes. For example, an oligonucleotide probe can be used to detect the presence of an OA risk-related nucleic acid molecule.

Osteoarthritis: A disease of the cartilage in joints, which causes progressive breakdown of cartilage until the bones rub against each other. This results in damage to the tissue and underlying bone, causing the painful joint symptoms of osteoarthritis. Osteoarthritis is the most common form of arthritis and commonly affects the joints of the fingers, hips, knees, feet, or spine.

Osteoarthritis risk: The probability that a subject currently has OA, or will develop OA in the future, such OA of the knee or hand.

Osteoarthritis risk-related (or associated) molecule: A molecule whose activity (such as the expression of a cDNA or RNA or an amount of protein) is affected by OA. Such molecules include, for instance, nucleic acid sequences (such as DNA, cDNA, or mRNAs) and proteins. Specific examples include those listed in Tables 8 and 10-13, as well as fragments of the full-length genes, cDNAs, or mRNAs (and proteins encoded thereby) whose activity is altered (such as upregulated or downregulated) in response to the presence of OA or the risk of developing OA.

Examples of OA risk-related molecules whose activity is upregulated in response to OA include IL-15, sVAP-1, and MMP-7. Examples of OA risk-related molecules whose activity is downregulated prior to developing OA include PAI-1, DD5, DD6, Eot2, ICAM-1, MMP-2 and P-selctin.

OA risk-related molecules can be involved in or influenced by OA in many different ways, including causative (in that a change in a OA risk-related molecule leads to development of, or progression to, OA) or resultive (in that development of or progression to OA causes or results in a change in the OA risk-related molecule).

Plasminogen activator inhibitor (PAI)-1: A serine proteinase inhibitor, which is the primary physiological inhibitor of plasminogen activation in vivo, and thus is a primary regulator of the fibrinolytic system. In particular examples, PAI-1 has a functional role in wound healing, atherosclerosis, metabolic disturbances (such as obesity and insulin resistance), tumor angiogenesis, chronic stress, bone remodeling, asthma, rheumatoid arthritis, fibrosis, glomerulonephritis and sepsis.

The term PAI-1 includes any PAI-1 gene, cDNA, mRNA, or protein from any organism and that is a PAI-1 that can reduce or inhibit plasminogen activator. MMP-7 sequences are publicly available. For example, GenBank Accession Nos: X04744 and CAA28444 disclose human PAI-1 nucleic acid and protein sequences, respectively and GenBank Accession Nos: M33960 and AAA39887 disclose mouse PAI-1 nucleic acid and protein sequences, respectively.

In one example, a PAI-1 sequence includes a full-length wild-type (or native) sequence, as well as PAI-1 allelic variants, variants, fragments, homologs or fusion sequences that retain the ability to reduce or inhibit plasminogen activator. In certain examples, PAI-1 has at least 80% sequence identity, for example at least 85%, at least 90%, at least 95%, or at least 98% sequence identity to a native PAI-1. In other examples, PAI-1 has a sequence that hybridizes under very high stringency conditions to a sequence set forth in GenBank Accession No. X04744 or M33960, and retains PAI-1 activity. In yet other examples, a PAI-1 protein has a sequence that can bind to a PAI-1 antibody.

Primer: Short nucleic acid molecule, for instance DNA oligonucleotides 10-100 nucleotides in length, such as 12, 15, 20, 25, 30 or 50 nucleotides or more in length. Primers can be annealed to a complementary target DNA strand by nucleic acid hybridization to form a hybrid between the primer and the target DNA strand (such as an OA risk-related DNA). Primer pairs can be used for amplification of a nucleic acid sequence, such as by PCR or other nucleic acid amplification methods known in the art.

Methods for preparing and using nucleic acid primers are described, for example, in Sambrook et al. (In Molecular Cloning: A Laboratory Manual, CSHL, New York 1989), Ausubel et al. (ed.) (In Current Protocols in Molecular Biology, John Wiley & Sons, New York, 1998), and Innis et al. (PCR Protocols, A Guide to Methods and Applications, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, for example, a primer including 30 consecutive nucleotides of an OA risk-related nucleic acid sequence will anneal to a target sequence, such as another homolog of the designated OA risk-related molecule, with a higher specificity than a corresponding primer of only 15 nucleotides. Thus, in order to obtain greater specificity, primers can be selected that include at least 20, at least 25, at least 30, at least 35, at least 40, at least 45, at least 50 or more consecutive nucleotides of an OA risk-related nucleotide sequence.

Protein: A polymer of amino acids, such as a sequence that includes at least 10 amino acids. The disclosure includes proteins that include full-length or fragments of an OA risk-related protein, for example those proteins listed in Tables 8 and 10-13.

Protein (or peptide) array: An arrangement of proteins (such as antibodies) in assigned locations on a matrix, such as that found in an RCA protein chip. Such an array can be used to identify and quantitate an amount of one or more proteins in a sample, such as an amount of an OA risk-associated protein in a serum sample.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides. In addition, a purified serum sample is one in which the serum has been substantially separated from the other components present in a blood sample.

Rolling circle amplification (RCA): A process (for example an isothermal process) for generating multiple copies of a nucleic acid sequence, such as a sequence attached to an OA risk-associated molecule via one or more antibodies, wherein the accumulation of products proceeds linearly over time. Exemplary methods are provided herein, and are also disclosed in Kingsmore and Patel (*Curr. Opin. Biotech.* 14:74-81, 2003 and Perlee et al. *Proteome Sci.*, 2:9, 2004).

Sample: A biological specimen containing genomic DNA, RNA (including mRNA), protein, or combinations thereof, obtained from a subject. Examples include, but are not limited to, peripheral blood or a subcomponent thereof such as serum or plasma, urine, saliva, tissue biopsy, surgical specimen, synovial fluid, cerebrospinal fluid and autopsy material. In one specific example, a sample is or includes serum.

Soluble vascular adhesion protein (VAP)-1 (sVAP-1): The form of vascular adhesion protein (VAP) found in blood (or fractions thereof such as sera). sVAP is an inflammation-inducible cell surface molecule that attaches lymphocytes and granulocytes to endothelial cells to facilitate transit from the circulation to the tissues.

The term sVAP-1 includes any sVAP-1 gene, cDNA, mRNA, or protein from any organism and that is a sVAP-1 that can attach lymphocytes and granulocytes to endothelial cells. It is likely that sVAP-1 is derived from the transmembrane form of VAP-1 by proteolytic cleaving (for example see Kurkijärvi et al., *J. Immunol.* 161:1549-57, 1998). Deletion of the transmembrane and cytoplasmic domains of VAP-1 would cause only an about 2 kDa decrease in the molecular mass of VAP-1. VAP-1 sequences are publicly available. For example, GenBank Accession Nos: NM_003734 and NP_003725 disclose human VAP-1 nucleic acid and protein sequences, respectively and GenBank Accession Nos: AF078705 and AAC35839 disclose mouse VAP-1 nucleic acid and proteins sequences, respectively.

In one example, an sVAP-1 sequence includes a full-length wild-type (or native) sequence, as well as sVAP-1 allelic variants, variants, fragments, homologs or fusion sequences that retain the ability to attach lymphocytes and granulocytes to endothelial cells. In certain examples, sVAP-1 has at least 80% sequence identity, for example at least 85%, 90%, 95%, or 98% sequence identity to a native sVAP-1. In other examples, sVAP-1 has a sequence that hybridizes under very high stringency conditions to a sequence set forth in GenBank Accession No.: NM_003734 or AF078705, and retains sVAP-1 activity. In yet other examples, a sVAP-1 protein has a sequence that can bind to an sVAP-1 antibody.

Subject: Living multi-cellular vertebrate organisms, a category that includes human and non-human mammals.

Test agent: Any substance, including, but not limited to, a protein (such as an antibody), nucleic acid molecule, organic compound, inorganic compound, or other molecule of interest. In particular examples, a test agent can permeate a cell membrane (alone or in the presence of a carrier).

Therapeutically effective amount: An amount of a pharmaceutical preparation that alone, or together with a pharmaceutically acceptable carrier or one or more additional therapeutic agents, induces the desired response. A therapeutic agent, such as an anti-inflammatory agent (such as nonsteroidal anti-inflammatory drugs, NSAIDs), capsaicin, or glucosamine, is administered in therapeutically effective amounts.

Effective amounts a therapeutic agent can be determined in many different ways, such as assaying for a reduction in OA or improvement of physiological condition of a subject having OA. Effective amounts also can be determined through various in vitro, in vivo or in situ assays.

Therapeutic agents can be administered in a single dose, or in several doses, for example daily, during a course of treatment. However, the effective amount of can be dependent on the source applied, the subject being treated, the severity and type of the condition being treated, and the manner of administration.

In one example, it is an amount sufficient to partially or completely alleviate symptoms of OA within a subject. Treatment can involve only slowing the progression of OA temporarily, but can also include halting or reversing the progression of OA permanently. For example, a pharmaceutical preparation can decrease one or more symptoms of OA, for example decrease a symptom by at least 20%, at least 50%, at least 70%, at least 90%, at least 98%, or even at least 100%, as compared to an amount in the absence of the pharmaceutical preparation.

Treating a disease: "Treatment" refers to a therapeutic intervention that ameliorates a sign or symptom of a disease or pathological condition, such a sign or symptom of OA. Treatment can also induce remission or cure of a condition, such as OA. In particular examples, treatment includes preventing a disease, for example by inhibiting the full development of a disease, such as preventing development of OA. Prevention of a disease does not require a total absence of disease. For example, a decrease of at least 50% can be sufficient.

Under conditions sufficient for: A phrase that is used to describe any environment that permits the desired activity.

In one example, includes culturing cells (such as chondrocytes) under conditions sufficient to mimic OA or induce OA, such as culturing the cells under hypoxic conditions.

In another example, includes administering a test agent to a cell culture or a subject sufficient to allow the desired activity. In particular examples, the desired activity is altering the activity (such as the expression) of an OA risk-related molecule.

Upregulated or activation: When used in reference to the expression or biological activity of a protein, refers to any process that increases production of the protein (for example an increase in transcription of a gene or translation of mRNA), as well as any process that increases the biological activity of the protein.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability. Examples of processes that increase the activity of a protein include those that reduce degradation of the protein, or enhance the ability of the protein to interact with one or more targets.

Gene upregulation includes any detectable increase in the production of a gene product, such as an OA risk-related gene product. In certain examples, production of a gene product increases by at least 4-fold, for example at least 5-fold or at least 10-fold, as compared to a control (such an amount of gene expression in a normal cell of the same type). In one example, a control is a relative amount of gene expression or protein expression in a biological sample, such as serum, in a subject who has no current OA and no detectable risk of OA.

Protein upregulation or activation includes any detectable increase in a protein, such as an OA risk-related protein. In certain examples, the amount of detectable OA risk-related protein increases by at least 4-fold, for example at least 5-fold or at least 10-fold, as compared to a control (such an amount of the same protein in a normal cell of the same type). In one example, a control is a relative amount of protein present in a biological sample, such as serum, in a subject who has no current OA and no detectable risk of OA.

Evaluation of Osteoarthritis Risk

The inventors have identified at least 36 OA risk-associated molecules whose activity (such as nucleic acid or protein expression) is altered (such as upregulated or down-regulated) following OA or prior to development of OA. The number of molecules identified depended on the specificity and sensitivity of the algorithm used. For example, using analysis of covariance, 19 OA risk-related molecules were identified (Table 8 and FIG. 4), and using the mixed model ANOVA and significant analysis of microarray (SAM) methods, 22 OA risk-related molecules were identified (Tables 10 and 12 and FIG. 5). Several OA risk-related molecules not previously associated with OA were identified, such as IL-15 and sVAP-1.

Based on the identification of these OA risk-related molecules, methods were developed to evaluate OA risk in a subject, such as a human other mammal (for example a veterinary subject). Particular examples of evaluating OA risk include determining whether a subject, such as an otherwise healthy subject or a subject suspected or at risk of having OA, has OA, has an increased risk for developing OA in the future (for example a subject who otherwise has no other clinical symptoms associated with OA), assessing the severity of OA in a subject having OA, monitoring the progression of OA in a subject having OA or who has an increased susceptibility to developing OA, identifying those subjects with OA that will respond to a particular anti-OA therapy, or combinations thereof. In some examples, serum obtained from the subject is used to evaluate OA risk. However, one skilled in the art will appreciate that other biological samples can be used.

In particular examples, the disclosed methods are used to confirm previous diagnosis of OA (for example a diagnosis by x-ray or other imaging method). For example, the subject may have been previously diagnosed with OA, for example using an x-ray or other imaging procedure (such as an MRI). In such examples, the disclosed methods can be used to confirm the OA diagnosis or indicate the severity of the diagnosis, or to monitor the progression of OA.

In particular examples, the disclosed methods are performed following the onset of signs and symptoms associated with OA. Examples of such symptoms include, but are not limited to pain, inflammation, stiffness, or limited motion of the affected joint, such as the knee, hand, foot, hip, or spine, and other effects on the joints recognized by those of skill in the art.

In some examples, the method permits earlier detection of OA than if an x-ray or other imaging method was used. Hence the assay described herein can in some examples detect OA even before definitive imaging evidence of the OA is known. For example, the methods disclosed herein may permit detection of OA that is not detectable using x-rays or other imaging methods, as it can be difficult for some imaging modalities (such as x-ray and MRI) to detect early stages of OA. In some examples therefore, the method is performed prior to performing any diagnostic imaging tests (such as those that can find anatomic evidence of OA). In particular examples, the method can determine with a reasonable amount of sensitivity and specificity whether a subject has OA or is at risk for developing OA in the future (such as at least 5 years later, at least 10 years later, or at least 20 years later).

In particular examples, the method further includes administering an appropriate treatment therapy for subjects who have OA or who have an increased risk of developing OA in the future. The results of the assay can be used (alone or in combination with other clinical evidence or imaging) to determine whether anti-OA therapy should be administered to the subject. For example, subjects identified or evaluated as having OA using the disclosed methods can then be provided with appropriate treatments, such as anti-inflammatory agents (for example NSAIDs) that would be appropriate for a subject identified as having OA. In other particular examples, subjects identified or evaluated as having a greater risk of developing OA in the future using the disclosed methods can then be provided with appropriate treatments, such as administration of glucosamine and chondroitin sulfate and their derivatives, instituting weight-management as a preventive strategy for weight-bearing OA, developing strategies to improve work biomechanics to lessen repetitive injury, instituting a program to reduce sports-related injuries and institute recovery programs for young adults at risk for developing OA, for example to prevent or delay the development of OA in the subject.

One particular example of evaluating OA risk in a subject includes determining activity of one or more OA risk related molecules in subject that correlate with age. OA risk-associated molecules found to correlate with age were: brain-derived neurotrophic factor (BDNF), epidermal growth factor (EGF), 6Ckine, intercellular adhesion molecule-3 (ICAM-3), TGFβ receptor III (TGF-β RIII), urokinase-type plasminogen activator receptor (UPAR), vascular cell adhesion molecule-1 (VCAM-1), interleukin 2 (IL-2), monokine induced by interferon γ (MIG), matrix metalloproteinase 7 (MMP7), and myeloid progenitor inhibitory factor 1 (MPIF-1) (also see FIG. 4). For example, ICAM-3 was statistically elevated in subjects 60 years+ having OA; BNDF baseline lower in OA up to age 50, then higher in OA 60+, BNDF follow-up was lower in OA up to age 60 then higher in OA; EGF baseline was lower in OA subjects up to age 50, and confidently higher in subjects having OA at 60+ years; the elevation of IL-2 was lower in OA subjects below age 50 and higher in subjects aged 65 and above; MIG was statistically elevated in subjects age 70+ having OA; MMP7 was higher in subjects having OA for subjects 60 years and below (baseline higher in OA at all ages); MPIF1 was higher in subjects having OA that were 60 years and below (baseline higher in OA at all ages); prolactin baseline was higher in subjects having OA at age 50 and below; and TGF-βRIII higher in subjects having OA at age 60 and older.

Therefore, if the subject is above aged 60 or more, the method can include determining if ICAM-3, BDNF, IL-2, EGF, or TGF-βRIII (or combinations thereof, such as 1, 2, 3, 4, 5 or 6 of these) has increased activity in the subject, wherein the presence of increased activity of at least one of this indicates that the subject has increased OA risk (such as has OA or has increased risk of developing OA). If the subject is above age 70, the method can include determining if ICAM-3, BDNF, IL-2, TGF-βRIII, EGF, or MIG (or combinations thereof, such as 1, 2, 3, 4, 5, or 6 of these) has increased activity in the subject, wherein the presence of increased activity of at least one of these OA risk-associated molecules indicates that the subject has increased OA risk (such as has OA or has increased risk of developing OA). If the subject is aged 60 or below, the method can include determining if MMP-7 or MPIF1, (or combinations thereof, such as 2 of these) has increased activity in the subject or if BDNF has decreased activity in the subject (or combinations thereof), wherein the presence of differential activity of at least one of these OA risk-associated molecules indicates that the subject has increased OA risk (such as has OA or has increased risk of developing OA). If the subject is aged 50 or below, the method can include determining if MMP-7, MPIF1, EGF or BDNF (or combinations thereof, such as 2, 3, or 4 of these) has decreased activity in the subject, or if there is increased prolactin activity, wherein the presence of differential activity of at least one of these OA risk-associated molecules indicates that the subject has increased OA risk (such as has OA or has increased risk of developing OA).

In addition, the disclosure provides biomarkers with differential expression associated with aging or gender.

Detecting Activity of OA-risk Associated Molecules

In particular examples, methods of evaluating OA risk in a subject involves detecting activity of at least four OA risk-related molecules of the subject, wherein the presence of differential activity in at least four OA risk-related molecules indicates that the subject has an increased OA risk. In some examples, detecting differential activity involves quantitatively or qualitatively analyzing an OA risk-related DNA, mRNA, cDNA, protein, or combinations thereof. As used herein, the term "OA risk-related molecule" includes OA risk-related nucleic acid molecules (such as DNA, RNA, for example cDNA or mRNA) and OA risk-related proteins. The term is not limited to those molecules listed in Tables 8 and 10-13 (and molecules that correspond to those listed), but can include other nucleic acid molecules and proteins that are influenced (such as to level, activity, localization) by OA including all of such molecules listed herein. Examples of particular OA risk-related molecules are listed in Tables 8 and 10-13, such as L-15 and VCAM-1.

For example, the method can include determining the activity of interleukin-15 (IL-15) or soluble vascular adhesion protein 1 (sVAP-1) and any combination of at least two other OA risk-related molecules, such as those listed in any of Tables 8 and 10-13, in a sample obtained from or derived from the subject. In particular examples detecting differential activity includes determining whether there is an upregulation of at least IL-15 and determining whether there is a downregulation of at least sVAP-1, wherein the presence of differential activity in at least four OA risk-related molecules indicates that the subject has an increased OA risk. For example, the method can include screening for or determining IL-15 or sVAP-1 activity (or both) in a sample, along with other OA risk-related molecules, such as any combination that includes at least 2 additional molecules listed in Tables 8 and 10-13, for example any combination that includes at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 additional molecules listed in Tables 8 and 10-13.

In one example, the method includes determining the activity of IL-15, sVAP-1 and the other OA risk-related molecules include metalloproteinase-7 (MMP-7) and plasminogen activating inhibitor-1 (PAI-1), wherein the method further includes determining whether there is an upregulation of at least MMP-7 and a downregulation of at least PAI-1. In some examples, upregulation of IL-15, MMP-7 and sVAP-1 and a downregulation of PAI-1, indicates that the subject has an increased OA risk. In a specific example, the method includes determining the activity of IL-15, sVAP-1, MMP-1, PAI-1, as well as at least four other OA risk-related molecules that include D-dimer 5 (DD5), DD6, eotaxin 2 (Eot2), intercellular adhesion molecule-1 (ICAM-1), MMP-2, and P-selectin. In such a method, the method can include determining if there is downregulation of at least DD5, DD6, Eot2, ICAM-1, MMP-2, and P-selectin, wherein the presence of downregulation of 2 or more of PAI-1, DD5, DD6, Eot2, ICAM-1, MMP-2, and P-selectin (such as downregulation of 2, 3, 4, 5, 6, or 7 of these) and the presence of upregulation of IL-15, MMP-7 and sVAP-1 indicates that the subject has an increased risk of developing OA in the future.

In yet another example, the method includes determining the activity of IL-15, sVAP-1 and the other OA risk-related molecules include two or more of macrophage inflammatory protein 1β (MIP-1β), macrophage inflammatory protein 1δ (MIP-1δ), urokinase-type plasminogen activator receptor (UPAR), and vascular cell adhesion molecule-1 (VCAM-1), wherein the method includes also determining whether there is an upregulation of at least MIP-1δ, IL-15, sVAP-1, UPAR, and VCAM-1 and a downregulation of at least MIP-1δ. In some examples, upregulation of 3 or more of IL-15, sVAP-1, MIP-1β, UPAR, and VCAM-1 (such as upregulation of 3, 4 or 5 of these) and a downregulation of MIP-1δ, indicates that the subject has an increased OA risk. In a specific example, the method includes determining the activity of MMP-1β, MIP-1δ, UPAR, and VCAM-1, as well as at least four other OA risk-related molecules that include at least four of (or at least 5 or at least 6 of) brain-derived neurotrophic factor (BDNF), epidermal growth factor (EGF), hemofiltrate CC chemokine 1 (HCC1), leptin, MMP-7, and prolactin. In such a method, the method can include determining if there is upregulation of at least MIP-1β, HCC, leptin, MMP-7, UPAR, VCAM-1, and BDNF, and downregulation of at least MIP-1δ, EGF, and prolactin, wherein the presence of downregulation of 2 or more of MIP-1δ, EGF, and prolactin and the presence of upregulation of 2 or more of MIP-1β, HCC, leptin, MMP-7, UPAR, VCAM-1, and BDNF indicates that the subject has an increased risk of developing OA in the future.

For example, the indication that a subject has an increased risk of developing OA in the future can indicate that the subject has a greater likelihood of developing OA in at least 5 years, at least 10 years, at least 15 years, or at least 20 years. In one example, the subject has no other clinical indications of OA. For example, the subject may have no pain or swelling in the joints.

In another example, the method includes determining the activity of IL-15, sVAP-1 and other OA risk-related molecules that include MMP-7, PAI-1, interleukin 1 alpha (IL-1α), IL-2, macrophage inhibitory protein (MIP)-1α, B-lymphocyte chemokine (BLC), 6-chemokine (Ckine), fibroblast growth factor (FGF)-7, granulocyte macrophage colony stimulating factor (GM-CSF), insulin-like growth factor binding protein (IGFBP)-2, neurotrophin-4 (NT4), ICAM-3, vascular endothelial (VE)-cadherin, and tissue inhibitors of metalloproteinases 1 (TIMP-1), wherein the method includes also determining whether there is an upregulation in at least MMP-7, PAI-1, IL-1α, IL-2, macrophage MIP-1α, BLC, 6-Ckine, FGF-7, granulocyte macrophage colony stimulating factor (GM-CSF), IGFBP-2, NT4, ICAM-3, VE-cadherin, and TIMP-1. In some examples, the presence of downregulation of PAI-1 and upregulation of 3 or more of IL-15, MMP-7, sVAP-1, IL-1α, IL-2, MIP-1α, BLC, 6-Ckine, FGF-7, GM-CSF, IGFBP-2, NT4, ICAM-3, VE-cadherin, and TIMP-1 (such as upregulation of 3, 4, 5, 6, 7, 8, 9, 10, 11, 12, or 13 or these), indicates that the subject has OA.

In another example, the method includes determining the activity of IL-15, sVAP-1 and other OA risk-related molecules that include two or more of (such as at least 3, at least 4, at least 5, at least 6, at least 7, at least 8, or 9 of) IL-2, Eot2, IGFBP-4, ICAM-3, monokine induced by interferon γ (MIG), MMP-7, myeloid progenitor inhibitory factor 1 (MPIF-1), thymus and activation regulated chemokine (TARC), and TGFβ receptor III (TGF-β RIII), wherein the method includes also determining whether there is an upregulation in at least IL-2, IGFBP-4, ICAM-3, MIG, MMP-7, MPIF-1 and TGF-β RIII and a downregulation of at least Eot2 and TARC. In some examples, the presence of downregulation of Eot2 and TARC and upregulation of 2 or more of IL-2, IGFBP-4, ICAM-3, MIG, MMP-7, MPIF-1 and TGF-β RIII (such as upregulation of 2, 3, 4, 5, 6 or 7 of these), indicates that the subject has OA. In a specific example, the method includes determining the activity of MIP-1β, MIP-1δ, UPAR, and VCAM-1, as well as at least one other OA risk-related molecule, such as 1, 2, 3, 4, 5, 6, 7, 8 or 9 of the following: IL-2, Eot2, IGFBP-4, ICAM-3, MIG, MMP-7, MPIF-1, TARC, and TGF-β RIII. In such a method, the method can include determining if there is upregulation of at least MIP-1β, IL-2, IGFBP-4, ICAM-3, MIG, MMP-7, MPIF-1, UPAR, VCAM-1, 6-Ckine, and TGF-β RIII and downregulation of at least MIP-1δ, Eot2 and TARC, wherein the presence of downregulation of 2 or more of MIP-1δ, Eot2, and TARC (such as downregulation of 2 or 3 of these) and the presence of upregulation of 2 or more of MIP-1β, IL-2, IGFBP-4, ICAM-3, MIG, MMP-7, MPIF-1, UPAR, VCAM-1, 6-Ckine, and TGF-β RIII (such as upregulation of 2, 3, 4, 5, 6, 8, 9, 10 or 11 of these) indicates that the subject has OA.

In particular examples, the number of OA risk-related molecules screened is at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, or at least 35 OA risk-related molecules. In other examples, the methods employ screening no more than 70, no more than 60, no more than 50, no more than 40, no more than 35, no more than 30, no more than 29, no more than 28, no more than 27, no more than 26, no more than 25, no more than 24, no more than 23, no more than 22, no more than 21, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, or no more than 4 OA risk-related molecules. Examples of particular OA-risk related molecules are shown in Tables 8 and 10-13.

Differential Activity

Differential activity can be represented by increased or decreased nucleic acid or protein activity of the OA risk-related molecules. For example, differential activity includes, but is not limited to, an increase or decrease in an amount of a nucleic acid molecule or protein, the stability of a nucleic acid molecule or protein, the localization of a nucleic acid molecule or protein, or the biological activity of a nucleic acid molecule or protein. Specific examples include evaluative methods in which changes in activity in at least four OA risk-related nucleic acid molecules or proteins are detected (for example nucleic acids or proteins obtained from a subject thought to have OA or known to have OA), such as changes in activity in any combination of at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or at least 36 OA risk-related molecules, such as those provided in Tables 8 and 10-13. In some examples, differential activity is detected by determining if the subject has increased activity of the desired OA-risk related molecules and determining if the subject has decreased activity of the desired OA-risk related molecules.

In a particular example, differential activity is detected in both OA risk-related molecules that are upregulated and OA risk-related molecules that are downregulated. For example, increased activity of one or more of IL-15, MMP-7, sVAP-1, IL-1α, IL-2, MIP-1α, BLC, 6-Ckine, FGF-7, GM-CSF, IGFBP-2, NT4, TIMP-1, VE-cadherin, MIP-1β, UPAR, VCAM-1, IGFBP-4, ICAM-3, MIG, MPIF-1, and TGF-β RIII, and decreased activity of one or more of PAI-1, MIP-1δ, Eot2, and TARC, wherein at least 4 of the OA risk-related molecules have differential activity in the subject, indicates that the subject has OA, has severe OA, or combinations thereof. In another example, increased activity of one or more of IL-15, MMP-7, sVAP-1, MIP-1β, UPAR, VCAM-1, HCC, leptin, and BDNF, and decreased activity of one or more of MIP-1δ, PAI-1, DD5, DD6, EoT2, ICAM-1, MMP-2, P-selectin, EGF and prolactin, wherein at least 4 of the OA risk-related molecules have differential activity in the subject, indicates that the subject has increased risk of developing OA in the future, has severe OA, or combinations thereof.

Detecting upregulation or downregulation can include a magnitude of change of at least 25%, at least 50%, at least 75%, or even at least 100% or at least 200% for upregulation, such as a magnitude of change of an increase of at least 25% for IL-15, at least 25% for MMP-7, at least 25% for sVAP-1, at least 25% for IL-1α, at least 25% for IL-2, at least 25% for MIP-1α, at least 25% for BLC, at least 25% for 6-Ckine, at least 25% for FGF-7, at least 25% for GM-CSF, at least 25% for IGFBP-2, at least 25% for NT4, at least 25% for ICAM-3, at least 25% for TIMP-1, at least 25% for VE-cadherin, at least 25% for MIP-1β, at least 25% for UPAR, at least 25% for VCAM-1, at least 25% for IGFBP-4, at least 25% for ICAM-3, at least 25% for MIG, at least 25% for MPIF-1, at least 25% for TGF-β RIII, at least 25% for HCC, at least 25% for leptin, at least 25% for 6-Ckine, and at least 25% for BDNF, or such as a magnitude of change of a decrease of at least 25% for PAI-1, at least 25% for MIP-1δ, at least 25% for Eot2, at least 25% for TARC, at least 25% for EGF, at least 25% for prolactin, at least 25% for DD5, at least 25% for DD6, at least 25% for ICAM-1, at least 25% for MMP-2 and at least 25% for P-selectin. Alternatively, upregulation and downregulation are by a magnitude of change (for example relative to a control) of at least 4-fold, such as at least 5-fold, at least 6-fold, or at least 10-fold.

Detecting Protein Activity

The detected OA risk-related molecules in some examples are OA risk-related proteins. For example, the method of detecting differential activity can include quantitating an amount of the OA risk-related proteins. Although some OA risk-related proteins may be informative of OA risk when considered in isolation, more typically activity of a plurality of OA risk-related proteins are tested and considered in determining a diagnosis or prognosis. For example, expression of at least four OA risk-associated proteins can be considered, such as 4, 5, 6, or 7 proteins. In some examples, more OA risk-associated proteins are analyzed, but only a subset may be sufficient to provide a diagnosis or prognosis. In some examples, for example to gain increased statistical power, even more OA risk-associated proteins, such as 8, 9, 10, 11, 12, 13, 14, 15, 16, 17, 18, 19, 20, 21, 22, 23, 24, 25, 26, 27, 28, 29, 30, 31, 32, 33, 34, 35, or 36 proteins are tested. In particular examples, both OA risk-associated proteins that are elevated in activity and OA risk-associated proteins that are decreased in activity are detected in the same assay.

OA risk-associated proteins can be detected in a test sample by any means known in the art. For example, any immunological detection method known in the art can be used, such as in vitro hybridization (which can include quantified hybridization) such as hybridization to a protein-specific binding agent for example an antibody, solid phase immunoassays (for example antibody probe arrays, such as RCA protein chips), quantitative spectroscopic methods (for example mass spectrometry, such as surface-enhanced laser desorption/ionization (SELDI)-based mass spectrometry), or combinations thereof. Methods that apply nucleic acid signal amplification to the detection of non-nucleic acid analytes (such as rolling circle amplification, RCA) can be employed for detecting, determining, and quantitating specific protein analytes in samples (for example see U.S. Pat. No. 6,531,283, incorporated herein by reference). However, one skilled in the art will recognize that other methods known in the art can be used.

A variety of solid phase substrates can be used to quantitate or determine the concentration of a protein, such as an OA risk-associated protein. The choice of substrate can be readily made by the routineer, based on convenience, cost, skill, or other considerations. Useful substrates include without limitation: beads, bottles, surfaces, substrates, fibers, wires, framed structures, tubes, filaments, plates, sheets, and wells. Exemplary substrates are made from: polystyrene, polypropylene, polycarbonate, glass, plastic, metal, alloy, cellulose, cellulose derivatives, nylon, coated surfaces, acrylamide or its derivatives and polymers thereof, agarose, or latex, or combinations thereof. This list is illustrative rather than exhaustive.

Another method of protein detection and measurement uses an antibody coupled to beads or to a well in a microwell plate that is quantitated by immunoassay. In this assay format, a single protein can be detected in each assay. The assays can be repeated with antibodies to many proteins to arrive at essentially the same results as can be achieved using the methods of this disclosure. Bead assays can be multiplexed by employing a plurality of beads, each of which is uniquely labeled in some manner. For example each type of bead can contain a pre-selected amount of a fluorophore. Types of beads can be distinguished by determining the amount of fluorescence (or wavelength) emitted by a bead. Such fluorescently labeled beads are commercially available from Luminex Corporation (Austin, Tex.) and permit up to 100 protein measurements simultaneously.

Protein analytes can alternatively be measured by enzyme-linked immunosorbent assay (ELISA), which permits a single protein measurement per microwell, and can be scaled up to 384 or more measurements per plate. Non-immunological assays can also be used. Enzyme activity-based assays can achieve a high degree of sensitivity and can be used. Specific binding protein assays can be used where a protein is a member of a specific binding pair that has a high binding affinity (low dissociation constant). The other member of the specific binding pair may be a protein or a non-protein, such as a nucleic acid sequence which is specifically bound by a protein.

In one example, the method of detecting differential activity of OA risk-related proteins includes measuring a quantity of at least four OA risk-related proteins in a sample obtained from the subject, wherein a difference in the quantity of the at least four OA risk-related proteins in the sample relative to a quantity of a reference value for each of the at least four OA risk-related proteins (such as a value or range of values representing an amount for a subject not having OA risk), is differential activity in those at least four vascular risk-related molecules. For example, statistical differences can be determined using statistical methods well known in the art (such as the Student's t-test). Determination of accuracy and sensitivity is well within the skill of those in the art. In one example, a statistically significant difference with a p value $\leq 0.05$ between the quantity in the sample obtained from the test subject and the reference (or control) value indicates that there is differential activity in the OA-risk related protein. In another example, an at least four-fold difference between the quantity in the sample obtained from the subject and the reference value indicates that there is differential activity in the OA-risk related protein.

In one example, proteins in the test sample are incubated in the presence of antibodies that recognize OA-risk associated proteins, under conditions sufficient for the proteins to specifically bind to the antibodies. For example, the method can include incubating the protein-containing sample with the antibodies (such as antibodies on an array substrate) for a time sufficient to allow specific binding between the proteins and antibodies, thereby forming protein:antibody complexes and subsequently analyzing the protein:antibody complexes to determine if activity of the proteins was altered. In one example, analyzing the protein:antibody complexes includes determining an amount of protein:antibody complexes present in the sample, and comparing the amount to a reference value for each OA risk-related protein tested (such as an amount or range of amounts of protein for a subject who has no OA risk). For example, the protein:antibody complexes can be detected and quantified. The presence of differential activity of at least four OA risk-related proteins can indicate that the subject has increased OA risk.

Multiple proteins can be analyzed, for example, by sandwich immunoassays on microarrays to which primary antibodies specific to the various proteins have been immobilized, for example on an array. For example, the test sample containing proteins are incubated with an array that includes antibodies that recognize OA-risk associated proteins. The protein analytes, if present in the sample, are captured on the cognate spots on the array by incubation of the sample with the microarray under conditions favoring specific antigen-antibody interactions. The captured proteins can then be detected, for example by detecting a label present on the protein, or binding another labeled general antibody to the captured proteins, and detecting the label. In some examples, a rolling circle amplification (RCA) primer is associated with the various protein analytes using a secondary antibody that is specific for the protein being detected and which is conjugated to the RCA primer or a hapten. In direct immunoassays, the secondary antibody is conjugated directly to the RCA primer. In indirect immunoassays, the secondary antibody is conjugated to a hapten, such as biotin and then incubated with a detector antibody conjugate or streptavidin conjugated with the RCA primer. Rolling circle replication primed by the primers results in production of a large amount of DNA at the site in the array where the proteins are immobilized. The amplified DNA serves as a readily detectable signal for the proteins. This signal can be detected, and quantitated, and compared to a reference or control value.

Different proteins in the array can be distinguished in several ways. For example, the location of the amplified DNA can indicate the protein involved, if different proteins are immobilized at pre-determined locations in the array. Alternatively, each different protein can be associated with a different rolling circle replication primer that in turn primes rolling circle replication of a different DNA circle. The result is distinctive amplified DNA for each different protein. The different amplified DNAs can be distinguished using any suitable sequence-based nucleic acid detection technique. Comparison of protein analytes found in two or more different samples can be performed using any means known in the art. For example, a first sample can be analyzed in one array and a second sample analyzed in a second array that is a replica of the first array. The intensity of a spot for each protein at the first array can be compared with the intensity of the corresponding spot of the second array. The differences in the intensities of the spot between the first and second array determine if the concentration of the protein is different in the two samples. If differences exist, they are recorded as increased protein activity or decrease protein activity. Alternatively, the same protein from different samples can be associated with different primers which prime replication of different DNA circles to produce different amplified DNAs. In this manner, each of many proteins present in several samples can be quantitated.

OA risk-associated proteins can be analyzed directly or derivatives of the proteins can be analyzed. The derivatives can be forms of the protein which occur in the body, or forms which are produced, either spontaneously or by design, during sample processing. Examples of derivatives include proteolytic degradation products, phosphorylated products, acetylated products, myristoylated products, transaminated products, protein complexed products, and complex dissociated products. All such derivatives are included within the term "OA risk-associated protein."

In some examples, the resulting pattern of OA risk associated proteins in the subject provides an expression profile of the subject for OA risk. Such a profile can be compared to a control profile, such as one for a subject not having OA, and in some examples is of a similar age or age range, the same gender, or combinations thereof.

Detecting Nucleic Acid Activity

The detected OA risk-related molecules in some examples are OA risk-related nucleic acids. For example, the method of detecting differential activity can include quantitating an amount of expression of the OA risk-related nucleic acid molecules. Exemplary nucleic acid molecules include mRNA or cDNA. Although some OA risk-related nucleic acids may be informative of OA risk when considered in isolation, more typically activity of a plurality of OA risk-related nucleic acids are tested and considered in determining a diagnosis or prognosis. For example, expression of at least four OA risk-associated nucleic acids can be considered, such as 4, 5, 6, or 7 nucleic acids. In some examples, more OA risk-associated nucleic acids are analyzed, but only a subset may be sufficient to provide a diagnosis or prognosis. In some examples, for example to gain increased statistical power, even more OA risk-associated nucleic acids, such as 8, 9, 10, 11, 12, 13, 14, 15, 16, 17, 18, 19, 20, 21, 22, 23, 24, 25, 26, 27, 28, 29, 30, 31, 32, 33, 34, 35, or 36 nucleic acids are tested. In particular examples, both OA risk-associated nucleic acids that are elevated in activity and OA risk-associated nucleic acids that are decreased in activity (as an indication of OA risk) are detected in the same assay.

Any method of detecting nucleic acid molecules can be used. For example, the level of gene activity can be quantitated utilizing methods well known in the art, such as Northern-Blots, RNase protection assays, nucleic acid or antibody probe arrays, in vitro nucleic acid amplification (such as RT-PCR or real time PCR,), nucleic acid hybridization (which can include quantified hybridization), dot blot assays, in-situ hybridization, or combinations thereof. However, one skilled in the art will appreciate that other methods can be used.

In one example, nucleic acid molecules are isolated from a sample obtained from the subject, thereby generating isolated nucleic acid molecules. The resulting isolated nucleic acid molecules can be detected, for example by hybridizing with oligonucleotides that can detect OA risk-related molecules. In one example, hybridizing with the oligonucleotides includes incubating the isolated nucleic acid molecules with the oligonucleotides for a time sufficient to allow hybridization between the isolated nucleic acid molecules and oligonucleotides, thereby forming isolated nucleic acid molecule:oligonucleotide complexes. The resulting complexes can be analyzed to determine if activity of the isolated nucleic acid molecules was altered, wherein the presence of differential activity of at least four OA risk-related nucleic acids indicates that the subject has increased OA risk. For example, the amount of nucleic acid hybridization can be determined, for example by detecting and quantifying the complexes, and compared to a reference value for an amount of hybridization for each OA risk-related nucleic acid tested (for example a value or range of values expected in a subject who has no OA risk).

In a particular example, the oligonucleotides that can detect OA risk-related molecules are present on an array substrate. Such oligonucleotides can be complementary to any combination of at least four molecules listed in Tables 8 and 10-13. For example, the nucleic acid molecules obtained from the subject can be applied to an OA risk detection array under suitable hybridization conditions to form a hybridization complex. In particular examples, the oligonucleotides on the array include a label. In another example, the nucleic acid molecules isolated from the subject include a label. In one example, a pre-treatment solution of organic compounds, solutions that include organic compounds, or hot water, can be applied before hybridization (see U.S. Pat. No. 5,985,567, herein incorporated by reference).

Hybridization conditions for a given combination of array and target material can be optimized routinely in an empirical manner close to the $T_m$ of the expected duplexes, thereby maximizing the discriminating power of the method. Identification of the location in the array, such as a cell, in which binding occurs, permits a rapid and accurate identification of sequences associated with OA risk present in the amplified material (see below).

The hybridization conditions are selected to permit discrimination between matched and mismatched oligonucleotides. Hybridization conditions can be chosen to correspond to those known to be suitable in standard procedures for hybridization to filters and then optimized for use with the arrays of the disclosure. For example, conditions suitable for hybridization of one type of target would be adjusted for the use of other targets for the array. In particular, temperature is controlled to substantially eliminate formation of duplexes between sequences other than exactly complementary OA risk-associated sequences. A variety of known hybridization solvents can be employed, the choice being dependent on considerations known to one of skill in the art (see U.S. Pat. No. 5,981,185).

Once the nucleic acid molecules associated with OA risk from the subject have been hybridized with the oligonucleotides present in the OA risk detection array, the presence of the hybridization complex can be analyzed, for example by detecting the complexes, an in some examples includes quantifying the complexes.

Detecting a hybridized complex in an array of oligonucleotide probes has been previously described (see U.S. Pat. No. 5,985,567, herein incorporated by reference). In one example, detection includes detecting one or more labels present on the oligonucleotides, one or more labels present on the nucleic acid molecules obtained from the subject, or both. In particular examples, developing includes applying a buffer.

In one example, the buffer is sodium saline citrate, sodium saline phosphate, tetramethylammonium chloride, sodium saline citrate in ethylenediaminetetra-acetic, sodium saline citrate in sodium dodecyl sulfate, sodium saline phosphate in ethylenediaminetetra-acetic, sodium saline phosphate in sodium dodecyl sulfate, tetramethylammonium chloride in ethylenediaminetetra-acetic, tetramethylammonium chloride in sodium dodecyl sulfate, or combinations thereof. However, other suitable buffer solutions can also be used.

Detection can further include treating the hybridized complex with a conjugating solution to effect conjugation or coupling of the hybridized complex with the detection label, and treating the conjugated, hybridized complex with a detection reagent. In one example, the conjugating solution includes streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one example, the detection reagent includes enzyme-labeled fluorescence reagents or calorimetric reagents. In one specific non-limiting example, the detection reagent is enzyme-labeled fluorescence reagent (ELF) from Molecular Probes, Inc. (Eugene, Oreg.). The hybridized complex can then be placed on a detection device, such as an ultraviolet (UV) transilluminator (manufactured by UVP, Inc. of Upland, Calif.). The signal is developed and the increased signal intensity can be recorded with a recording device, such as a charge coupled device (CCD) camera (manufactured by Photometrics, Inc. of Tucson, Ariz.). In particular examples, these steps are not performed when fluorophores or radiolabels are used.

Labeling OA-risk Associated Molecules

Methods for labeling nucleic acid molecules and proteins so that they can be detected are well known. Examples of such labels include non-radiolabels and radiolabels. Non-radiolabels include, but are not limited to, enzymes, chemiluminescent compounds, fluorophores, metal complexes, haptens, colorimetric agents, dyes, or combinations thereof. Radiolabels include, but are not limited to, $^{125}$I and $^{35}$S. Radioactive and fluorescent labeling methods, as well as other methods known in the art, are suitable for use with the present disclosure. In one example, the primers used to amplify a nucleic acid molecule are labeled (such as with biotin, a radiolabel, or a fluorophore). In another example, the amplified nucleic acid samples are end-labeled to form labeled amplified material. For example, amplified nucleic acid molecules can be labeled by including labeled nucleotides in the amplification reactions. In another example, nucleic acid molecules obtained from a subject are labeled, and applied to an array containing oligonucleotides. In a particular example, proteins obtained from a subject are labeled and subsequently analyzed, for example by applying them to an array.

Comparison to Controls

Determining the level of activity can involve measuring an amount of the OA risk-related molecules in a sample derived from the subject, such as a serum sample.

Such an amount can be compared to that present in a control sample (such as a sample derived from a subject who has no OA or no predisposition to developing OA, or a standard OA risk-related molecule level in analogous samples from one or more subjects not having OA or not having a predisposition developing OA), wherein a difference (such as an increase or a decrease reflecting an upregulation or downregulation, respectively) in the level of any combination of at least 4 OA risk-related molecules listed in Tables 8 and 10-13, such as any combination of at least 4 OA risk-related molecules listed in Tables 8 and 10-13, in the subject relative to the control sample is diagnostic or prognostic for OA.

In another example, the amount can be compared to that present in a control sample (such as a sample derived from a subject who has OA or a predisposition to developing OA, or a standard OA risk-related molecule level in analogous samples from one or more subjects having OA or having a predisposition developing OA), wherein a similar amount present (such as less than a four-fold difference) in the level of any combination of at least 4 OA risk-related molecules listed in Tables 8 and 10-13, such as any combination of at least 4 OA risk-related molecules listed in Tables 8 and 10-13, in the subject relative to the control sample is diagnostic or prognostic for OA.

In another example, the amount of the OA risk-related molecule is compared to a reference value, such as a range of values or a standard curve, representing an amount of the OA risk related molecule expected in subjects not having OA, not having a predisposition for developing OA, having OA, or having a predisposition for developing OA.

In particular examples, the control, standard, or reference value is for a subject of the same gender as the test subject, for a subject of the same age range as the test subject (such as within 5 years of age of the test subject, for example within 10 years, 12 years, or within 15 years), or combinations thereof.

Clinical Specimens

Appropriate specimens for use with the current disclosure in determining OA risk include any conventional clinical samples, for instance blood or blood-fractions (such as serum or plasma). Other exemplary samples include synovial fluid, cerebrospinal fluid, urine, sputum, tears, saliva, stool, biopsy, and cheek smear. Techniques for acquisition of such samples are well known in the art (for example see Schluger et al. *J. Exp. Med.* 176:1327-33, 1992, for the collection of serum samples). Serum or other blood fractions can be prepared in the conventional manner. For example, about 200 μL of serum can be used for the extraction of DNA for use in amplification reactions. However, if DNA is not amplified, larger amounts of blood can be collected. For example, if at least 5 μg of mRNA is desired, about 20-30 mls of blood can be collected. Similarly, about 20 μl of serum can be used for RCA microarray analysis.

Once a sample has been obtained, the sample can be used directly, concentrated (for example by centrifugation or filtration), purified, amplified, fractionated, or combinations thereof, for example to improve sensitivity and reduce background. For example, any fractionation, concentration, or purification procedure known in the art can be used, so long as the desired analyte remains in the fraction which is used as a test sample. For example, rapid DNA preparation can be performed using a commercially available kit (such as the InstaGene Matrix, BioRad, Hercules, Calif.; the NucliSens isolation kit, Organon Teknika, Netherlands. In one example, the DNA preparation method yields a nucleotide preparation that is accessible to, and amenable to, nucleic acid amplification. Similarly, RNA can be prepared using a commercially available kit (such as the RNeasy Mini Kit, Qiagen, Valencia, Calif.).

Control samples can be obtained or derived from a healthy subject or from a subject who is ill but who does not have OA. Control samples can be assayed individually or in pools. The data from individual controls can be pooled to provide a range of "normal" values. The data can be obtained at an earlier time. Thus controls need not be run in a side-by-side fashion with test samples. For some purposes, samples from a single individual taken at different times are compared to each other. In such cases there need not be evaluated, but may be, any control or normal sample. Control samples can also be synthetically produced, by mixing known quantities of particular analytes, either in an artificial or a natural body sample.

Arrays for Detecting Differential Activity

In particular examples, methods for detecting a change in activity in the disclosed OA risk-related molecules listed in Tables 8 and 10-13 use the arrays disclosed herein. Arrays can be used to detect the presence of nucleic acids or proteins whose activity is upregulated or downregulated to cause OA or in response to OA, for example using specific oligonucleotide probes or antibody probes. The arrays herein termed "OA risk detection arrays," are used to evaluate OA risk, for example to determine whether a subject has OA, has an increased risk for developing OA in the future, assessing the severity of OA in a subject having OA, monitoring the progression of OA in a subject having OA or who has an increased susceptibility to developing OA, identifying those subjects with OA that will respond to a particular anti-OA therapy, or combinations thereof.

Also provided by the present application are OA risk detection arrays.

Nucleic Acid Arrays

In one example, the array includes nucleic acid oligonucleotide probes that can hybridize to any combination of at least two of the OA risk-related nucleic acid sequences listed in Tables 8 and 10-13, such as any combination of 2-36, 4-36, 4-30, 4-25, 4-20, 4-16, 4-15, or 4-10 of the OA risk-related nucleic acid molecules listed in Tables 8 and 10-13. In another particular example, an OA risk detection array includes oligonucleotides that can specifically hybridize under high stringency conditions to at least four of the OA-risk related nucleic acid molecules listed in Tables 8 and 10-13, In a particular example, the array consists of oligonucleotides that recognize any combination of 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, or 36 of the OA-risk related nucleic acid molecules listed in Tables 8 and 10-13. For example, the array can consist of oligonucleotides that recognize the OA-risk related molecules listed in one of Table 10, 11, 12 or 13. One skilled in the art will appreciate that such arrays can also include oligonucleotides that recognize non-OA risk related nucleic acid molecules as internal controls. Certain of such arrays (as well as the methods described herein) can include OA risk-related molecules that are not listed in Tables 8 and 10-13.

In one example, a set of oligonucleotide probes is attached to the surface of a solid support for use in detection of OA risk-associated sequences, such as those nucleic acid sequences (such as cDNA or mRNA) obtained from the subject. Additionally, if an internal control nucleic acid sequence is used (such as a nucleic acid sequence obtained from a subject who has no OA) an oligonucleotide probe can be included to detect the presence of this control nucleic acid molecule.

The oligonucleotide probes bound to the array can specifically bind sequences obtained from the subject, or amplified from the subject (such as under high stringency conditions). Thus, sequences of use with the method are oligonucleotide probes that recognize OA risk-related sequences, such as gene sequences (or corresponding proteins) listed in Tables 8 and 10-13. Such sequences can be determined by examining the sequences of the different species, and choosing oligonucleotide sequences that specifically anneal to a particular OA risk-related sequence (such as those listed in Tables 8 and 10-13), but not others. One of skill in the art can identify other OA risk-associated oligonucleotide molecules that can be attached to the surface of a solid support for the detection of other OA risk-associated nucleic acid sequences.

The methods and apparatus in accordance with the present disclosure take advantage of the fact that under appropriate conditions oligonucleotides form base-paired duplexes with nucleic acid molecules that have a complementary base sequence. The stability of the duplex is dependent on a number of factors, including the length of the oligonucleotides, the base composition, and the composition of the solution in which hybridization is effected. The effects of base composition on duplex stability can be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target sequences and the oligonucleotides bound to the array, the rate of formation of mismatched duplexes may be substantially reduced.

The length of each oligonucleotide sequence employed in the array can be selected to optimize binding of target OA risk-associated nucleic acid sequences. An optimum length for use with a particular OA risk-associated nucleic acid sequence under specific screening conditions can be determined empirically. Thus, the length for each individual element of the set of oligonucleotide sequences including in the array can be optimized for screening. In one example, oligonucleotide probes are from about 20 to about 35 nucleotides in length or about 25 to about 40 nucleotides in length.

The oligonucleotide probe sequences forming the array can be directly linked to the support. Alternatively, the oligonucleotide probes can be attached to the support by non-OA risk-associated sequences such as oligonucleotides or other molecules that serve as spacers or linkers to the solid support.

Protein Arrays

In particular examples, an array includes protein sequences (or a fragment of such proteins, or antibodies specific to such proteins or protein fragments) that recognize (such as specifically bind to) at least four of the OA-risk related proteins listed in Tables 8 and 10-13, such as any combination of 2-36, 4-36, 4-30, 4-25, 4-20, 4-16, 4-15, or 4-10 of the OA risk-related proteins listed in Tables _. In a particular example, the array consists of antibodies that recognize any combination of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 of the OA-risk related proteins listed in Tables 8 and 10-13. For example, the array can consist of antibodies that recognize the OA-risk related molecules listed in one of Table 10, 11, 12 or 13. One skilled in the art will appreciate that such arrays can also include antibodies that recognize non-OA risk related proteins as internal controls.

The proteins or antibodies forming the array can be directly linked to the support. Alternatively, the proteins or antibodies can be attached to the support by spacers or linkers to the solid support.

Changes in expression of OA risk-related proteins can be detected using, for instance, an OA risk-protein-specific binding agent, which in some instances is labeled with an agent that can be detected. In certain examples, detecting a change in protein expression includes contacting a protein sample obtained from a subject with an OA risk protein-specific binding agent (which can be for example present on an array); and detecting whether the binding agent is bound by the sample and thereby measuring the levels of the OA risk-related protein present in the sample. A difference in the level of an OA risk-related protein in the sample, relative to the level of an OA risk-related protein found an analogous sample from a subject who has no OA, in particular examples indicates that the subject has OA.

Array Substrate

The solid support can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoride, polyfluoroethylene-propylene, polyethylenevinyl alcohol, polymethylpentene, polychlorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567, herein incorporated by reference). In one example, the solid support surface is polypropylene.

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins are not amenable to non-specific binding, or when non-specific binding occurs, such materials can be readily removed from the surface without removing the oligonucleotides or proteins.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

Array Formats

A wide variety of array formats can be employed in accordance with the present disclosure. One example includes a linear array of oligonucleotide or protein bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Particularly disclosed for preparation of arrays are biaxially oriented polypropylene (BOPP) films.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554, 501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

Oligonucleotides can be bound to the solid support by either the 3' end of the oligonucleotide or by the 5' end of the oligonucleotide. One of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide or protein probes on the array include one or more labels, that permit detection of probe:target sequence complexes.

Kits

The present disclosure provides for kits that can be used to evaluate OA risk, for example to determine if a subject has OA, has an increased risk for developing OA in the future, assessing the severity of OA in a subject having OA, monitoring the progression of OA in a subject having OA or who has an increased susceptibility to developing OA, identifying those subjects with OA that will respond to a particular anti-OA therapy, or combinations thereof. Such kits allow one to determine if a subject has a differential activity of OA risk-related molecules, such as any combination of four or more of those listed in Tables 8 and 10-13.

The disclosed kits include a binding molecule, such as an oligonucleotide probe or a protein probe (such as an antibody probe) that selectively hybridizes or binds to an OA risk-related molecule that is the target of the kit. In particular examples, the probes are attached to an array, such as the arrays described herein. In one example, the kit includes probes that recognize any combination of at least four of the molecules in Tables 8 and 10-13.

The kit can further include one or more of a buffer solution, a conjugating solution for developing the signal of interest, or a detection reagent for detecting the signal of interest, each in separate packaging, such as a container. In another example, the kit includes a plurality of OA risk-related target molecules for binding with an OA detection array to serve as positive control. The target molecules can include oligonucleotides such as DNA, RNA, and peptide-nucleic acid, PCR fragments, or proteins (such as antibodies).

Osteoarthritis Therapy

The present disclosure also provides methods of treating OA in a subject determined to have an increased OA risk using the disclosed methods, such as a subject diagnosed with OA, or determined to have an increased risk of developing OA in the future. For example, if using the assays described above a change in activity in at least 4 of the OA risk-related molecules listed in Tables 8 and 10-13 is detected in the subject, for example at least 5, at least 6, at least 10, at least 13 or at least 16 of the OA risk-related molecules listed in Tables 8 and 10-13 is detected in the subject, a treatment is selected to avoid or reduce joint injury or to delay the onset of joint injury. The subject then can be treated in accordance with this selection, for example by administration of one or more anti-inflammatory agents, administration of glucosamine or chondroitin sulfate and their derivatives, instituting weight-management as a preventive strategy for weight-bearing OA, developing strategies to improve work biomechanics to lessen repetitive injury, instituting a program to reduce sports-related injuries and institute recovery programs for young adults at risk for developing OA, for example to prevent or delay the development of OA in the subject, or combinations thereof. In some examples, the treatment selected is specific and tailored for the subject, based on the analysis of that subject's profile for one or more OA risk-related molecules.

Screening Test Agents

Based on the identification of multiple OA risk-related molecules whose activity is altered in response to or to cause OA (such as those listed in Tables 8 and 10-13), the disclosure provides methods for identifying agents that can enhance, normalize, or reverse these effects. For example, the method permits identification of agents that normalize activity of an OA risk-related molecule. Normalizing activity (such as the activity) of an OA risk-related molecule can include decreasing activity of an OA risk-related molecule whose activity is increased in response to or to cause OA, or increasing activity of an OA-risk related molecule whose activity is decreased in response to or to cause OA. In another example, the method permits identification of agents that enhance the activity of an OA risk-related molecule, such as an OA risk related-molecule whose activity provides a protective effect to a subject having OA or having an increased risk of developing OA. For example, the method permits identification of agonists. In yet another example, the method permits identification of agents that decrease the activity of an OA risk-related molecule, such as an OA risk-associated molecule whose activity results in one or more negative symptoms of OA. For example, the method permits identification of antagonists.

In particular examples the identified agents can be used to treat a subject who has OA or is at increased risk for developing OA in the future. For example, a mammal (such as a human or veterinary subject) having OA or having an increased risk of developing OA in the future, can be administered one or more agents identified using the disclosed screening methods to treat the mammal.

The disclosed methods can be performed in vitro, for example by adding the test agent to cells in culture, or in vivo, for example by administering the test agent to a mammal (such as a human or a laboratory animal, for example a mouse, rat, dog, or rabbit). In particular examples, the method includes exposing the cell or mammal to conditions sufficient for mimicking or inducing OA. Such methods are known in the art. The one or more test agents are added to the cell culture or administered to the mammal under conditions sufficient to alter the activity of one or more OA-related molecules, such as at least one of the molecules listed in Tables 8 and 10-13. Subsequently, the activity of the OA risk-related molecule is determined, for example by measuring expression of one or more OA risk-related molecules or by measuring an amount of biological activity of one or more OA-related proteins. A change in the activity one or more OA risk-related molecule indicates that the test agent alters the activity of an OA risk-related molecule listed in Tables 8 and 10-13. In particular examples, the change in activity is determined by a comparison to a standard or reference value, such as an amount of activity present when no OA or risk of OA is present, or an amount of activity present when OA or risk of OA is present, or compared to a control (such as a cell or subject receiving no test agent).

Therapeutic agents identified with the disclosed approaches can be used as lead compounds to identify other agents having even greater desired activity. In addition, chemical analogs of identified chemical entities, or variants, fragments, or fusions of peptide test agents, can be tested for their ability to alter activity of an OA risk-related molecule using the disclosed assays. Candidate agents can be tested for safety in animals and then used for clinical trials in animals or humans.

Test Agents

Any suitable compound or composition can be used as a test agent, such as organic or inorganic chemicals, including aromatics, fatty acids, and carbohydrates; peptides, including monoclonal antibodies, polyclonal antibodies, and other specific binding agents; phosphopeptides; or nucleic acid molecules. In a particular example, the test agent includes a random peptide library (for example see Lam et al., *Nature* 354:82-4, 1991), random or partially degenerate, directed phosphopeptide libraries (for example see Songyang et al., *Cell* 72:767-78, 1993). A test agent can also include a complex mixture or "cocktail" of molecules.

Test agents can be pharmacologic agents already known in the art or can be compounds previously unknown to have any pharmacological activity. The compounds can be naturally occurring or designed in a laboratory. They can be isolated from microorganisms, animals, or plants, and can be produced recombinantly, or synthesized by chemical methods known in the art. If desired, test substances can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds (for example see Lam, *Anticancer Drug Des.* 12:145, 1997).

Methods for the synthesis of molecular libraries are well known in the art (see, for example, DeWitt et al., *Proc. Natl. Acad. Sci. U.S.A.* 90:6909, 1993; Erb et al. *Proc. Natl. Acad. Sci. U.S.A.* 91:11422, 1994; Zuckermann et al., *J. Med. Chem.* 37:2678, 1994; Cho et al., *Science* 261:1303, 1993; Carell et al., *Angew. Chem. Int. Ed. Engl.* 33:2059, 1994; Carell et al., *Angew. Chem. Int. Ed. Engl.* 33:2061; Gallop et al., *J. Med. Chem.* 37:1233, 1994). Libraries of compounds can be presented in solution (see, for example, Houghten, *BioTechniques* 13:412-21, 1992), or on beads (Lam, *Nature* 354, 82-4, 1991), chips (Fodor, *Nature* 364:555-6, 1993), bacteria or spores (Ladner, U.S. Pat. No. 5,223,409), plasmids (Cull et al., *Proc. Natl. Acad. Sci. U.S.A.* 89:1865-9, 1992), or phage (Scott & Smith, *Science* 249:386-90, 1990; Devlin, *Science* 249:404-6, 1990); Cwirla et al., *Proc. Natl. Acad. Sci.* 97:6378-82, 1990; Felici, *J. Mol. Biol.* 222:301-10, 1991; and Ladner, U.S. Pat. No. 5,223,409).

In vitro Assays

In one example, the method is an in vitro assay. For example, cells, such as cells that provide a model of what happens in vivo in response to or to cause OA (such as chondrocytes), are cultured under conditions sufficient for mimicking OA, such as oxidative stress. In another example, cells (for example chondrocytes) obtained from a subject having OA are used. One or more test agents are incubated with the cells under conditions sufficient for the test agent to have the desired effect on the cell, for example to alter (such as normalize) the activity of an OA-risk related molecule. In examples where the cells are treated to mimic or induce OA, the test agents can be added before, during, or after such treatment. In another example, cells are obtained from a mammal having OA and incubated with the test agent. In particular examples, the test agent has the desired effect on more than one OA risk-related molecule.

Examples of cells that can be used include, but are not limited to: chondrocytes. Chondrocyte cells can also be obtained from a subject, such as a mammal, and grown as a primary culture using standard methods. For example, chondrocytes can be obtained from cartilage (for example see Yudoh et al., *Arthritis Res Ther.* 7(2):R380-91, 2005). In one example, established chondrocyte culture cell lines are used, such as those available from American Type Culture Collection (ATCC) and other commercial sources. For example, mouse stromal cells (ATCC No. CRL-12424), which can be differentiated into chondrocytes in the appropriate medium, is a particular example of a cell line that can be used. However one skilled in the art will appreciate that other cell lines can be used.

Methods of providing conditions sufficient for mimicking or inducing OA in vitro are known in the art. For example, OA can be induced in a chondrocyte cell by culturing cells in the presence of $H_2O_2$. To mimic OA, cells from a mammal having OA can be cultured, such as chondrocytes obtained from the articular cartilage of an OA subject.

One or more test agents are incubated with the cells under conditions sufficient for the test agent to have the desired effect on the cell. In examples where cells are treated to mimic or induce OA, the test agent can be added to the cells before, after, or at substantially the same time as mimicking or inducing OA. In one example, the agent is added at least 12 hours after mimicking or inducing OA, such as at least 1 day, at least 5 days, at least 7 days, at least 14 days, at least 30 days, at least 60 days or even at least 90 days after mimicking or inducing OA.

The test agent can be incubated with the cells for a time sufficient for the test agent to have the desired effect on the cell, such as at least 10 minutes, at least 30 minutes, at least 1 hour, at least 6 hours, at least 24 hours, at least 72 hours, at least 7 days, at least 14 days, or at least 30 days.

In vivo Assays

In another example, the method is an in vivo assay. For example, agents identified as candidates in the in vitro assay can be tested in vivo for their ability to alter (such as normalize) the activity of an OA-related molecule (such as one or more of those listed in Tables 8 and 10-13). In particular examples, the test mammal spontaneously developed OA or has been exposed to conditions that induce OA. Simultaneously or at a time thereafter, one or more test agents are administered to the subject under conditions sufficient for the test agent to have the desired effect on the subject, for example to alter (such as normalize) the activity of an OA risk-related molecule or a pattern of OA risk-related molecules. In particular examples, the test agent has the desired effect on more than one OA risk-related molecule.

Methods of providing conditions sufficient for inducing OA in vivo are known in the art. For example, animal models of OA are readily available, such as rat OA models (for example see Fernihough et al., *Neurosci. Lett.* 2005 Jul. 19), mouse OA models (see Young, *Trends Pharmacol. Sci.* 26:333-5, 2005 for a review), and rabbit OA models (for example see Kobayashi et al., *Inflamm Res.* 54:249-55, 2005). OA can be induced in a mammal (such as a rat, mouse, or non-human primate), for example by partial medial meniscectomy or by injection of iodoacetate into a synovial cavity (for example see Fernihough et al., *Neurosci. Lett.* 2005 Jul. 19). In addition, animal models that spontaneously develop OA, such as STR/1N mice (for example see Averbeck et al., *J. Rheumatol.* 31:2013-20, 2004) and rhesus macaques (for example see Chateauvert et al., *J. Rheumatol.* 17:73-83, 1990) are known in the art.

One or more test agents are administered to the subject under conditions sufficient for the test agent to have the desired effect on the subject. Any appropriate method of administration can be used, such as intravenous, intramuscular, transdermal, or direct injection into the affected joint. The agent can be administered at a time subsequent to the development or inducing of OA or at substantially the same time as the development or inducing of OA. In one example, the agent is added at least 1 day, at least 5 days, at least 7 days, at least 14 days, at least 30 days, at least 60 days or even at least 90 days after the development or inducing of OA.

The test agent can be administered to the mammal in one or more doses, for example in one or more doses under conditions sufficient for the test agent to have the desired effect on the OA in the mammal, such as one, two or three administrations, such as daily, weekly, or monthly administration.

Determining Effects

The effect on the one or more test agents on the activity of one or more OA risk-related molecules can be determined using methods known in the art. For example, the effect on activity of one or more OA risk-related molecules can be determined using the arrays and methods disclosed herein.

For example, RNA can be isolated from the cultured cells exposed to the test agent, or from cells obtained from a subject administered the test agent. The isolated RNA can be labeled and exposed to an array containing one or more nucleic acid molecules (such as a primer or probe) that can specifically hybridize to one or more pre-selected OA risk-related genes, such at least 1, at least 2, or at least 3 of those listed in Tables 8 and 10-13, or to a pre-selected pattern of such genes that is associated with OA risk. In a particular example, the one or more pre-selected OA-related genes include one or more of IL-15, sVAP-1, UPAR, vCAM-1, MIP-1β, MIP1-δ, 6-Ckine, ICAM-3, TGF-β RIII, or PAI-1.

In another example, proteins from the cultured cells exposed to the test agent, or obtained from a subject administered the test agent (such as a serum sample). The sample containing proteins can be analyzed to determine amounts of expression or biological activity of one or more OA risk-associated proteins, such at least 1, at least 2, or at least 3 of those listed in Tables 8 and 10-13, or a pattern of upregulation or downregulation of pre-identified or pre-selected proteins. In a particular example, the one or more pre-selected OA-related proteins include one or more of IL-15, sVAP-1, UPAR, vCAM-1, MIP-1β, MIP1-δ, 6-Ckine, ICAM-3, TGF-β RIII, or PAI-1. In a particular example, an RCA protein chip is used to analyze the proteins.

In particular examples, differential activity of an OA risk-related molecule is compared to a standard, reference value, or a control. One example includes the amount of activity of an OA risk-related molecule present or expected in a subject who has no OA, wherein an increase or decrease in activity in a test sample of a OA-related molecule (such as those listed in Tables 8 and 10-13) compared to the control indicates that the test agent alters the activity of at least one OA risk-related molecule. Another example includes the amount of activity of an OA risk-related molecule present or expected in a subject who has OA, wherein an increase or decrease in activity in a test sample (such as gene expression, amount of protein, or biological activity of a protein) of an OA risk-related molecule (such as those listed in Tables 8 and 10-13) compared to the control indicates that the test agent alters the activity of at least one OA-related molecule. In another example, a control includes an amount of activity present in the absence of the test agent. Detecting differential activity can include measuring a change in gene expression, measuring an amount of protein, or determining an amount of the biological activity of a protein present.

Ideally, the test agent normalizes activity of the OA risk-related molecule (such as a protein) so that in the presence of the test agent, activity of the OA risk-related molecule more closely resembles the activity of the OA risk-related molecule in the absence of OA risk. That is, if activity of an OA risk-related molecule is decreased in an OA subject relative to activity of the molecule in the absence of OA risk, then the test agent ideally elevates the activity of the OA risk-related molecule in the sample receiving the test agent. Similarly, if activity of an OA risk-related molecule is elevated in an OA subject relative to activity of the molecule in the absence of OA risk, then the test agent ideally decreases the activity of the OA risk-related molecule in the sample receiving the test agent. In particular examples, differential activity is present when the test sample compared to the standard, reference value, or control a test substance either decreases or increases activity of the OA risk-related molecule by a statistically significant amount ($p \leq 0.05$) relative to the activity of the OA risk-related molecule in the absence of the test substance. In another example, differential activity is present when the test sample compared to the standard, reference value, or control (such as an amount of activity of the OA risk-associated molecule in a subject having OA) either decreases or increases activity of the OA risk-related molecule by at least four-fold, such as at least 5-fold, or at least 10-fold relative to the activity of the OA risk-related molecule in the control.

In particular examples, test agents that normalized the activity of an OA risk-related molecule are selected, for example for further clinical analysis.

High Throughput Screening

Test agents can be screened for the ability to affect the activity of (such as normalize) one or more OA risk-associated molecules (such as a protein or polynucleotide encoding the protein) using high throughput screening. Using high throughput screening, many discrete compounds can be tested in parallel so that large numbers of test substances can be quickly screened. The most widely established techniques utilize 96-well microtiter plates. The wells of the microtiter plates typically use assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., Proc. Natl. Acad. Sci. U.S.A. 19, 1614-18 (1994). The cells are placed under agarose in petri dishes, then beads that carry combinatorial compounds are placed on the surface of the agarose. The combinatorial compounds are partially released from the beads. Active compounds can be visualized as dark pigment areas because, as the compounds diffuse locally into the gel matrix, the active compounds cause the cells to change colors.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

The disclosure is further illustrated by the following non-limiting Examples.

EXAMPLE 1

Subjects Evaluated

A case-control study was nested within the Baltimore Longitudinal Study of Aging (BLSA). The BLSA is a longitudinal study of normative aging where a large cohort of volunteers was followed through comprehensive biennial examinations for more than 40 years (Shock. The physiological basis of aging. New York: Human Sciences; 1985).

Participants were community-dwelling healthy volunteers who were 19-92 years old at study entry, mostly of Caucasian race (96%) and upper middle-class socioeconomic status. Further details are provided in Table 1.

TABLE 1

Number of subjects by age group and characteristics at initial and classifying X-rays.

|  | Initial X-RAY (1984-1991) | | Classifying X-RAY (1994-1996) | |
| --- | --- | --- | --- | --- |
|  | OA (n = 21) | Controls (n = 61) | OA (n = 19) | Controls (n = 66) |
| Age (mean ± SD years) | 58.04 ± 15.18 | 52.31 ± 14.39 | 69.38 ± 15.69 | 65.71 ± 14.19 |
| Age Group |  |  |  |  |
| <45 | 3 | 16 | 1 | 6 |
| 45-70 | 12 | 36 | 6 | 31 |
| >70 | 6 | 9 | 12 | 29 |
| Men:Women | 9:12 | 25:36 | 8:11 | 29:38 |
| Body Mass Index ($kg/m^2$) | 25.38 ± 3.07 | 25.55 ± 4.37 | 26.72 ± 4.75 | 26.88 ± 4.84 |

Between 1984 and 1991 single posteroanterior (PA) radiographs of both hands and a weight-bearing, fully extended anteroposterior (AP) radiographs of both knees were obtained at one or more biannual visits between 1984 and 1991 and a repeat set of knee x-rays was obtained using the same methodology was obtained at the time of their biannual visit in 1995-1998. The mean interval between the initial and follow-up x-rays was approximately 10 years (Hochberg et al. *Osteoarthritis Cartilage* 12 Suppl A:S45-8, 2004).

All radiographs taken between 1984 and 1991 were independently evaluated for OA in 1992-1993 by two trained readers using the Kellgren-Lawrence (KL) grades as described in the Atlas of Standard Radiographs (Kellgren and Lawrence, Atlas of Standard Radiographs of Arthritis. The Epidemiology of Chronic Rheumatism. 1963;II). Definite OA of the knee was defined as KL grade 2 or higher of either knee. Hand OA was defined as a KL grade of 2 or higher at one or more of the distal interphalangeal (DIP), proximal interphalangeal (PIP) and the first carpometacarpal (CMC1) joints of either hand. Paired radiographs were read blinded from the participant's identity, time and sequence of examination by two trained readers; a third trained reader adjudicated disagreements. The intra-class correlation coefficient for agreement on KL grade between the 2 reviewers was 0.83-0.85 for baseline and follow-up films (Scott et al. *Invest. Radiol.* 28:497-501, 1993).

BLSA participants were eligible if they had two sets of hand and knee x-rays that had been scored as no evidence of OA on the baseline X-ray set, and a set of serum samples obtained over the corresponding time interval. The data reported herein are from one sample obtained concurrent to the initial x-ray, and a second sample obtained at the time of the second x-ray that discriminates cases from controls. A third sample obtained from control participants approximately 5 years prior to the initial x-ray was also examined.

Participants who had radiographic OA of one or both knees and one or both hands on the second x-ray were classified as incident OA cases. Participants with "normal" knee and hand x-rays at both time points served as controls. Three controls matched by age, gender and body mass index were selected for each incident OA case. These details are illustrated in FIG. 1.

EXAMPLE 2

Rolling Circle Amplification (RCA) Protein Microarray

Figure 2:
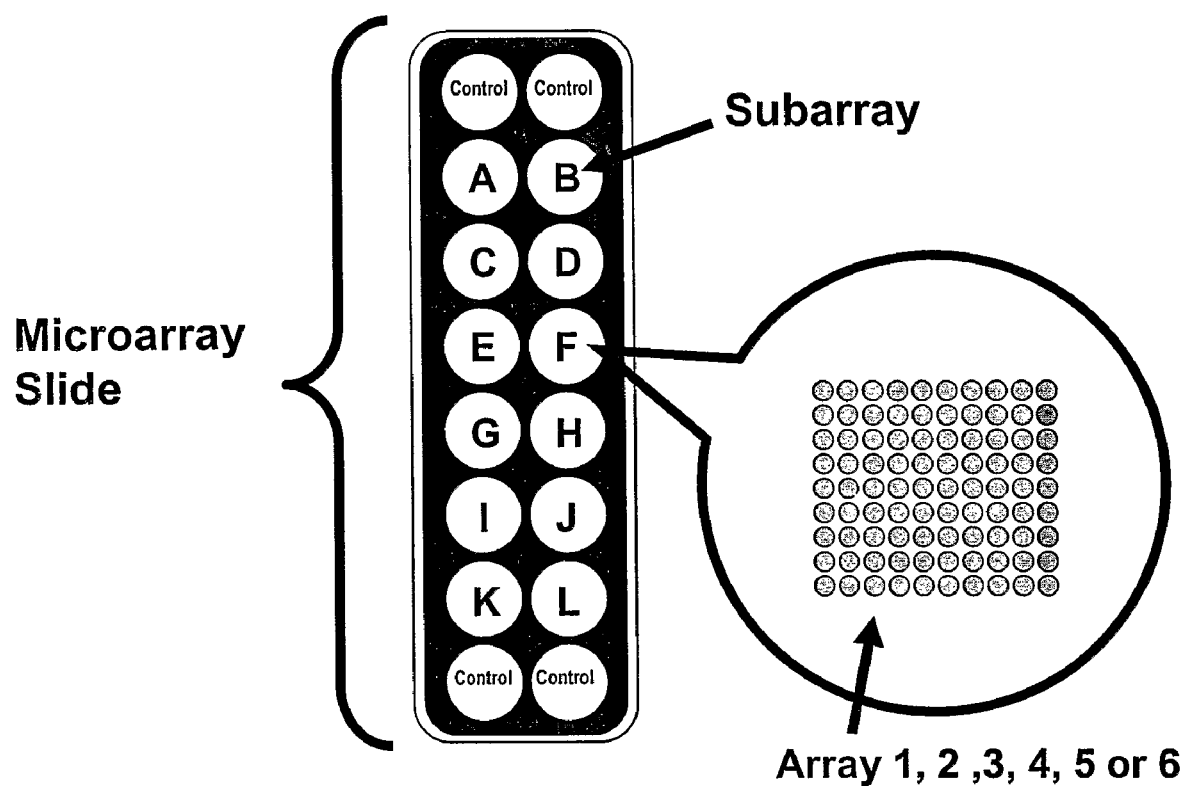
FIG. 2 is a schematic representation of a sample protein microarray slide with 16 subarrays (A-L). "Subarray" refers to the 16 wells, or circular analysis sites, on the slide. "Array" refers to the antibody content printed in a well. Each microarray slide contains only one type of array.

Glass slides were cleaned and derivatized with 3-cyanopropyltriethoxysilane. The slides were equipped with a Teflon mask that divided the slide into sixteen 0.65 cm diameter wells or circular analysis sites called subarrays (FIG. 2). Printing was accomplished with a Perkin-Elmer SpotArray Enterprise non-contact arrayer equipped with piezoelectric tips, which dispense a droplet (~350 pL) for each microarray spot. Antibodies were applied at a concentration of 0.5 mg/mL at defined positions. Each chip was printed with sixteen copies of one type of array, either array 1, 2, 3, 4, 5 or 6. A set of antibodies as indicated in Tables 2-7 below was printed with quadruplicate spots in each subarray.

After printing, chips were inspected using light microscopy. If the percentage of missing spots observed was greater than 5%, then the batch failed and the slides were discarded immediately. For all print runs described herein, 100% of the antibody features and >95% of the biotin calibrators were printed.

Microarray chips were validated in concert with a set of qualified reagents in two ways. First, mixtures of 1-3 different cytokines were prepared so as to provide a high intensity signal and applied to 14 wells of a chip (with each well being treated with a different mixture up to the total complement of detector antibodies). Two arrays were used as blank controls. The chips were developed and scanned, and the resulting signals were compared to the positional map of the particular array. Second, a titration quality control for all protein analytes of a specified array using known sample matrices was performed. Normal human serum and heparinized plasma were assayed either neat or spiked with purified recombinant cytokines representing all protein analytes in the array. Spiked mixtures were then titrated down the subarrays of a slide from 9,000 pg/mL to 37 pg/mL of spiked cytokine concentrations along with two subarrays for each un-spiked control sample. The data was quantified, and for every protein analyte in the array a titration curve was generated to examine feature intensity behavior as a function of concentration.

Taken together, this data was used to confirm the activity of array features and reagent sets.

TABLE 2

Array 1 protein analytes.

| Analyte | Name |
|---|---|
| 1 ANG | Angiogenin |
| 2 BLC (BCA-1) | B-lymphocyte chemoattractant |
| 3 EGF | Epidermal growth factor |
| 4 ENA-78 | Epithelial cell-derived neutrophil-activating peptide |
| 5 Eot | Eotaxin |
| 6 Eot-2 | Eotaxin-2 |
| 7 Fas | Fas (CD95) |
| 8 FGF-7 | Fibroblast growth factor-7 |
| 9 FGF-9 | Fibroblast growth factor-9 |
| 10 GDNF | Glial cell line derived neurotrophic factor |
| 11 GM-CSF | Granulocyte macrophage colony stimulating factor |
| 12 IL-1ra | Interleukin 1 receptor antagonist |
| 13 IL-2 sRα | Interleukin 2 soluble receptor alpha |
| 14 IL-3 | Interleukin 3 |
| 15 IL-4 | Interleukin 4 |
| 16 IL-5 | Interleukin 5 |
| 17 IL-6 | Interleukin 6 |
| 18 IL-7 | Interleukin 7 |
| 19 IL-8 | Interleukin 8 |
| 20 IL-13 | Interleukin 13 |
| 21 IL-15 | Interleukin 15 |
| 22 MCP-2 | Monocyte chemotactic protein 2 |
| 23 MCP-3 | Monocyte chemotactic protein 3 |
| 24 MIP-1α | Macrophage inflammatory protein 1 alpha |
| 25 MPIF | Myeloid progenitor inhibitory factor 1 |
| 26 OSM | Oncostatin M |
| 27 PlGF | Placental growth factor |

TABLE 3

Array 2 protein analytes.

| Analyte | Name |
|---|---|
| 1 AR | Amphiregulin |
| 2 BDNF | Brain-derived neurotrophic factor |
| 3 Flt-3 Lig | fms-like tyrosine kinase-3 ligand |
| 4 GCP-2 | Granulocyte chemotactic protein 2 |
| 5 HCC4 (NCC4) | Hemofiltrate CC chemokine 4 |
| 6 I-309 | I-309 |
| 7 IL-1α | Interleukin 1 alpha |
| 8 IL-1β | Interleukin 1 beta |
| 9 IL-2 | Interleukin 2 |
| 10 IL-17 | Interleukin 17 |
| 11 MCP-1 | Monocyte chemotactic protein 1 |
| 12 M-CSF | Macrophage colony stimulating factor |
| 13 MIG | Monokine induced by interferon gamma |
| 14 MIP-1β | Macrophage inflammatory protein 1 beta |
| 15 MIP-1δ | Macrophage inflammatory protein 1 delta |
| 16 NT-3 | Neurotrophin 3 |
| 17 NT-4 | Neurotrophin 4 |
| 18 PARC | Pulmonary and activation-regulated chemokine |
| 19 RANTES | Regulated upon activation, normal T expressed and presumably secreted |
| 20 SCF | Stem cell factor |
| 21 sgp130 | Soluble glycoprotein 130 |
| 22 TARC | Thymus and activation regulated chemokine |
| 23 TNF-RI | Tumor necrosis factor receptor I |
| 24 TNF-α | Tumor necrosis factor alpha |
| 25 TNF-β | Tumor necrosis factor beta |
| 26 VEGF | Vascular endothelial growth factor |

TABLE 4

Array 3 protein analytes.

| Analyte | Name |
|---|---|
| 1 BTC | Betacellulin |
| 2 DR6 | Death receptor 6 |
| 3 Fas Lig | Fas ligand |
| 4 FGF acid (FGF-1) | Fibroblast growth factor acidic |
| 5 Fractalkine | Fractalkine |
| 6 GRO-β | Growth related oncogene beta |
| 7 HCC-1 | Hemofiltrate CC chemokine 1 |
| 8 HGF | Hepatocyte growth factor |
| 9 HVEM | Herpes virus entry mediator |
| 10 ICAM-3 (CD50) | Intercellular adhesion molecule 3 |
| 11 IGFBP-2 | Insulin-like growth factor binding protein 2 |
| 12 IL-2 Rγ | Interleukin 2 receptor gamma |
| 13 IL-5 Rα (CD125) | Interleukin 5 receptor alpha |
| 14 IL-9 | Interleukin 9 |
| 15 Leptin/OB | Leptin |
| 16 L-Selectin (CD62L) | Leukocyte selectin |
| 17 MCP-4 | Monocyte chemotactic protein 4 |
| 18 MIP-3β | Macrophage inflammatory protein 3 beta |
| 19 MMP-7 (total) | Matrix metalloproteinase 7 |
| 20 MMP-9 | Matrix metalloproteinase 9 |
| 21 PECAM-1 (CD31) | Platelet endothelial cell adhesion molecule-1 |
| 22 RANK | Receptor activator of NF-kappa-B |
| 23 SCF R | Stem cell factor receptor |
| 24 TIMP-1 | Tissue inhibitors of metalloproteinases 1 |
| 25 TRAIL R4 | TNF-related apoptosis-inducing ligand receptor 4 |
| 26 VEGF-R2 (Flk-1/KDR) | Vascular endothelial growth factor receptor 2 |
| 27 ST2 | Interleukin 1 receptor 4 |

TABLE 5

Array 4 protein analytes.

| Analyte | Name |
|---|---|
| 1 ALCAM | Activated leukocyte cell adhesion molecule |
| 2 β-NGF | beta-nerve growth factor |
| 3 CD27 | CD27 |
| 4 CTACK | Cutaneous T-cell attracting chemokine |
| 5 CD30 | CD30 |
| 6 Eot-3 | Eotaxin-3 |
| 7 FGF-2 | Fibroblast growth factor-2 (FGF-basic) |
| 8 FGF-4 | Fibroblast growth factor-4 |
| 9 Follistatin | Follistatin |
| 10 GRO-γ | Growth related oncogene gamma |
| 11 ICAM-1 | Intercellular adhesion molecule 1 |
| 12 IFN-γ | Interferon gamma |
| 13 IFN-ω | Interferon omega |
| 14 IGF-1R | Insulin-like growth factor I receptor |
| 15 IGFBP-1 | Insulin-like growth factor binding protein 1 |
| 16 IGFBP-3 | Insulin-like growth factor binding protein 3 |
| 17 IGFBP-4 | Insulin-like growth factor binding protein 4 |
| 18 IGF-II | Insulin-like growth factor II |
| 19 IL-1 sR1 | Interleukin 1 soluble receptor I |
| 20 IL-1 sRII | Interleukin 1 soluble receptor II |
| 21 IL-10 Rβ | Interleukin 10 receptor beta |
| 22 IL-16 | Interleukin 16 |
| 23 IL-2 Rβ | Interleukin 2 receptor beta |
| 24 I-TAC | Interferon gamma-inducible T cell alpha chemoattractant |
| 25 Lptn | Lymphotactin |
| 26 LT βR | lymphotoxin-beta receptor |
| 27 M-CSF R | Macrophage colony stimulating factor receptor |
| 28 MIP-3α | Macrophage inflammatory protein 3 alpha |
| 29 MMP-10 | Matrix metalloproteinase 10 |
| 30 PDGF Rα | Platelet-derived growth factor receptor alpha |
| 31 PF4 | Platelet factor-4 |
| 32 sVAP-1 | Soluble Vascular Adhesion Protein-1 |
| 33 TGF-α | Transforming growth factor alpha |
| 34 TIMP-2 | Tissue inhibitors of metalloproteinases 2 |
| 35 TRAIL R1 | TNF-related apoptosis-inducing ligand receptor 1 |

TABLE 5-continued

Array 4 protein analytes.

| Analyte | Name |
|---|---|
| 36 VE-cadherin | Vascular Endothelial Cadherin |
| 37 VEGF-D | Vascular endothelial growth factor-D |

TABLE 6

Array 5 protein analytes.

| Analyte | Name |
|---|---|
| 1 4-1BB (CD137) | 4-1BB |
| 2 ACE-2 | Angiotensin I converting enzyme-2 |
| 3 AFP | Alpha fetoprotein |
| 4 AgRP | Agouti-related protein |
| 5 CD141 | Thrombomodulin/CD141 |
| 6 CD40 | CD40 |
| 7 CNTF Rα | Ciliary neurotrophic factor receptor alpha |
| 8 CRP | C-reactive protein |
| 9 D-Dimer | D-Dimer |
| 10 E-Selectin | E-selectin |
| 11 HCG | Human chorionic gonadotrophin |
| 12 IGFBP-6 | Insulin-like Growth Factor Binding Protein 6 |
| 13 IL-12 (p40) | Interleukin 12 p40 |
| 14 IL-18 | Interleukin 18 |
| 15 LIF Rα (gp190) | Leukemia inhibitory factor soluble receptor alpha |
| 16 MIF | Macrophage migration inhibitory factor |
| 17 MMP-8 (total) | Matrix Metalloproteinase-8 |
| 18 NAP-2 | Neutrophil Activating Peptide 2 |
| 19 Neutrophil elastase | Neutrophil elastase |
| 20 PAI-II | Plasminogen activator inhibitor-II |
| 21 Prolactin | Prolactin |
| 22 Protein C | Human Protein C |
| 23 Protein S | Human Protein S |
| 24 P-Selectin | P-Selectin |
| 25 TSH | Thyroid stimulating hormone |

TABLE 7

Array 6 protein analytes.

| Analyte | Name |
|---|---|
| 1 6Ckine | 6Ckine |
| 2 ACE | Angiotensin converting enzyme |
| 3 CA 125 | Cancer antigen 125 |
| 4 CNTF | Ciliary neurotrophic factor |
| 5 Endostatin | Endostatin |
| 6 Endothelin 3 | Endothelin 3 |
| 7 ErbB1 | Epidermal growth factor receptor 1 |
| 8 ErbB2 | Epidermal growth factor receptor 2 |
| 9 FGF R3 (IIIc) | Fibroblast growth factor receptor 3 IIIc isoform |
| 10 FGF-6 | Fibroblast growth factor-6 |
| 11 FGF-R3 (IIIb) | Fibroblast growth factor receptor 3 IIIb isoform |
| 12 G-CSF | Granulocyte colony stimulating factor |
| 13 HB-EGF | Heparin-Binding EGF-like Growth Factor |
| 14 IFN-a | Interferon alpha |
| 15 LIF | Leukemia inhibitory factor |
| 16 MMP-1 | Matrix metalloproteinase 1 |
| 17 MMP-2 | Matrix metalloproteinase 2 |
| 18 Osteopontin | Osteopontin |
| 19 PAI-1 | Plasminogen activator inhibitor type 1 |
| 20 PDGF Rb | Platelet-derived growth factor receptor beta |
| 21 PEDF | Pigment epithelium-derived factor |
| 22 sVCAM-1 | Souble VCAM-1 |
| 23 TGF-b RIII | Transforming growth factor beta receptor III |
| 24 Tie-2 | Tyrosine kinase with Ig and EGF homology domains 2 |

TABLE 7-continued

Array 6 protein analytes.

| Analyte | Name |
|---|---|
| 25 uPA | Urokinase plasminogen activator |
| 26 uPAR | Urokinase plasminogen activator receptor |
| 27 VEGF R3 | VEGF receptor 3 |

EXAMPLE 3

Rolling Circle Amplification (RCA) Immunoassay

This example describes methods used to analyze the presence of the 169 proteins listed in Tables 2-7 in serum obtained at least two different time points (at the time of classification and 10 years before) from the study participants. One skilled in the art will appreciate that similar methods can be used to analyze other proteins and to analyze different samples (such as urine or synovial fluid). The basics of performing immunoassays with RCA signal amplification are known (for example see Schweitzer et al., *Nat. Biotechol.* 20:359-65, 2002; Kingsmore et al. *Curr. Opin. Biotechnol.* 14:74-81, 2003; and Perlee et al. *Proteome Sci.* 2:9, 2004).

Prior to assay, the slides were removed from storage at room temperature in sealed containers and opened in a humidity controlled chamber (45-55%). Slides were blocked with Seablock (Pierce Chemical Co.), diluted 1:1 with PBS for 1 hour at 37° C. in a humidified chamber. Following removal of the blocking solution, they were washed twice with 1×PBS/0.5% Brij 35 prior to application of sample. Each of the 169 proteins (Tables 2-7) were tested in quadruplicate. Four controls were included on each sample slide with known concentrations corresponding to four anchor points on the full titration curve. The test samples were assayed on the remaining 12 subarrays.

Subjects without significant OA on initial knee and hand x-rays obtained between 1984 and 1991 were classified as OA cases (n=19) or no OA controls (n=66) by follow-up x-rays performed between 1995 and 1998, and matched by age, sex and body mass index. Serum samples obtained at the time of classification and 10 years before were applied to the microarray platforms that assayed 169 proteins. All serum samples were obtained from participants after an overnight fast, immediately processed, and stored at −80° C. until testing. Frozen serum samples (216 samples, 170 from no OA and 46 from OA subjects) were thawed, centrifuged to remove particulate matter and mixed with 0.25 mg/ml Heteroblock (Omega), 0.25 mg/ml IIR (Bioreclamation) and 0.1% Tween-20 prior to the assay. Twenty ILL of the treated sample were then applied to each subarray, and the formed complexes detected using RCA indirect immunoassay.

The slides were scanned using a LS200 scanner (TECAN). Scanned images were analyzed using proprietary software (Molecular Staging, Inc.). The fluorescence intensity of microarray spots was analyzed for each quality control and sample, and the resulting mean intensity values were determined. Dose-response curves for selected proteins were examined to ensure that the detected intensity was well above background and exhibited increasing intensity with increasing analyte concentration. Proteins with mean signal intensities 4-fold higher than control blanks were normalized by Z-scores and compared between cases and controls using multivariate techniques (significance $p<0.05$).

Slide-to-slide precision was improved using regression-based normalization. The slide-to-slide variability (CV) was 17%, 20%, 17%, 19%, 18%, and 17% for Arrays 1, 2, 3, 4, 5 and 6, respectively. More than 88% of the samples passed quality control, exceeding the 85% minimum acceptable pass rate, indicative of successful completion of data generation according to MSI SOP. The main source of failure was sample shortfall.

EXAMPLE 4

Identification of OA Biomarkers Using Analysis of Covariance

This example describes methods used to analyze the data obtained in Example 3. Example 5 describes another algorithm used to analyze the data.

Data were logarithm base two transformed to stabilize variance and improve normality of the data. Of the 169 protein analytes tested, 68 showed total changes (variance) higher than that of the non-specific feature BLANK. The 68 protein analytes with average intensity differences 4-fold higher than BLANK were included in the statistical analysis. Evaluation of blank was included to safeguard against non-specific signal. Analysis of blank is accomplished by looking at variance decomposition for each array. Variance due to experimental error was comparable for most of the protein analytes and generally lower than biological variability. This indicates that assay reproducibility was sufficiently low to detect biological differences. However, the BLANK feature printed in each well (containing carrier protein used in printing the capture antibodies), shows variance larger than the experimental error and often comparable to the variance observed for some of the survey protein analytes.

Ideally, variance of BLANK should be equivalent to the observed experimental error. Although there are different strategies to perform BLANK adjustment, the method applied is based on the specific platform experience. The procedure represents a conservative approach requiring the total variance of a specific feature to be higher than the variance of BLANK. In other words, the variance of BLANK is used as a measure of our experimental error. In addition, the average intensity of a specific feature was required to be 4-fold higher than BLANK (on a linear scale).

Analysis of covariance was used to determine protein analyte changes associated with age and OA. SAS® MIXED procedure (SAS Institute Inc., 1992, SAS Technical Report P-229, *SAS/STAT Software: Changes and Enhancements, Release* 6.07, Cary, N.C.: SAS Institute Inc.) was applied to determine significant changes in protein analyte expression with age and OA. The PROC Mixed algorithm was selected based on stability to missing values, ability to fine tune covariance structures for more advanced modeling approaches, and enhanced power compared to univariate tests.

Several statistical models were used to test the association of protein analyte level with age and diagnosis. Three within subject models (AgeIndependent, Common slope and Different slopes) were fitted using baseline (Time point 1) protein analyte levels and changes with age as a covariate:

AgeIndependent model: ExpressionAtTimePoint2=Baseline+OA+gender

Common slope model: ExpressionAtTimePoint2=Baseline+OA+dage+gender, (where dage=AgeAtTimepoint2−AgeAtBaseline)

Different slopes model: ExpressionAtTimePoint2=Baseline+OA+dage*OA+gender

These models reflect a longitudinal analysis, which allows for adjustment for within subject effects, such as differences in baseline values.

Similarly, three between subjects models (AgeIndependent, Common slope and Different slopes) were fitted at time point 1 and time point 2 without adjustment for baseline:

AgeIndependent model: (ExpressionAtTimePoint1 or ExpressionAtTimePoint2)=OA+gender Common slope model: (ExpressionAtTimePoint1 or ExpressionAtTimePoint2)=OA+age+gender, where age is the age of the individual at particular time point.

Different slopes model: (ExpressionAtTimePoint1 or ExpressionAtTimePoint2)=OA+age*OA+gender.

These models reflect a cross-sectional analysis.

The approach to select a proper model for each protein analyte was:

1. Check that slopes are different from zero using model Expression=[Baseline]+OA+gender+age*OA;
2. If effect age*OA is significant check model Expression=[Baseline]+gender+OA+age+age*OA;
3. If age*OA is significant in step 2, select Different slope model
4. If age*OA is non-significant in step 2, select Common slope model
5. If age*OA in non-significant in step 1, select AgeIndependent model Results of the fitting are linear regression equations. Statistical significance of each term in the model was determined using Type III sum of squares from the PROC MIXED procedure. Effect was considered significant if the p-value was ≦0.05. Protein analytes with a statistically significant (p-value<0.05) difference in expression for effects associated with OA (OA, OA*age, OA*age2) are shown in Table 8. The "Model" column in Table 8 represents the 3 different models discussed above. "Longitudinal" in the "StudyType" column relates to models with a baseline as a covariate. "Baseline" or "TimePoint 2" in the "Study type" column indicate that expression levels at Baseline or "Time Point 2" were used as left side in the models. As shown in Table 8, 19 proteins differed significantly (p≦0.05) in expression associated with OA as compared to healthy controls. Expression of 11 of these 19 protein analytes was significantly different for more than one effect.

TABLE 8

Proteins showing a significant difference (p-value ≦ 0.05) in expression between OA and healthy controls with time

| Protein | Effect | Model | Study Type | OA Trend | p-value |
| --- | --- | --- | --- | --- | --- |
| 6Ckine | dage*OA | DifferentSlope | Longitudinal | Increases with time in OA | <.0001 |
| BDNF | age*OA | DifferentSlope | Baseline | Higher at older age in OA; | 0.002 |
| BDNF | OA | DifferentSlope | Baseline | Lower at younger age in OA | <.0001 |

TABLE 8-continued

Proteins showing a significant difference (p-value ≦ 0.05) in expression between OA and healthy controls with time

| Protein | Effect | Model | Study Type | OA Trend | p-value |
|---|---|---|---|---|---|
| BDNF | age*OA | DifferentSlope | TimePoint 2 | at both time points | 0.007 |
| BDNF | OA | DifferentSlope | TimePoint 2 | | 0.001 |
| EGF | age*OA | DifferentSlope | Baseline | Higher at older age in OA; | <.0001 |
| EGF | OA | DifferentSlope | Baseline | Lower at younger age in OA | 0.02 |
| EGF | OA | AgeIndependent | TimePoint 2 | OA lower than controls | 0.009 |
| Eot2 | OA | AgeIndependent | TimePoint 2 | OA lower than controls | <.0001 |
| HCC1 | OA | AgeIndependent | Baseline | OA higher than controls | 0.02 |
| ICAM3 | OA | AgeIndependent | TimePoint 2 | OA higher than controls | 0.02 |
| ICAM3 | dage*OA | DifferentSlope | Longitudinal | Increases with age in OA | 0.02 |
| IGFBP-4 | OA | AgeIndependent | TimePoint 2 | OA higher than controls | 0.03 |
| IL-2 | age*OA | DifferentSlope | TimePoint 2 | Higher at older age in OA | <.0001 |
| IL-2 | OA | DifferentSlope | TimePoint 2 | OA higher | 0.001 |
| Leptin | OA | AgeIndependent | Baseline | OA higher than controls | 0.05 |
| MIG | age*OA | DifferentSlope | TimePoint 2 | Higher at older age in OA | <.0001 |
| MIG | OA | DifferentSlope | TimePoint 2 | OA higher than controls | 0.02 |
| MIP-1β | OA | AgeIndependent | Longitudinal | Increases with time in OA | 0.02 |
| MIP-1δ | OA | AgeIndependent | Longitudinal | Decreases with time in OA | 0.02 |
| MMP7 | OA | Common Slope | Baseline | OA higher than controls | 0.007 |
| MMP7 | age*OA | DifferentSlope | TimePoint 2 | Higher at younger age in OA | <.0001 |
| MMP7 | OA | DifferentSlope | TimePoint 2 | OA higher than controls | 0.001 |
| MPIF-1 | age*OA | DifferentSlope | TimePoint 2 | Higher at older age in OA | 0.0005 |
| MPIF-1 | OA | DifferentSlope | TimePoint 2 | OA higher than control | 0.006 |
| Prolactin | age*OA | DifferentSlope | Baseline | Higher with age in Controls, | 0.001 |
| Prolactin | OA | DifferentSlope | Baseline | no difference with age in OA | 0.05 |
| TARC | OA | Common Slope | TimePoint 2 | Lower in OA than controls | 0.02 |
| TGF-b RIII | OA | AgeIndependent | TimePoint 2 | OA higher | 0.001 |
| TGF-b RIII | dage*OA | DifferentSlope | Longitudinal | Higher at older age in OA | 0.02 |
| UPAR | dage*OA | DifferentSlope | Longitudinal | Increases over time in OA | <.0001 |
| UPAR | OA | DifferentSlope | Longitudinal | | 0.02 |
| VCAM-1 | dage*OA | DifferentSlope | Longitudinal | Increases over time in OA | 0.02 |
| VCAM-1 | OA | DifferentSlope | Longitudinal | | 0.01 |

The fitting of the data into above statistical models results in two linear regression equations. One equation is linear fit between expression values of OA patients and time. Another regression equation is linear fit between expression values of Healthy controls and time. Each linear regression can be described by intercept and slope. Error in estimation of slopes and intercepts can also be determined. It is possible to test hypothesis if slopes are different between linear fits of OA and Healthy controls. It is also possible to compare if intercepts of linear fits of OA and Healthy controls are different. FIGS. 3A-D illustrate different combinations of slopes and intercepts for following statistical models: DifferentSlope, Common Slope and AgeIndependent.

Figure 3A:
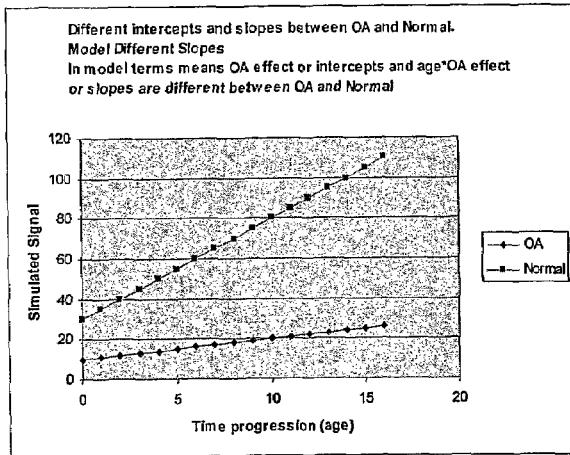
FIGS. 3A-D are schematic representations showing simulation of different models and effects of slope and intercepts. (A) different intercepts and slopes between OA and normal; (B) different slopes but the same intercepts between OA and normal; (C) different intercepts but the same slopes between OA and normal; (D) different intercepts between OA and normal but slopes are equal to zero.
Figure 3B:
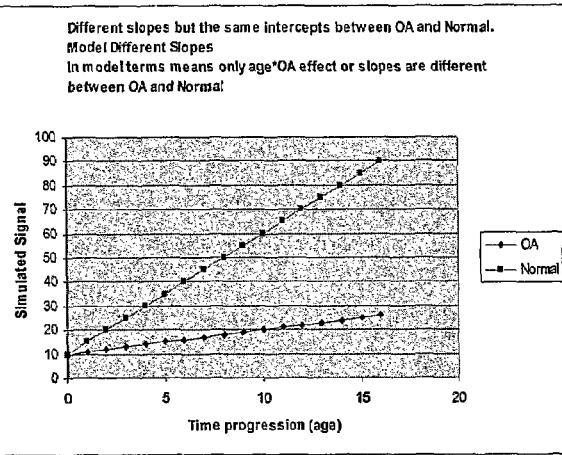

If effect OA is significant, this indicates that intercepts of linear regression fit of protein expression are different between OA and Healthy controls (see FIGS. 3A, C and D).

Effect dage*OA (where dage=AgeAtTimepoint2−AgeAtBaseline) is specific to longitudinal study type. If effects dage*OA is significant this indicates that slopes of linear regression fit of protein expression with time are different between OA and healthy controls (similar to FIGS. 3A and B).

Effect age*OA (where age is AgeAtTimepoint2 or AgeAtBaseline) is specific to TimePoint 2 and Baseline studies type. If effects age*OA is significant, this indicates that slopes of linear regression fit of protein expression with time are different between OA and healthy controls (similar to FIGS. 3A and B).

Figure 3C:
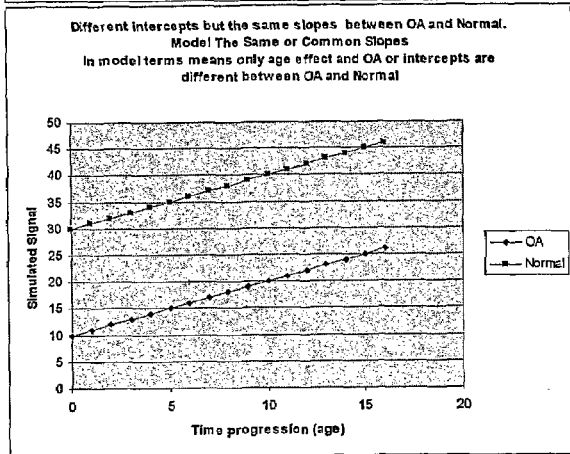

Common slope model is illustrated in FIG. 3C. It shows that lines of linear fit for OA and Healthy controls are parallel to each other, which means they have the same slope. Common slope models were limited to models that have significant difference in intercepts, which means OA effect for common slope model should be significant (p-value≦0.05).

Figure 3D:
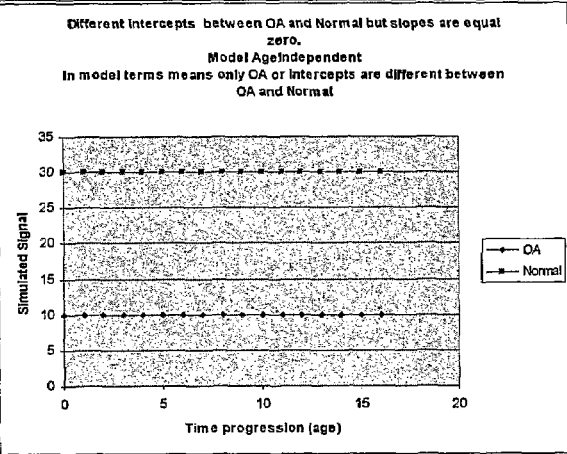

Trend in AgeIndepedendent is illustrated in FIG. 3D. It shows that expression levels do not change with time, which is indicative of slope zero and demonstrate difference in intercepts or OA effect.

Figure 4:
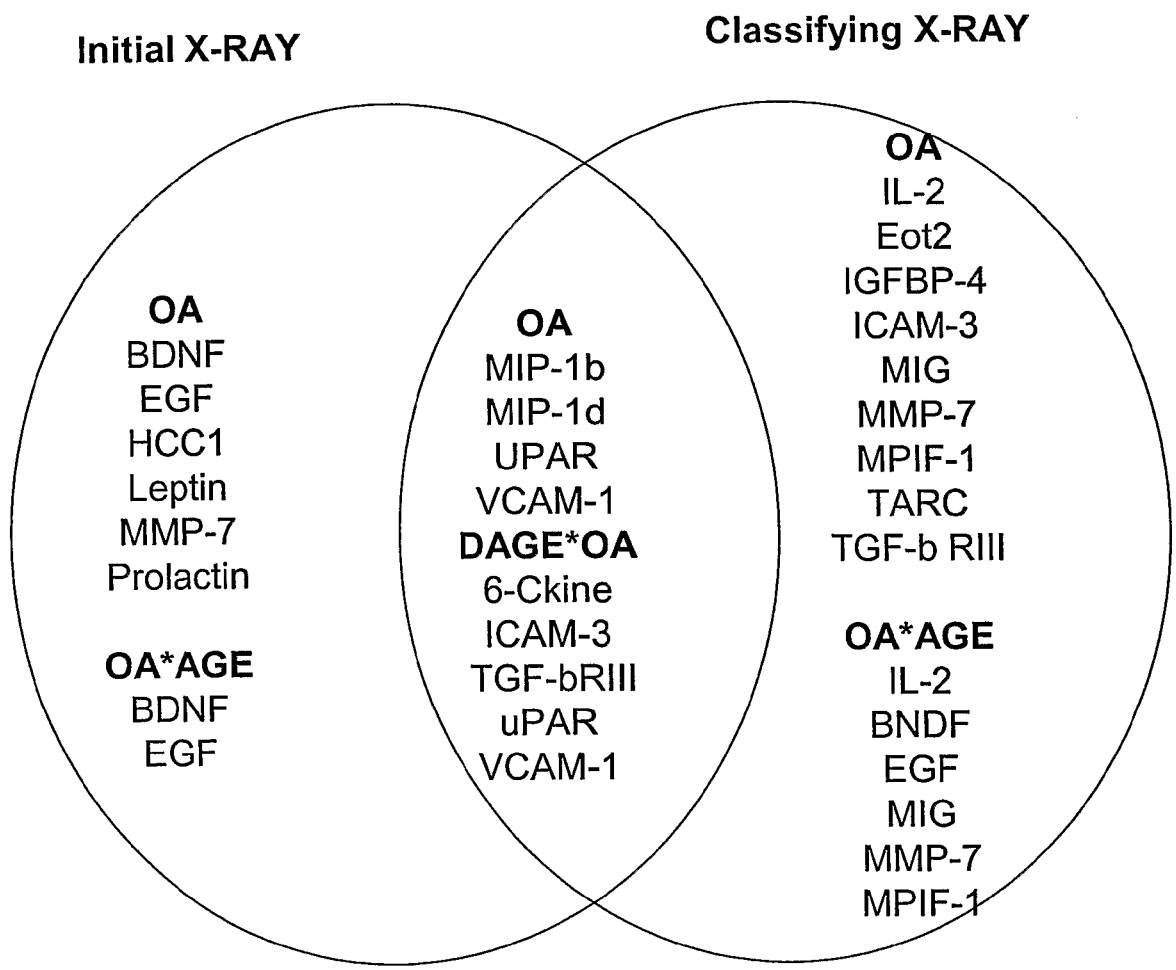
FIG. 4 is a Ven diagram showing proteins identified using analysis of covariance wherein expression was changed before the development of OA and those wherein expression was changed when OA was present.

A summary of the results is presented in FIG. 4. Proteins listed on the left are those whose activity was altered prior to development of OA, and thus can be used to predict the risk of a subject to develop OA in the future. Proteins on the right are those whose activity was altered during established OA, and thus can be used to diagnose or monitor OA progression. Proteins listed in the center are those whose activity was altered before and after development of OA, and thus can be used to predict the risk of a subject to develop OA in the future, diagnose, monitor OA progression, determine OA severity, or combinations thereof.

BDNF, EGF and prolactin demonstrated significantly different trends with age between OA and healthy controls at baseline. BDNF and EGF increased with age in OA patients and decreased in healthy controls. In contrast, prolactin levels increased in healthy controls and remained stabilized in OA patients.

OA effect and age*OA effects of expression differences of BDNF, EGF and MMP7 between OA and Healthy Controls are significant at Baseline. It indicates that intercepts and slopes are different between linear fits. Therefore, significant differences in expression of BDNF, EGF, MMP7 and prolactin can be used to determine OA risk, such as the risk of developing OA in the future.

HCC1 and leptin levels were also significantly different between OA and healthy controls at baseline independent of age, but not at the later time point. This indicates that HCC1 and leptin may be involved in initiating OA.

Levels of BDNF, IL-2 and MIG increased with age in OA patients relative to healthy controls while levels of MMP-7 and MPIF-1 decreased with age in OA patients relative to healthy controls.

Levels of EGF and EoT2 were lower in OA patients and independent of age. In contrast, levels of ICAM3, IGFBP-4 and TGF b III were higher in OA patients.

Adjustment for within-subject effects such as differences in baseline, can be achieved in longitudinal designed studies thereby adding power to the findings (see "Longitudinal" in Table 8). Levels of 6Ckine, ICAM3, uPAR and VCAM-1 increased in OA patients with time prior to diagnosis, relative to protein analyte levels observed in healthy controls. Therefore, such proteins can be used to predict risk of developing OA in the future.

The models that were significant in the longitudinal analyses were displayed as quantity per change in age (years), per adjusted year of change: 6ckine slopes lines cross-over is at 7 years; ICAM3 slope lines cross-over is at 6 years; MIP-1b slope lines cross-over at 10 years; MIP-1d slope lines cross-over at 6 years; TGFb RIII slope lines cross-over at 5 years; UPAR slope lines cross-over at 9 years; and VCAM-1 slope lines cross-over at 9-10 years.

EXAMPLE 5

Identification of Aging Biomarkers

Similar statistical models used in Example 4 were used to determine the association of protein analyte levels with age, except that the analysis was performed exclusively on protein analyte levels from healthy controls.

Three within subject models (AgeIndependent, Common slope and Different slopes) were fitted with baseline protein analyte levels and changes with age as a covariate.
AgeIndependent model:
ExpressionAtTimePoint2or3=Baseline+gender.
Common slope model:
ExpressionAtTimePoint2or3=Baseline+gender+dage
(where dage=AgeAtTimepoint2 or 3−AgeAtBaseline).
Different slopes model:
ExpressionAtTimePoint2or3=Baseline+gender+ age*gender.

These models reflect a longitudinal analysis, which allows for adjustment for within subject effects, such as differences in baseline values Three between-subjects models (AgeIndependent, Common slope and Different slopes) were fitted at time point 1:
AgeIndependent model:
ExpressionAtTimePoint1=gender.
Common slope model: ExpressionAtTimePoint1=age+ gender, where age is the age of the individual at time point 1.
Different slopes model:
ExpressionAtTimePoint1=age*gender+gender.

These models reflect a cross-sectional analysis.

The approach to select a proper model for each protein analyte was:
1. Check that slopes are different from zero using model Expression=[Baseline]+gender+age*gender;
2. If effect age*OA is significant check model Expression= [Baseline]+gender+age+age*gender;
3. If age*gender is significant in step 2 select Different slope model 4. If age*gender is non-significant in step 2 select Common slope model
5. If age*gender in non-significant in step 1 select Age-Independent model Results of the fitting are linear regression equations. Statistical significance of each term in the model was determined using Type III sum of squares from the PROC MIXED procedure. Effect was considered significant if the p-value was less than or equal to 0.05.

Protein analytes with a statistically significant (p-value≦0.05) difference in expression for effects associated with age (dage, dage*gender, age, gender*age) are shown in Table 9. The "Model" column in Table 9 represents the 3 different models discussed above. "Longitudinal" in the "Study Type" column reflects models with baseline as a covariate. "Baseline" in the "Study Type" column indicates that expression levels at baseline were used as left side in the models. As shown in Table 9, 39 proteins differed significantly (p≦0.05) in expression associated with age and gender in samples from healthy controls. Expression of 15 of these 39 protein analytes was significantly different for more than one effect.

TABLE 9

Proteins showing significant difference in expression with time.

| Protein | Effect | Model | Study Type | p-value |
|---|---|---|---|---|
| 6Ckine | age | Common Slope | Baseline | 0.005 |
| 6Ckine | dage | Common Slope | Longitudinal | <0.001 |
| AFP | age | Common Slope | Baseline | <0.001 |
| AFP | dage*gender_ | Different Slope | Within | 0.019 |
| BDNF | age | Common Slope | Baseline | 0.021 |
| BDNF | dage*gender_ | Different Slope | Within | <0.001 |
| CNTF Ra | dage | Common Slope | Within | 0.012 |
| CTACK | age | Common Slope | Baseline | 0.012 |
| CTACK | dage | Common Slope | Within | 0.001 |
| DR6 | age*gender_ | Different Slope | Baseline | 0.010 |
| EGF | age | Common Slope | Baseline | <0.001 |
| EGF | dage | Common Slope | Within | 0.002 |
| ENA-78 | age | Common Slope | Baseline | 0.001 |
| Eot2 | dage | Common Slope | Within | 0.001 |
| HCC4 | age | Common Slope | Baseline | 0.012 |
| HCC4 | dage*gender_ | Different Slope | Within | <0.001 |
| HVEM | age*gender_ | Different Slope | Baseline | 0.001 |
| ICAM3 | age*gender_ | Different Slope | Baseline | 0.006 |
| IGFBP-1 | dage | Common Slope | Within | <0.001 |
| IGFBP2 | age*gender_ | Different Slope | Baseline | 0.043 |
| IGFBP2 | dage*gender_ | Different Slope | Within | 0.001 |
| IGFBP-4 | dage*gender_ | Different Slope | Within | <0.001 |
| IGFBP-6 | age | Common Slope | Baseline | <0.001 |
| IGFBP-6 | dage*gender_ | Different Slope | Within | <0.001 |
| IGF-II | dage | Common Slope | Within | 0.004 |
| IL-17 | dage | Common Slope | Within | <0.001 |
| IL-18 | age*gender_ | Different Slope | Baseline | 0.006 |
| IL-2 | age | Common Slope | Baseline | 0.008 |
| IL-2 | dage*gender_ | Different Slope | Within | <0.001 |
| IL-8 | age*gender_ | Different Slope | Baseline | 0.046 |
| MIF | dage | Common Slope | Within | 0.009 |
| MIG | age*gender_ | Different Slope | Baseline | <0.001 |
| MMP-1 | age | Common Slope | Baseline | 0.003 |
| MMP-1 | dage | Common Slope | Within | 0.002 |
| MMP7 | age | Common Slope | Baseline | <0.001 |
| MMP7 | dage | Common Slope | Within | 0.014 |
| MMP-8 | dage*gender_ | Different Slope | Within | <0.001 |
| MMP9 | dage | Common Slope | Within | <0.001 |
| MPIF-1 | age | Common Slope | Baseline | 0.009 |
| MPIF-1 | dage | Common Slope | Within | 0.015 |
| OPN | age | Common Slope | Baseline | 0.002 |
| OPN | dage | Common Slope | Within | <0.001 |
| OSM | dage*gender_ | Different Slope | Within | <0.001 |
| PECAM1 | dage | Common Slope | Within | 0.002 |
| Prolactin | age | Common Slope | Baseline | 0.001 |
| TGF-b RIII | age | Common Slope | Baseline | 0.003 |
| TGF-b RIII | dage | Common Slope | Within | 0.020 |

TABLE 9-continued

Proteins showing significant difference in expression with time.

| Protein | Effect | Model | Study Type | p-value |
|---|---|---|---|---|
| Tie-2 | dage*gender_ | Different Slope | Within | <0.001 |
| TIMP1 | dage | Common Slope | Within | 0.003 |
| uPAR | age | Common Slope | Baseline | 0.009 |
| uPAR | dage | Common Slope | Within | 0.001 |
| VEGF | dage | Common Slope | Within | <0.001 |
| VEGF R2 | age*gender_ | Different Slope | Baseline | <0.001 |
| VEGF R3 | dage | Common Slope | Within | 0.001 |

The interpretation is identical to one provided for Table 8, except that gender is substituted for OA.

Levels of analytes 6Ckine, CTACK, EGF, ENA-78, EOT2, IGFBP-1, IGF-II, IL-17, MIF, MMP-1, MMP-7, MMP-9, MPIF-1, OPN, PECAM1, Prolactin, TGF-b RIII, TIMP1, UPAR, VEGF and VEGF R3 change with age.

AFP, BDNF, HCC4, IGFBP-6, IL-2 show gender-independent changes with age at baseline, but age related changes become sensitive to gender between time points 1, 2 and 3 in the longitudinal study.

IGFBP-2 demonstrates different age-dependent changes between genders.

Based on these results, these molecules can be used as a control for aging.

EXAMPLE 6

Analysis of Data Using Mixed Model ANOVA and Significant Analysis of Microarray (SAM)

This example describes mixed model ANOVA and significant analysis of microarray (SAM) methods to analyze the data obtained in Example 4.

All analyses were performed on mean fluorescence intensity (MFI) for all proteins that were 4-fold greater than background, normalized by Z-scores. Proteins that were differentially expressed between OA cases and controls using mixed model ANOVA and significant analysis of microarray (SAM) were identified. In the ANOVA analysis, individual samples were treated as the random effect, visit time treated as the repeated measure, and "OA" versus "no OA" as a fixed effect. In the SAM analysis, differentially expressed proteins were determined based on the false discovery rate (FDR<0.27) via permutations of the repeated measurement (for example see Tusher et al. *Proc. Natl. Acad. Sci. USA* 98:5116-21, 2001).

For proteins identified by ANOVA and SAM (see FIG. 5), sensitivity and specificity in discriminating cases from controls were evaluated with the receiver operating characteristic (ROC) curves. In particular, differentially expressed proteins as well as all measured proteins were used as prediction variables for the decision tree classification, and the results were pooled into curves.

Figure 5:
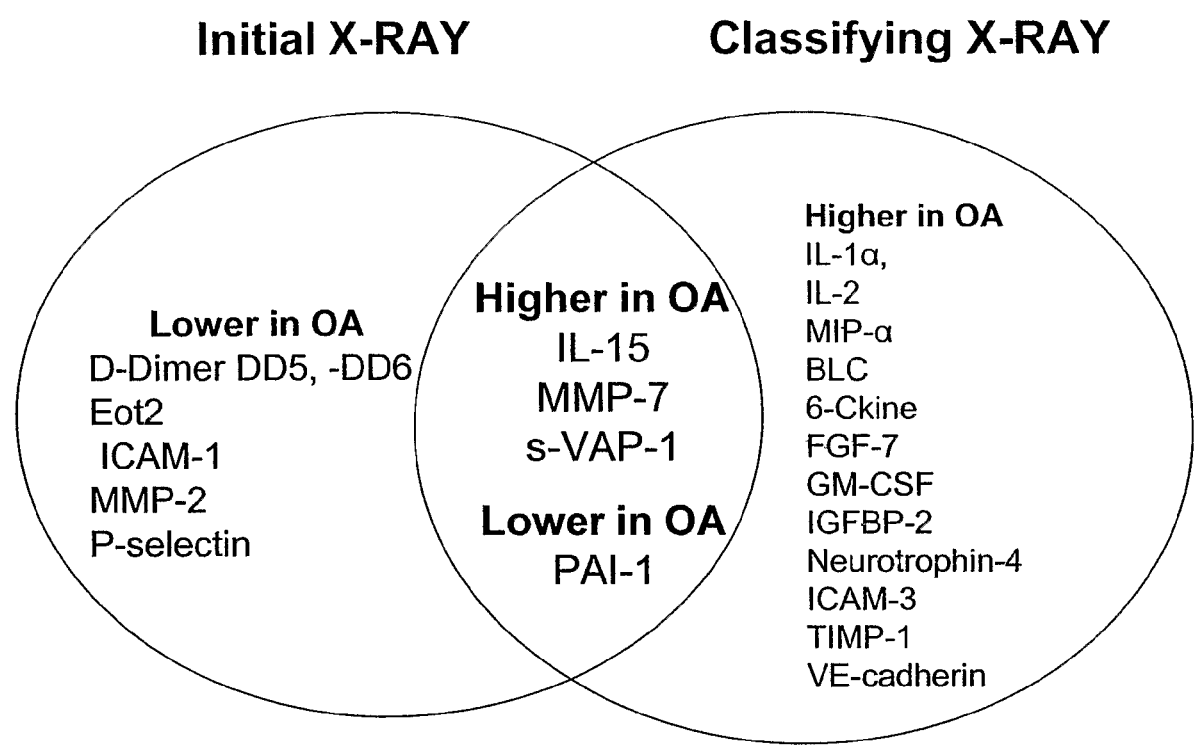
FIG. 5 is a Ven diagram showing proteins identified using mixed model ANOVA and significant analysis of microarray (SAM) analysis wherein expression was changed before the development of OA and those whose expression was changed when OA was present.

To further cross-validate the results obtained by ANOVA and SAM, a principal component analysis (PCA) was conducted based on the correlation matrix of proteins identified as differentially expressed. PCA was conducted on pooled data from all the age groups, as well as by age groups (22-50, 51-69 and 70-92 years), to seek variation patterns among different ages (only the combined age PCA analyses are shown in FIG. 5). In addition, for each protein, the averaged Z-score of the expression values was plotted against each age group.

Decision trees were constructed assessing the extent to which differentially expressed proteins discriminated OA from non-OA participants. For the cross-validation of prediction results, multiple classification processes were performed on two data sets randomly constructed, each time from the entire protein expression data. The first data set, consisting of 70% of the total data, was used as the training data set, and the other data set, the remaining 30% data, was used for the data predictions and verification process. All the analyses were performed on samples obtained at the time of the classifying X-ray and time points prior to that visit separately, using commercial software Partek and Insightful Miner 3.0 and free software Bioconductor R package (Gentleman et al. *Genome Biol.* 5:R80, 2004).

A total of 216 serum samples were analyzed (46 samples obtained over 2 visits from 21 participants classified as incident knee OA and 170 samples obtained over 3 visits from 66 controls). Only the proteins that were substantially different between cases and controls at one or both time points are discussed (10 at the initial x-ray, 16 at the follow-up x-ray). The z-scores of the proteins that were differentially expressed between cases and controls were depicted in a heat map plots and revealed patterns predictive of OA development in contrast to patterns predictive of remaining free of OA (controls). The differences between OA cases and controls were more dramatic in the younger age groups. Similarly, the z-scores of the patterns associated with OA at the second x-ray were used to classify cases and controls. Comparison of the serum protein expression patterns associated with OA at the two time points indicate that proteins associated with prevalent OA can differ from those predictive of OA development.

The results of the PCA analyses confirm and cross-validate the ANOVA and SAM detection of differentially expressed proteins discussed above. Three principal components accounted for 56.5% total variability (26.3%, 17.9% and 12.3% for the first, second and the third principal components respectively) for the PCA analysis using the 16 differentially expressed proteins between OA and control samples identified at time of x-ray classification. Similarly, three PCs accounted for 57.4% total variability (38.8%, 9.7% and 8.9% for the first, second and the third principal components respectively) for the PCA using the 10 differentially expressed proteins identified at the time of the initial X-ray. Moreover, when a similar PCA was conducted using all 169 proteins, the discrimination between cases and controls was significantly lower and accounted for only 37.0% of total variability (18.8%, 9.9%, and 8.3% for the first, second and third components respectively) at the first time point and 34.1% total variability (14.8%, 10.9%, and 8.4%, respectively, on the top three components) at the second time point. Receiver operator characteristic (ROC) curves were also generated using the recursive decision tree classification (Zhang et al. *Proc. Natl. Acad. Sci. USA* 98:6730-5, 2001) of the 16 prevalent OA-associated proteins and 10 OA-predictive proteins and confirmed the superior discrimination power of curve using the differentially expressed proteins compared to all 169 proteins. FIGS. 6A-G shows the z-scores of four differentially expressed proteins (IL-15, MMP-7, PAI-1, and sVAP-1) between OA and control samples.

With few exceptions, the specific proteins identified as associated with OA were different at the two time points (FIG. 5). At the time of the initial x-ray, subsequent development of OA was significantly associated with lower expression of matrix metalloproteinase (MMP)-2, D-dimers DD5 and DD6, eotaxin-2, intracellular adhesion molecule (ICAM-1), and P-selectin, plasminogen activator inhibitor (PAI)-1, and greater expression of MMP-7, soluble vascular adhesion protein (VAP)-1, and interleukin (IL)-15. Therefore, changes in serum proteins accompany knee and hand osteoarthritis (OA), which can be detected years before the OA becomes radiographically evident. At the time of the classifying x-ray, prevalent OA was associated with overexpression of B-lymphocyte chemokine (BLC), 6-chemokine (Ckine), macrophage inhibitory protein (MIP)-1α, IL-1α, IL-2, IL-15, fibroblast growth factor (FGF)-7, granulocyte macrophage colony stimulating factor (GM-CSF), MMP-7, neurotrophin-4 (NT4), ICAM-3, VAP-1, and vascular endothelial (VE)-cadherin and insulin-like growth factor binding protein (IGFBP)-2. These sixteen proteins were differentially expressed in participants with radiographic knee and hand OA compared to age-, gender-, and BMI-matched controls without evidence of radiographic knee or hand OA. IL-15, MMP-7, sVAP-1 and PAI-1 were differentially expressed between the two groups at both time points (FIG. 5). IL-15, MMP-7 and VAP-1 were all higher in association with OA at both time points. In contrast, PAI-I expression was lower in association with OA at both time points.

A summary of the results is presented in FIG. 5. Proteins listed on the left are those whose activity was altered prior to development of OA, and thus can be used to predict the risk of a subject to develop OA in the future. Proteins on the right are those whose activity was altered during established OA, and thus can be used to diagnose or monitor OA progression. Proteins listed in the center are those whose activity was altered before and after development of OA, and thus can be used to predict the risk of a subject to develop OA in the future, diagnose, monitor OA progression, determine OA severity, or combinations thereof.

Figure 7A:
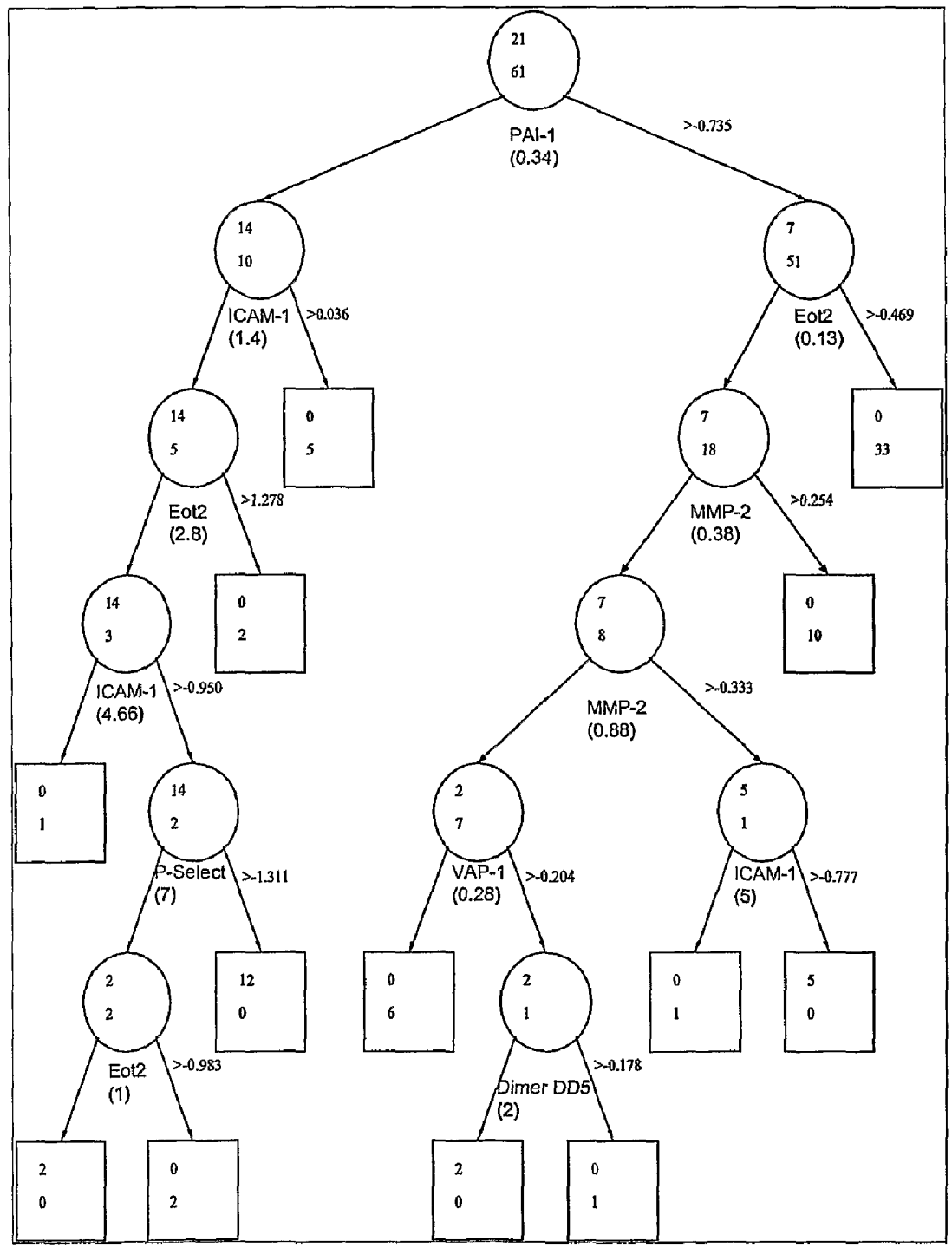
FIGS. 7A and 7B are schematic diagrams showing a classification tree using differentially expressed proteins at the initial and classifying x-ray visits. Recursive regression tree classification of OA and control samples based on protein expression observed at the time of the initial x-ray or earlier (A), and at the time of the classifying x-ray (B). Beside each protein appears the threshold z-score used to classify samples. The odds ratios associated with each protein appear in the brackets. Two numbers are displayed on each node (depicted as circle or square): the number of samples classified as OA by that protein is shown on the top and the number of participants classified as controls is shown on the bottom. The misclassification error rate was 0.06098 for (A), and 0.07059 for (B).
Figure 7B:
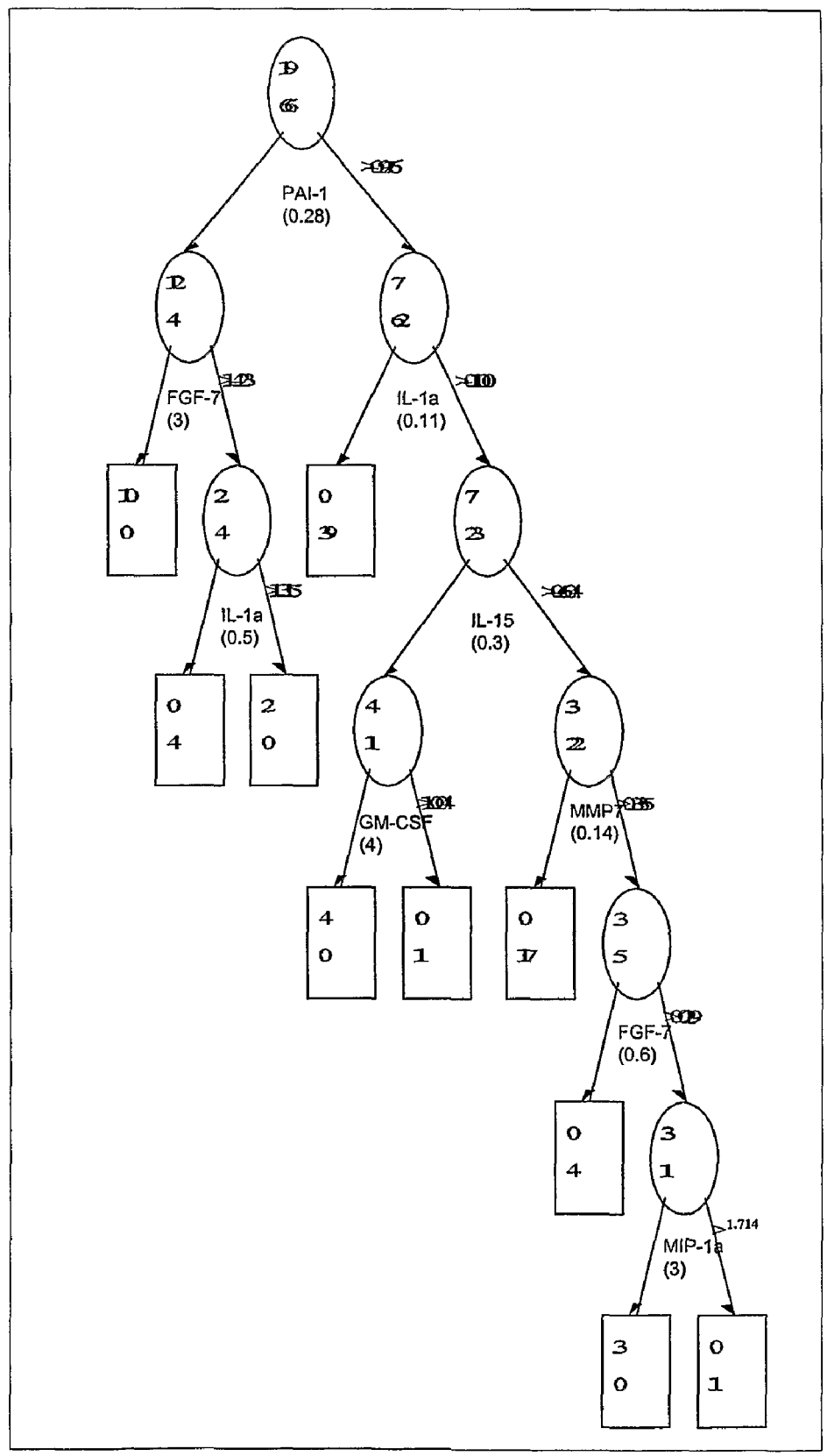

Using recursive partitioning (Zhang et al. *Proc. Natl. Acad. Sci. USA* 98:6730-5, 2001) the relationship between the differentially expressed proteins and their ability to discriminate cases from controls using z-score thresholds was determined. The misclassification error rate was 0.06098 for the 10 differentially expressed proteins at the initial x-ray (FIG. 7A), and 0.07059 for the 16 differentially expressed proteins identified at the classifying x-ray visit (FIG. 7B). Individual proteins were entered step-by-step. Both FIGS. 7A and 7B illustrate that the value of a given protein in classifying participants as cases or controls can differ depending upon the visit (such as PAI-1), and can also be influenced by the expression and level of other expressed proteins (such as ICAM-1).

Therefore, sixteen proteins had differential protein activity associated with OA compared to controls. Four proteins (MMP-7, IL-15, PAI-1 and sVAP-1) were also differentially expressed in samples obtained 10 years earlier. These 16 proteins can therefore be used to diagnose or confirm diagnosis of OA, to determine severity of OA or to monitor progression of OA, or combinations thereof. Six additional proteins (MMP-2, DDimers DD5 and DD6, ICAM-1, P-selectin, and EoT-2) were only associated with subsequent OA development and not with established OA. These 10 proteins, alone or in combination with one or more of MMP-7, IL-15, PAI-1 and sVAP-1, can therefore be used to determine if a subject has an increased risk of developing OA in the future, to monitor progression of OA, or combinations thereof. For example, detection of elevated concentrations of MMP-7, s-VAP1 and IL-15, and lower concentrations of PAI-1 can indicate increased risk of developing OA, for example up to 10 years prior to radiographic classification. In some examples, protein clusters may improve classification accuracy between cases and controls beyond that achieved using single proteins.

In summary, changes in serum proteins involved in matrix degradation, cellular activation and inflammation accompany early OA development and can precede radiographic detection by several years.

Without wishing to be bound to a particular theory, the differentially expressed proteins identified at the time of the normal initial x-rays (DD5, DD6, EoT2, ICAM-1, MMP-2, P-selectin, IL-15, MMP-7, sVAP, and PAI-1), may contribute to OA by initiating extracellular matrix degradation or by chemo attracting inflammatory cells capable of producing cytokines and chemokines that further amplify this degradative process. The MMPs detected in higher concentrations in OA samples (such as MMP-2 and MMP-7) may be produced by fibroblasts, synovial cells and chondrocytes upon exposure to IL-1 and TNF-α that cause cartilage degradation that is considered the hallmark of OA. Unlike MMP-7, MMP-2 is constitutively expressed by normal and osteoarthritic articular chondrocytes (Duerr et al., *Clin. Exp. Rheumatol.* 22:603-8, 2004). Therefore, the decreased levels of MMP-2 observed at the time of the initial x-ray might reflect insufficient turnover required for cartilage remodeling and health maintenance. The lower concentrations of plasminogen activating inhibitor-1 (PAI-1) observed with OA may contribute to OA development by disinhibiting plasmin-mediated matrix degradation of bone and cartilage or by allowing persistence of joint inflammation. The fibrinolytic factors, ICAM-1 and VCAM-1 may be involved in the adhesion of osteoclasts and consequently may stimulate the production of matrix and bone resorbing cytokine. Surprisingly, low rather than high ICAM-1 and P-selectin, two molecules often found elevated in inflammatory conditions (Cush et al. *Arthritis Rheum.* 36:1098-102, 1993), were found to be predictive of OA development.

In addition to the extracellular matrix-relevant (MMP-7 and PAI-1) and inflammatory proteins (sVAP-1, IL-15) that were also differentially expressed at the initial time point, the proteins specifically associated with prevalent OA fall under the broad categories of inflammatory mediators (IL-1α, IL-2, MIP-1α, 6Ckine, BLC), adhesion molecules (VE-cadherin, ICAM-3), tissue metalloproteinase inhibitors (TIMP-1) and growth factors (IGFBP-2, FGF-7, GM-CSF). The association of these growth factors with OA together with mediators of extracellular matrix degradation (MMP-7 and PAI-1) indicates that they are markers of attempted repair.

These results also indicate that OA is neither purely degenerative nor limited to cartilage. That elevated concentrations of MMP-7, IL-15 and s-VAP and low concentrations of PAI-1 observed in OA samples obtained at both pre-classification and classification time points indicates that these might mediate disease initiating as well as sustaining processes. The changes may reflect genetically encoded differences that predispose a subject to developing OA. Additionally, except for these four proteins, the set of proteins associated with OA at the time of the initial x-ray (see FIG. 5) was not differentially expressed at the time of the second x-ray and vice-versa, supports the idea that these protein profiles are responsive to change over time and that the mediators of initiating events are distinct from those that sustain the disease.

EXAMPLE 7

Differential Activity Associated with the Presence of OA

This example describes particular changes in protein levels that are associated with the presence of OA. Although particular OA risk molecules are listed in this example, one skilled in the art will appreciated that other molecules can be used based on the teachings in this disclosure. For example, the particular OA risk-associated molecules can be used in combination with other OA risk-associated molecules, or subcombinations of the OA risk-associated molecules can be used (such as at least 4, at least 5, at least 6, at least 7, at least 8, at least 9, at least 10, at least 12, at least 13, at least 14, at least 15, at least 16, or at least 17 of the molecules listed below) alone or in combination with other OA risk-associated molecules.

In particular examples, detecting differential activity includes detecting differences in protein levels (such as an increase, decrease, or both). Alternatively, detecting differential activity includes detecting differences in nucleic acid levels (such as an increase, decrease, or both). The method can further include determining the magnitude of the difference in activity, wherein the magnitude of the change is associated with the presence of OA).

Particular examples of OA risk-related molecules that are differentially expressed in association with OA, and their direction of change (upregulated or downregulated), and the magnitude of the change (as expressed as a fold change) are provided in Tables 10-11.

TABLE 10

Exemplary patterns of expression associated with osteoarthritis

| OA risk-associated molecule | Change in Expression | Magnitude of the change |
|---|---|---|
| IL-15 | upregulated | at least 4-fold; z-value significantly greater in OA samples than controls at a p < 0.05 |
| MMP-7 | upregulated | at least 4-fold; z-value significantly greater in OA samples than controls at a p < 0.05 |
| sVAP-1 | upregulated | at least 4-fold; z-value significantly greater in OA samples than controls at a p < 0.05 |
| PAI-1 | down-regulated | at least 4-fold; z-value significantly lower in OA samples than controls at a p < 0.05 |
| IL-1 α | upregulated | at least 4-fold; z-value significantly greater in OA samples than controls at a p < 0.05 |
| IL-2 | upregulated | at least 4-fold; z-value significantly greater in OA samples than controls at a p < 0.05 |
| MIP-α | upregulated | at least 4-fold; z-value significantly greater in OA samples than controls at a p < 0.05 |
| BLC | upregulated | at least 4-fold; z-value significantly greater in OA samples than controls at a p < 0.05 |
| 6-Ckine | upregulated | at least 4-fold; z-value significantly greater in OA samples than controls at a p < 0.05 |
| FGF-7 | upregulated | at least 4-fold; z-value significantly greater in OA samples than controls at a p < 0.05 |
| GM-CSF | upregulated | at least 4-fold; z-value significantly greater in OA samples than controls at a p < 0.05 |
| IGFBP-2 | upregulated | at least 4-fold; z-value significantly greater in OA samples than controls at a p < 0.05 |
| NT 4 | upregulated | at least 4-fold; z-value significantly greater in OA samples than controls at a p < 0.05 |
| ICAM-3 | upregulated | at least 4-fold; z-value significantly greater in OA samples than controls at a p < 0.05 |
| TIMP-1 | upregulated | at least 4-fold; z-value significantly greater in OA samples than controls at a p < 0.05 |
| VE-cadherin | upregulated | at least 4-fold; z-value significantly greater in OA samples than controls at a p < 0.05 |

Therefore, IL-15, MMP-7, sVAP-1, IL-1α, IL-2, MIP-1α, BLC, 6-Ckine, FGF-7, GM-CSF, IGFBP-2, NT4, ICAM-3, TIMP-1 and VE-cadherin each had a signal intensity that was at least 4-fold greater than background with z-values that were significantly greater in OA samples than controls at a $p<0.05$. Z-values that were above the mean were considered upregulated, and z-values less than the mean were considered downregulated. That is, IL-15, MMP-7, VAP-1, IL-1α, IL-2, MIP-1α, BLC, 6-Ckine, FGF-7, GM-CSF, IGFBP-2, NT4, ICAM-3, TIMP-1 and VE-cadherin are upregulated by an amount associated with OA, for example at least 4-fold greater than background, and z-values significantly different between OA and control samples at the $p<0.05$ level. In addition, PAI-1 signal intensity was at least 4-fold greater than background, but with a z-value that was significantly lower in OA samples than controls at the $p<0.05$ level, indicating that it was downregulated. That is, PAI-1 is downregulated by an amount associated with OA.

One example of a pattern of expression of proteins that can be associated with OA is upregulation of IL-15, MMP-7, and sVAP-1, wherein each has a signal intensity that is at least 4-fold greater than background with z-values that are significantly greater in OA samples than controls at a $p<0.05$.

Another example of a pattern of expression of proteins that can be associated with OA is as upregulation of IL-15, MMP-7, and sVAP-1, and downregulation of PAI-1, for example wherein each has a signal intensity that is at least 4-fold greater than background with z-values that are significantly greater (IL-15, MMP-7, and sVAP-1) or lower (PAI-1) in OA samples than controls at a $p<0.05$.

Yet another example of a pattern of expression of proteins that can be associated with OA is upregulation of IL-1α, IL-2, MIP-1α, BLC, 6-Ckine, FGF-7, GM-CSF, IGFBP-2, NT4, ICAM-3, TIMP-1 and VE-cadherin, wherein each has a signal intensity that is at least 4-fold greater than background with z-values that are significantly greater in OA samples than controls at a $p<0.05$.

Still another particular example of a pattern of expression of proteins that can be associated with OA is upregulation of IL-15, IL-1α, IL-2, MIP-1α, BLC, 6-Ckine, FGF-7, GM-CSF, IGFBP-2, NT4, ICAM-3, TIMP-1 and VE-cadherin, wherein each has a signal intensity that is at least 4-fold greater than background with z-values that are significantly greater in OA samples than controls at a $p<0.05$.

Another example of a pattern of expression of proteins that can be associated with OA is as upregulation of sVAP-1, IL-1α, IL-2, MIP-1α, BLC, 6-Ckine, FGF-7, GM-CSF, IGFBP-2, NT4, ICAM-3, TIMP-1 and VE-cadherin, for example wherein each has a signal intensity that is at least 4-fold greater than background with z-values that are significantly greater in OA samples than controls at a $p<0.05$.

Another example of a pattern of expression of proteins that can be associated with OA is as upregulation of IL-15, MMP-7, sVAP-1, IL-1α, IL-2, MIP-1α, BLC, 6-Ckine, FGF-7, GM-CSF, IGFBP-2, NT4, ICAM-3, TIMP-1 and VE-cadherin, and downregulation of PAI-1, for example wherein each has a signal intensity that is at least 4-fold greater than background with z-values that are significantly greater (IL-15, MMP-7, sVAP-1, IL-1α, IL-2, MIP-1α, BLC, 6-Ckine, FGF-7, GM-CSF, IGFBP-2, NT4, ICAM-3, TIMP-1 and VE-cadherin) or lower (PAI-1) in OA samples than controls at a $p<0.05$.

TABLE 11

Exemplary patterns of expression associated with osteoarthritis

| OA risk-associated molecule | Change in Expression | Magnitude of the change |
|---|---|---|
| MIP-1β | Upregulated | At least 4-fold; z-value significantly greater in OA samples than controls at a p < 0.05 |
| MIP-1δ | Downregulated | At least 4-fold; z-value significantly lower in OA samples than controls at a p < 0.05 |
| UPAR | Upregulated | At least 4-fold; z-value significantly greater in OA samples than controls at a p < 0.05 |

TABLE 11-continued

Exemplary patterns of expression associated with osteoarthritis

| OA risk-associated molecule | Change in Expression | Magnitude of the change |
|---|---|---|
| VCAM-1 | Upregulated | At least 4-fold; z-value significantly greater in OA samples than controls at a p < 0.05 |
| 6-Ckine | Upregulated | At least 4-fold; z-value significantly greater in OA samples than controls at a p < 0.05 |
| IL-2 | Upregulated | At least 4-fold; z-value significantly greater in OA samples than controls at a p < 0.05 |
| Eot2 | Downregulated | At least 4-fold; z-value significantly lower in OA samples than controls at a p < 0.05 |
| IGFBP-4 | Upregulated | At least 4-fold; z-value significantly greater in OA samples than controls at a p < 0.05 |
| ICAM-3 | Upregulated | At least 4-fold; z-value significantly greater in OA samples than controls at a p < 0.05 |
| MIG | Upregulated | At least 4-fold; z-value significantly greater in OA samples than controls at a p < 0.05 |
| MMP-7 | Upregulated | At least 4-fold; z-value significantly greater in OA samples than controls at a p < 0.05 |
| MPIF-1 | Upregulated | At least 4-fold; z-value significantly greater in OA samples than controls at a p < 0.05 |
| TARC | downregulated | At least 4-fold; z-value significantly lower in OA samples than controls at a p < 0.05 |
| TGF-b RIII | Upregulated | At least 4-fold; z-value significantly greater in OA samples than controls at a p < 0.05 |

Therefore, MIP-1β, UPAR, VCAM-1, 6-Ckine, IL-2, IGFBP-4, ICAM-3, MIG, MMP-7, MPIF-1, and TGF-b RIII each have a signal intensity that was at least 4-fold greater than background with z-values that were significantly greater in OA samples than controls at a p<0.05. That is, MIP-1β, UPAR, VCAM-1, 6-Ckine, IL-2, IGFBP-4, ICAM-3, MIG, MMP-7, MPIF-1, and TGF-β RIII are upregulated by an amount associated with OA, for example at least 4-fold greater than background, and z-values significantly different between OA and control samples at the p<0.05 level. In addition, MIP-1δ, Eot2, and TARC each had a signal intensity was at least 4-fold greater than background, and with z-values significantly lower in OA samples than control samples at the p<0.05 level. That is, MIP-1δ, Eot2, and TARC are downregulated by an amount associated with OA, for example at least 4-fold greater than background, and z-values significantly different between OA and control samples at the p<0.05 level.

One example of a pattern of expression of proteins that can be associated with OA is upregulation of MIP-1β, UPAR, and VCAM-1, wherein each has a signal intensity that is at least 4-fold greater than background with z-values that are significantly greater in OA samples than controls at a p<0.05.

Another example of a pattern of expression of proteins that can be associated with OA is as upregulation of MIP-1β, UPAR, VCAM-1, 6-Ckine, ICAM-3, and TGF-β RIII and downregulation of MIP-1δ, wherein each has a signal intensity that is at least 4-fold greater than background with z-values that are significantly greater (MIP-1β, UPAR, VCAM-1, 6-Ckine, ICAM-3, and TGF-β RIII) or lower (MIP-1δ) in OA samples than controls at a p<0.05.

Yet another example of a pattern of expression of proteins that can be associated with OA is upregulation of MIP-1β, UPAR, VCAM-1, 6-Ckine, IL-2, IGFBP-4, ICAM-3, MIG, MMP-7, MPIF-1, and TGF-β RIII, wherein each has a signal intensity that is at least 4-fold greater than background with z-values that are significantly greater in OA samples than controls at a p<0.05.

Another example of a pattern of expression of proteins that can be associated with OA is as upregulation of MIP-1β, UPAR, VCAM-1, 6-Ckine, IL-2, IGFBP-4, ICAM-3, MIG, MMP-7, MPIF-1, and TGF-β RIII, and downregulation of MMP-1δ, Eot2, and TARC, wherein each has a signal intensity that is at least 4-fold greater than background with z-values that are significantly greater (MIP-1β, UPAR, VCAM-1, 6-Ckine, IL-2, IGFBP-4, ICAM-3, MIG, MMP-7, MPIF-1, and TGF-β RIII) or lower (MIP-1δ, Eot2, and TARC) in OA samples than controls at a p<0.05.

EXAMPLE 8

Differential Activity Associated with Risk of Developing OA

This example describes particular changes in protein levels that are associated with an increased risk of developing OA. Although particular OA risk molecules are listed in this example, one skilled in the art will appreciated that other molecules can be used based on the teachings in this disclosure. For example, the particular OA risk-associated molecules can be used in combination with other OA risk-associated molecules, or subcombinations of the OA risk-associated molecules can be used (such as at least 4, at least 5, at least 6, at least 7, at least 8, at least 9, at least 10, at least 12, at least 13, at least 14, at least 15, at least 16, at least 17, at least 18, at least 19, at least 20, at least 21, or at least 22, of the molecules listed below) alone or in combination with other OA risk-associated molecules.

In particular examples, detecting differential activity includes detecting differences in protein levels (such as an increase, decrease, or both). Alternatively, detecting differential activity includes detecting differences in nucleic acid levels (such as an increase, decrease, or both). The method can further include determining the magnitude of the differ-ence in activity, wherein the magnitude of the change is associated with the presence of OA).

Particular examples of OA risk-related molecules that are differentially expressed in association with an elevated risk of developing OA (such as developing OA in at least 5 years, at least 10 years, at least 15 years, at least 20 years, or at least 30 years), and their direction of change (upregulated or down-regulated), and the magnitude of the change (as expressed as a fold change) are provided in Tables 12-13.

TABLE 12

Exemplary patterns of expression associated with elevated risk of developing OA

| OA risk-associated molecule | Change in Expression | Magnitude of the change |
|---|---|---|
| IL-15 | upregulated | at least 4-fold; z-value significantly greater in OA samples than controls at a p < 0.05 |
| MMP-7 | upregulated | at least 4-fold; z-value significantly greater in OA samples than controls at a p < 0.05 |
| sVAP-1 | upregulated | at least 4-fold; z-value significantly greater in OA samples than controls at a p < 0.05 |
| PAI-1 | downregulated | at least 4-fold; z-value significantly lower in OA samples than controls at a p < 0.05 |
| DD5 | downregulated | at least 4-fold; z-value significantly lower in OA samples than controls at a p < 0.05 |
| DD6 | downregulated | at least 4-fold; z-value significantly lower in OA samples than controls at a p < 0.05 |
| EoT2 | downregulated | at least 4-fold; z-value significantly lower in OA samples than controls at a p < 0.05 |
| ICAM-1 | downregulated | at least 4-fold; z-value significantly lower in OA samples than controls at a p < 0.05 |
| MMP-2 | downregulated | at least 4-fold; z-value significantly lower in OA samples than controls at a p < 0.05 |

TABLE 12-continued

Exemplary patterns of expression associated with elevated risk of developing OA

| OA risk-associated molecule | Change in Expression | Magnitude of the change |
|---|---|---|
| P-selectin | downregulated | at least 4-fold; z-value significantly lower in OA samples than controls at a p < 0.05 |

Therefore, IL-15, MMP-7, and sVAP-1 each had a signal intensity that was at least 4-fold greater than background with z-values that were significantly greater in OA samples than controls at a p<0.05. That is, IL-15, MMP-7, and sVAP-1 are upregulated by an amount associated with increased risk of developing OA in the future, for example at least 4-fold greater than background, and z-values significantly different between OA and control samples at the p<0.05 level. In addition, PAI-1, DD5, DD6, EoT2, ICAM-1, MMP-2 and P-selectin each had a signal intensity that was at least 4-fold greater than background, but with a z-value that was significantly lower in OA samples than controls at the p<0.05 level, indicating that it was downregulated. That is, PAI-1, DD5, DD6, EoT2, ICAM-1, MMP-2 and P-selectin are downregulated by an amount associated with increased risk of developing OA in the future, for example at least 4-fold greater than background, and z-values significantly different between OA and control samples at the p<0.05 level.

One example of a pattern of expression of proteins that can be associated with increased risk of developing OA in the future is upregulation of IL-15, MMP-7, and sVAP-1, wherein each has a signal intensity that is at least 4-fold greater than background with z-values that are significantly greater in OA samples than controls at a p<0.05.

Another example of a pattern of expression of proteins that can be associated with increased risk of developing OA is as upregulation of IL-15, MMP-7, and sVAP-1, and downregulation of PAI-1, for example wherein each has a signal intensity that is at least 4-fold greater than background with z-values that are significantly greater (IL-15, MMP-7, and sVAP-1) or lower (PAI-1) in OA samples than controls at a p<0.05.

Yet another example of a pattern of expression of proteins that can be associated with increased risk of developing OA is downregulation of DD5, DD6, EoT2, ICAM-1, MMP-2 and P-selectin, wherein each has a signal intensity that is at least 4-fold greater than background with z-values that are significantly lower in OA samples than controls at a p<0.05.

Still another particular example of a pattern of expression of proteins that can be associated with OA is upregulation of IL-15, IL-1α, IL-2, MIP-1α, BLC, 6-Ckine, FGF-7, GM-CSF, IGFBP-2, NT4, ICAM-3, TIMP-1 and VE-cadherin, wherein each has a signal intensity that is at least 4-fold greater than background with z-values that are significantly greater in OA samples than controls at a p<0.05.

Another example of a pattern of expression of proteins that can be associated with OA is as upregulation of IL-15 and downregulation of DD5, DD6, EoT2, ICAM-1, MMP-2 and P-selectin, for example wherein each has a signal intensity that is at least 4-fold greater than background with z-values that are significantly lower in OA samples than controls at a p<0.05.

Another example of a pattern of expression of proteins that can be associated with OA is as upregulation of sVAP and downregulation of DD5, DD6, EoT2, ICAM-1, MMP-2 and P-selectin, for example wherein each has a signal intensity that is at least 4-fold greater than background with z-values that are significantly greater (sVAP) or lower (DD5, DD6, EoT2, ICAM-1, MMP-2 and P-selectin) in OA samples than controls at a p<0.05.

Another example of a pattern of expression of proteins that can be associated with OA is as upregulation of IL-15 and downregulation of DD5, DD6, EoT2, ICAM-1, MMP-2, PAI-1 and P-selectin, for example wherein each has a signal intensity that is at least 4-fold greater than background with z-values that are significantly greater (IL-15) or lower (DD5, DD6, EoT2, ICAM-1, MMP-2, PAI-1 and P-selectin) in OA samples than controls at a p<0.05.

Another example of a pattern of expression of proteins that can be associated with OA is as upregulation of sVAP and downregulation of DD5, DD6, EoT2, ICAM-1, MMP-2, PAI-1 and P-selectin, for example wherein each has a signal intensity that is at least 4-fold greater than background with z-values that are significantly greater (sVAP) or lower (DD5, DD6, EoT2, ICAM-1, MMP-2, PAI-1 and P-selectin) in OA samples than controls at a p<0.05.

TABLE 13

Exemplary patterns of expression associated with increased risk of developing OA

| OA risk-associated molecule | Change in Expression | Magnitude of the change |
|---|---|---|
| MIP-1β | Upregulated | At least 4-fold; z-value significantly greater in OA samples than controls at a p < 0.05 |
| MIP-1δ | Downregulated | At least 4-fold; z-value significantly lower in OA samples than controls at a p < 0.05 |
| UPAR | Upregulated | At least 4-fold; z-value significantly greater in OA samples than controls at a p < 0.05 |
| VCAM-1 | Upregulated | At least 4-fold; z-value significantly greater in OA samples than controls at a p < 0.05 |
| 6-Ckine | Upregulated | At least 4-fold; z-value significantly greater in OA samples than controls at a p < 0.05 |
| ICAM-3 | Upregulated | At least 4-fold; z-value significantly greater in OA samples than controls at a p < 0.05 |
| TGF-β RIII | Upregulated | At least 4-fold; z-value significantly greater in OA samples than controls at a p < 0.05 |
| BDNF | Upregulated | At least 4-fold; z-value significantly greater in OA samples than controls at a p < 0.05 |
| EGF | Downregulated | At least 4-fold; z-value significantly lower in OA samples than controls at a p < 0.05 |
| HCC1 | Upregulated | At least 4-fold; z-value significantly greater in OA samples than controls at a p < 0.05 |
| leptin | Upregulated | At least 4-fold; z-value significantly greater in OA samples than controls at a p < 0.05 |
| MMP-7 | Upregulated | At least 4-fold; z-value significantly greater in OA samples than controls at a p < 0.05 |
| prolactin | Downregulated | At least 4-fold; z-value significantly lower in OA samples than controls at a p < 0.05 |

Therefore, MIP-1β, UPAR, VCAM-1, 6-Ckine, ICAM-3, TGF-β RIII, IL-2, HCC, leptin, MMP-7 and BDNF each had a signal intensity that was at least 4-fold greater than background with z-values that were significantly greater in OA samples than controls at a p<0.05. That is, MIP-1β, UPAR, VCAM-1, 6-Ckine, ICAM-3, TGF-β RIII, IL-2, HCC, leptin, MMP-7 and BDNF are upregulated by an amount associated with increased risk of developing OA, for example at least 4-fold greater than background, and z-values significantly different between OA and control samples at the p<0.05 level. In addition, MIP-1δ, prolactin and EGF each had a signal intensity was at least 4-fold greater than background, but with a z-value that was significantly lower in OA samples than controls at the p<0.05 level. That is, MIP-1δ, prolactin and EGF are downregulated by an amount associated with increased risk of developing OA, for example at least 4-fold greater than background, and z-values significantly different between OA and control samples at the $p<0.05$ level.

One example of a pattern of expression of proteins that can be associated with increased risk of developing OA is upregulation of MIP-1β, UPAR, and VCAM-1, wherein each has a signal intensity that is at least 4-fold greater than background with z-values that are significantly greater in OA samples than controls at a $p<0.05$.

Another example of a pattern of expression of proteins that can be associated with increased risk of developing OA is as upregulation of MIP-1, UPAR, VCAM-1, 6-Ckine, ICAM-3, and TGF-β RIII and downregulation of MIP-1δ, for example wherein each has a signal intensity that is at least 4-fold greater than background with z-values that are significantly greater (MIP-1β, UPAR, VCAM-1, 6-Ckine, ICAM-3, and TGF-β RIII) or lower (MIP-1δ) in OA samples than controls at a $p<0.05$.

Yet another example of a pattern of expression of proteins that can be associated with increased risk of developing OA is upregulation of MIP-1β, UPAR, VCAM-1, 6-Ckine, ICAM-3, TGF-β RIII, IL-2, HCC, leptin, MMP-7 and BDNF wherein each has a signal intensity that is at least 4-fold greater than background with z-values that are significantly greater in OA samples than controls at a $p<0.05$.

Another example of a pattern of expression of proteins that can be associated with increased risk of developing OA is as upregulation of MIP-1β, UPAR, VCAM-1, 6-Ckine, ICAM-3, TGF-β RIII, IL-2, HCC, leptin, MMP-7 and BDNF and downregulation of MIP-1δ, prolactin, and EGF, for example wherein each has a signal intensity that is at least 4-fold greater than background with z-values that are significantly greater (MIP-1β, UPAR, VCAM-1, 6-Ckine, ICAM-3, TGF-β RIII, IL-2, HCC, leptin, MMP-7 and BDNF) or lower (MIP-1δ, prolactin, and EGF) in OA samples than controls at a $p<0.05$.

EXAMPLE 9

Diagnosing OA

This example describes methods that can be used to diagnose OA in a subject, or confirm a previous diagnosis of OA, for example in a human or veterinary subject. Although particular combinations of OA risk-associated molecules are disclosed for performing such analysis, one skilled in the art will understand that other combinations can be used, such as combinations that include all or subcombinations of the disclosed OA-risk associated molecules.

A sample obtained from the subject (such as a serum sample) can be analyzed using the disclosed methods. In one example, the subject has generalized OA (for example OA of the hand and knee), as compared to OA secondary to other processes (such as trauma). In some examples, the subject has one or more symptoms associated with OA, such as pain and swelling of the affected joint.

In particular examples, the assay can be performed prior to performing any imaging tests that are routinely performed to find anatomic evidence of OA. For example, it is often difficult for imaging modalities (such as x-ray and MRI) to detect early stages of OA. Hence the assay described herein in particular examples is able to detect OA even before definitive imaging evidence of the OA is known.

In certain example, anti-OA therapy is given to the subject once the results of the differential activity assay are known if the assay indicates that the subject has OA.

A sample obtained or derived from the test subject, such as a human or veterinary subject, is manipulated as needed for the detection method used. Although this example describes preparation of a serum sample for analyzing protein expression, one skilled in the art will appreciate that other biological samples can be used (such as urine or synovial fluid), and other methods of analyzing expression can be used. Serum can be obtained from a blood sample using routine methods. The serum is centrifuged to remove particulate matter and mixed with 0.25 mg/ml Heteroblock (Omega), 0.25 mg/ml IIR (Bioreclamation) and 0.1% Tween-20.

The array is blocked to reduce non-specific binding prior to applying the sample. For example the array can be treated with Seablock (Pierce Chemical Co.), diluted 1:1 with PBS for 1 hour at 37° C. in a humidified chamber. Following removal of the blocking solution, arrays are washed twice with 1×PBS/0.5% Brij 35 prior to application of sample. The treated serum (such as 10-50 µl, for example 20 µl) is applied to an array that includes antibodies that recognize at least four OA-risk associated proteins under conditions that permit the formation of specific protein:antibody complexes (such as 30-120 minutes at 37° C., for example 30 minutes at 37° C.). Unbound proteins are removed by washing the array, for example with PBX/0.5% Brj-35.

The array can include antibodies that recognize one or more OA-risk associated proteins (such as two or more, three or more, or four or more OA-risk associated proteins) as well as other proteins that serve as controls. In a specific example, the array includes antibodies that recognize at least interleukin-15 (IL-15), soluble vascular adhesion protein 1 (sVAP-1), metalloproteinase-7 (MMP-7), plasminogen activating inhibitor-1 (PAI-1), interleukin 1 alpha (IL-1α), IL-2, macrophage inhibitory protein MIP)-1α, B-lymphocyte chemokine (BLC), 6-chemokine (Ckine), fibroblast growth factor (FGF)-7, granulocyte macrophage colony stimulating factor (GM-CSF), insulin-like growth factor binding protein (IGFBP)-2, neurotrophin-4 (NT4), ICAM-3, vascular endothelial (VE)-cadherin, and tissue inhibitors of metalloproteinases 1 (TIMP-1). In another specific example, the array includes antibodies that recognize at least macrophage inflammatory protein 1β (MIP-1β), macrophage inflammatory protein 1δ (MIP-1δ), urokinase-type plasminogen activator receptor (UPAR), and vascular cell adhesion molecule-1 (VCAM-1), IL-2, Eot2, IGFBP-4, ICAM-3, monokine induced by interferon γ (MIG), MMP-7, myeloid progenitor inhibitory factor 1 (MPIF-1), TGFβ receptor III (TGF-β RIII), and thymus and activation regulated chemokine (TARC), and can further include antibodies that recognize 6-Ckine. In yet another specific example, the array includes antibodies that recognize at least IL-15, sVAP-1, MMP-7, PAI-1, IL-1α, IL-2, MIP-1α, BLC, 6-Ckine, FGF-7, GM-CSF, IGFBP-2, NT4, ICAM-3, VE-cadherin, TIMP-1, MIP-1β, MIP-1δ, UPAR, VCAM-1, Eot2, IGFBP-4, MIG, MPIF-1, TGF-β RIII, and TARC.

The formed complexes between the proteins in the serum and the antibodies on the array are detected, for example using RCA indirect immunoassay. Secondary biotinylated detector antibodies are incubated with the protein:antibody complexes (for example 0.1 µg/ml Ab in PBS/0.5% Brj-35 for 30-120 minutes at 37° C., such as 30 minutes 37° C.), and bind to captured proteins. Unbound biotinylated detector antibodies are removed by washing as described above.

The array is incubated with universal anti-biotin antibody, which can specifically bind on the biotinylated detector antibodies. The universal anti-biotin antibody is conjugated to primer oligonucleotides that are preannealed to a complementary circular oligonucleotide. Unbound biotinylated detector antibody conjugate is removed by washing as described above.

The RCA reaction is then performed on the array in the presence of DNA polymerase and a detector probe (such as a Cy5-labeled probe) under conditions that permit extension of the 3' ends of the primers around the circles (such as 45 minutes at 37° C.), resulting in ss-RCA products that remain attached to the protein:antibody complex. Particular incubation conditions and concentrations are known in the art (for example see Schweitzer et al., *Nat. Biotechnol.* 20(4):359-65, 2002, herein incorporated by reference).

The arrays are scanned and the mean fluorescence intensity for each protein on the array determined. Background fluorescence intensity can be subtracted from all experimental fluorescence intensity if desired. The intensity for each protein can be compared to a control or reference value. For example, a reference fluorescence signal intensity value can be a value or range of values for the OA-risk associated protein expected when OA is present or not present. A control value can be the mean fluorescence intensity for each OA-risk associated protein obtained from a parallel control sample from a subject having OA, or not having OA. In some examples, the control value represents the value for a subject of the same gender, in the same age range (for example ±2 years, ±5 years or ±10 years), or combinations thereof.

OA-risk associated proteins are considered to be overexpressed or upregulated in a subject if the mean fluorescence intensity for the OA-risk associated protein is significantly increased ($p \leq 0.05$) relative to the reference or control value for an absence of OA, or if the mean fluorescence intensity for the OA-risk associated protein is significantly similar ($p \leq 0.05$) to the reference or control value in the presence of OA. In another example, OA-risk associated proteins are considered to be overexpressed or upregulated in a subject if the mean fluorescence intensity for the OA-risk associated protein is increased by at least 50%, at least 100% or at least 200% relative to the reference or control value for an absence of OA, after subtracting background signal from the intensity value.

OA-risk associated proteins are considered to be underexpressed or downregulated in a subject if the mean fluorescence intensity for the OA-risk associated protein is significantly decreased ($p \leq 0.05$) relative to the reference or control value for an absence of OA, or if the mean fluorescence intensity for the OA-risk associated protein is significantly similar ($p \leq 0.05$) to the reference or control value in the presence of OA. In another example, OA-risk associated proteins are considered to be underexpressed or downregulated in a subject if the mean fluorescence intensity for the OA-risk associated protein is decreased by at least 30%, at least 50% or at least 75% relative to the reference or control value for an absence of OA, after subtracting background signal from the intensity value.

In order for the mean fluorescence intensity to be considered, it is ideally at least 4-fold higher than background.

The presence of a statistically significant difference in the detected amount of at least two, at least three or at least four of the OA-risk associated proteins (such as at least 10, at least 15 or at least 20 of the proteins) indicates that the subject has OA.

EXAMPLE 10

Predicting Risk of Developing OA in the Future

This example describes methods that can be used to determine if a subject has an increased risk of developing OA in the future, for example in a human or veterinary subject. Although particular combinations of OA risk-associated molecules are disclosed for performing such analysis, one skilled in the art will understand that other combinations can be used, such as combinations that include all or subcombinations of the disclosed OA-risk associated molecules.

A sample obtained from the subject (such as a serum sample) can be analyzed using the disclosed methods. In one example, the subject has no other clinical symptoms associated with OA, such as pain and swelling of the affected joint. In particular examples, the assay is performed prior to performing any imaging tests to find anatomic evidence of OA. Because it is often difficult for imaging modalities (such as x-ray and MRI) to detect early stages of OA, this example provides methods for identifying subjects that have a greater likelihood of developing OA, and therefore may require more careful monitoring or treatment.

In certain example, anti-OA therapy is given to the subject once the results of the differential activity assay are known if the assay indicates that the subject has an increased risk of developing OA in the future.

A sample obtained or derived from the test subject, such as a human or veterinary subject, is manipulated as needed for the detection method used. Although this example describes preparation of a serum sample for analyzing protein expression, one skilled in the art will appreciate that other biological samples can be used (such as urine or synovial fluid), and other methods of analyzing expression can be used. Serum can be obtained from a blood sample using routine methods, and prepared as described in Example 9.

The array is blocked and washed, and incubated with the serum sample as described in Example 9. The array can include antibodies that recognize four or more OA-risk associated proteins, as well as other proteins that serve as controls. In a specific example, the array includes antibodies that recognize at least interleukin-15 (IL-15), soluble vascular adhesion protein 1 (sVAP-1), metalloproteinase-7 (MMP-7), plasminogen activating inhibitor-1 (PAI-1), D-dimer 5 (DD5), DD6, eotaxin 2 (Eot2), intercellular adhesion molecule-1 (ICAM-1), MMP-2, and P-selectin. In another specific example, the array includes antibodies that recognize at least macrophage inflammatory protein 1β (MIP-1β), macrophage inflammatory protein 1δ (MIP-1δ), urokinase-type plasminogen activator receptor (UPAR), vascular cell adhesion molecule-1 (VCAM-1), 6-Ckine, ICAM-3, TGF-β RIII, brain-derived neurotrophic factor (BDNF), epidermal growth factor (EGF), hemofiltrate CC chemokine 1 (HCC1), leptin, MMP-7, and prolactin. In yet another specific example, the array includes antibodies that recognize at least IL-15, sVAP-1, MMP-7, PAI-1, DD5, DD6, Eot2, ICAM-1, MMP-2, P-selectin, MIP-1β, MIP-1δ, UPAR, VCAM-1, 6-Ckine, ICAM-3, TGF-β RIII, BDNF, EGF, HCC1, leptin, and prolactin.

The formed complexes between the proteins in the serum and the antibodies on the array are detected, for example using RCA indirect immunoassay as described in Example 9.

The arrays are scanned and the mean fluorescence intensity for each protein on the array determined. Background fluorescence intensity can be subtracted from all experimental fluorescence intensity if desired. The intensity for each protein can be compared to a control or reference value. For example, a reference fluorescence signal intensity value can be a value or range of values for the OA-risk associated protein expected when increased risk of developing OA in the future is present or not present. A control value can be the mean fluorescence intensity for each OA-risk associated protein obtained from a parallel control sample from a subject having known OA risk, or not having OA risk. In some examples, the control value represents the value for a subject of the same gender, in the same age range (for example ±2 years, ±5 years or ±10 years), or combinations thereof.

OA-risk associated proteins are considered to be overexpressed or upregulated in a subject if the mean fluorescence intensity for the OA-risk associated protein is significantly increased ($p<0.05$) relative to the reference or control value for an absence of OA in the future, or if the mean fluorescence intensity for the OA-risk associated protein is significantly similar ($p<0.05$) to the reference or control value in the presence of OA risk in the future. In another example, OA-risk associated proteins are considered to be overexpressed or upregulated in a subject if the mean fluorescence intensity for the OA-risk associated protein is increased by at least 50%, at least 100% or at least 200% relative to the reference or control value for an absence of OA risk in the future, after subtracting background signal from the intensity value.

OA-risk associated proteins are considered to be underexpressed or downregulated in a subject if the mean fluorescence intensity for the OA-risk associated protein is significantly decreased ($p<0.05$) relative to the reference or control value for an absence of OA risk in the future, or if the mean fluorescence intensity for the OA-risk associated protein is significantly similar ($p<0.05$) to the reference or control value in the presence of OA risk in the future. In another example, OA-risk associated proteins are considered to be underexpressed or downregulated in a subject if the mean fluorescence intensity for the OA-risk associated protein is decreased by at least 30%, at least 50% or at least 75% relative to the reference or control value for an absence of OA risk in the future, after subtracting background signal from the intensity value.

In order for the mean fluorescence intensity to be considered, it is ideally at least 4-fold higher than background.

The presence of a statistically significant difference in the detected amount of at least two of the OA-risk associated proteins (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 of the proteins) indicates that the subject has increased risk of developing OA in the future.

EXAMPLE 11

Predicting Severity of Osteoarthritis

This example describes methods that can be used to determine the severity of OA in a subject, or to predict how severe OA will be if it develops in a subject. In some examples, the severity of OA is determined in a subject having OA, such as a subject having generalized OA (for example OA of the hand and knee). In other examples, the prediction of how severe OA will be if it develops in a subject is determined in a subject having no clinical symptoms of OA (such as pain, swelling, and stiffness of the affected joint) but has been shown to have an increased risk of developing OA in the future. The assay can be performed before or following the onset of signs and symptoms associated with OA.

Severity of OA is currently categorized using radiograph results, symptoms, and function of the joint, and cartilage and bone metabolism. The data obtained in Example 3 can be analyzed to determine the proteins that are associated with OA severity and which are predictive of OA disease severity, as shown in Table 14. Inflammatory cytokines and chemokines listed in Tables 8, 10, and 12 can be associated with disease severity, and growth factors listed in Tables 8, 10 and 12 can be associated with radiographic severity.

TABLE 14

Categorization of OA severity.

| SEVERITY CATEGORY | DEFINITIONS WILL BE APPLIED TO THE HANDS, KNEES, HANDS and KNEES together |
|---|---|
| RADIOGRAPHS | Total number of joints with definite OA (KL grade >1) Sum of Kellgren & Lawrence Grades Sum of joint space narrowing grade Sum of osteophyte grade |
| SYMPTOMS | Presence of painful symptoms Extent of painful symptoms (number of painful joints) Distribution of painful symptoms Severity of painful symptoms |
| FUNCTION | Mobility performance (walking speed, chair stand time, knee extensor strength) |
| CARTILAGE & BONE METABOLISM | Urine helicopeptide, pyridinoline cross-links Serum pro-collagen peptide, pyridinoline cross-links, n-telopeptide, additional "biomarkers" |

Using the OA risk associated molecules listed in Tables 8 and 10-13, OA severity can be determined as follows. A sample obtained or derived from the test subject, such as a human or veterinary subject, is manipulated as needed for the detection method used. Although this example describes preparation of a serum sample for analyzing protein expression, one skilled in the art will appreciate that other biological samples can be used (such as urine or synovial fluid), and other methods of analyzing expression can be used. Serum can be obtained, manipulated, and applied to an array (which has been blocked and washed) as described in Example 9.

The array can include antibodies that recognize four or more OA-risk associated proteins, as well as other proteins that serve as controls. In a specific example, the array includes antibodies that recognize at least interleukin-15 (IL-15), soluble vascular adhesion protein 1 (sVAP-1), metalloproteinase-7 (MMP-7), plasminogen activating inhibitor-1 (PAI-1), interleukin 1 alpha (IL-1α), IL-2, macrophage inhibitory protein (MIP)-1α, B-lymphocyte chemokine (BLC), 6-chemokine (Ckine), fibroblast growth factor (FGF)-7, granulocyte macrophage colony stimulating factor (GM-CSF), insulin-like growth factor binding protein (IGFBP)-2, neurotrophin-4 (NT4), ICAM-3, vascular endothelial (VE)-cadherin, and tissue inhibitors of metalloproteinases 1 (TIMP-1). In another specific example, the array includes antibodies that recognize at least macrophage inflammatory protein 1β (MIP-1β), macrophage inflammatory protein 1δ (MIP-1δ), urokinase-type plasminogen activator receptor (UPAR), and vascular cell adhesion molecule-1 (VCAM-1), IL-2, Eot2, IGFBP-4, ICAM-3, monokine induced by interferon γ (MIG), MMP-7, myeloid progenitor inhibitory factor 1 (MPIF-1), TGFβ receptor III (TGF-β RIII), and thymus and activation regulated chemokine (TARC), and can further include antibodies that recognize 6-Ckine.

In a specific example, the array includes antibodies that recognize at least IL-15, sVAP-1, MMP-7, PAI-1, DD5, DD6, Eot2, ICAM-1, MMP-2, P-selectin, IL-1α, IL-2, MIP-1α, BLC, 6-Ckine, FGF-7, GM-CSF, IGFBP-2, NT4, ICAM-3, VE-cadherin, and TIMP-1. In another specific example, the array includes antibodies that recognize at least MIP-1β, MIP-1δ, UPAR, VCAM-1, IL-2, Eot2, IGFBP-4, ICAM-3, MMP-7, MIG, MPIF-1, TGF-β RIII, 6-Ckine, TARC, BDNF, EGF, HCC1, leptin, and prolactin.

In yet another specific example, the array includes antibodies that recognize at least IL-15, sVAP-1, MMP-7, PAI-1, DD5, DD6, Eot2, ICAM-1, MMP-2, P-selectin, MIP-1β, MIP-1δ, UPAR, VCAM-1, BDNF, EGF, HCC1, leptin, prolactin, IL-1α, IL-2, MIP-1α, BLC, 6-Ckine, FGF-7, GM-CSF, IGFBP-2, NT4, ICAM-3, VE-cadherin, TIMP-1, IGFBP-4, MIG, MPIF-1, TGF-β RIII, and TARC.

The formed complexes between the proteins in the serum and the antibodies on the array are detected, for example using RCA indirect immunoassay using the methods described in Example 9.

The arrays are scanned and the mean fluorescence intensity for each protein on the array determined. Background fluorescence intensity can be subtracted from all experimental fluorescence intensity if desired. The intensity for each protein can be compared to a control or reference value. For example, a reference fluorescence signal intensity value can be a value or range of values for the OA-risk associated protein expected when various OA severities are present or when OA is not present. A control value can be the mean fluorescence intensity for each OA-risk associated protein obtained from a parallel control sample from a subject having known OA severity, or not having OA. In some examples, the control value represents the value for a subject of the same gender, in the same age range (for example ±2 years, ±5 years or ±10 years), or combinations thereof.

To determine the severity of OA, or the likelihood that a subject will develop severe OA, the magnitude of the change in a target OA-risk associated molecule activity can be determined in a subject. For example, if the OA-risk associated molecule is one that is upregulated in response to or to cause OA (for example those proteins in Tables 10-13 noted as upregulated), severity can be determined by determining the magnitude of increased activity relative to a control (such as activity in the absence of OA), wherein a greater magnitude of increased activity indicates more severe OA (or greater likelihood that a subject will develop severe OA). For example, a subject having one or more OA risk-associated molecules whose activity is increased by at least 2-fold relative to the control, is said to have less severe OA than a subject having one or more OA risk-associated molecules whose activity is increased by at least 10-fold relative to the control. In particular examples, an increase in the activity of one or more OA risk-associated molecules by at least 4-fold, at least 5-fold, or at least 10-fold indicates that the subject has, or will likely develop, severe OA. For example, an increase in the activity by at least 4-fold, at least 5-fold, or at least 10-fold of one or more (such as at least 2, at least 3, at least 4 or at least 5) OA risk-associated molecules listed in Tables 10 and 12 noted as upregulated, indicates that the subject has severe OA. In another example, an increase in the activity by at least 4-fold, at least 5-fold, or at least 10-fold of one or more (such as at least 2, at least 3, at least 4 or at least 5) OA risk-associated molecules listed in Tables 11 and 13 noted as upregulated, indicates that the subject will likely develop severe OA.

If the OA-risk associated molecule is one that is downregulated in response to OA (for example those proteins in Tables 10-13 noted as downregulated), severity can be determined by determining the magnitude of decreased activity relative to a control (such as activity in the absence of OA), wherein a greater magnitude of decreased activity indicates more severe OA (or greater likelihood that a subject will develop severe OA). For example, a subject having one or more OA risk-associated molecules whose activity is decreased by at least 2-fold relative to the control, is said to have less severe OA than a subject having one or more OA risk-associated molecules whose activity is decreased by at least 10-fold relative to the control. In particular examples, a decrease in the activity of one or more OA risk-associated molecules by at least 4-fold, at least 5-fold, or at least 10-fold indicates that the subject has, or will likely develop, severe OA. For example, a decrease in the activity by at least 4-fold, at least 5-fold, or at least 10-fold of one or more (such as at least 2, at least 3, at least 4 or at least 5) OA risk-associated molecules listed in Tables 10 and 12 noted as downregulated, indicates that the subject has severe OA. In another example, a decrease in the activity by at least 4-fold, at least 5-fold, or at least 10-fold of one or more (such as at least 2, at least 3, at least 4 or at least 5) OA risk-associated molecules listed in Tables 11 and 13 noted as downregulated, indicates that the subject will likely develop severe OA.

Therefore, in some examples, the presence of a statistically significant difference in the magnitude of change of at least 4-fold in at least one of the OA-risk associated proteins (such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or at least 36 of the proteins) indicates that the subject has severe OA or has an increased risk of developing severe OA in the future.

In order for the mean fluorescence intensity to be considered, it is ideally at least 4-fold higher than background.

In one example, statistically significant changes in magnitude include those with a p value of ≦0.05 when compared to the value for the same OA-risk associated molecule in the absence of OA or absence of OA risk in the future.

EXAMPLE 12

Monitoring OA Progression

This example describes methods that can be used to monitor OA progression in a subject, such as a subject having OA, or a subject having no clinical symptoms of OA (such as pain, swelling, and stiffness of the affected joint) but has been shown to have an increased risk of developing OA in the future. In one example, the subject has generalized OA (for example OA of the hand and knee), as compared to OA secondary to other processes (such as trauma). The assay can be performed before or following the onset of signs and symptoms associated with OA.

A sample obtained from the subject (such as a serum sample) can be analyzed using the disclosed methods. In particular examples, the assay can be performed after confirming that the subject has OA, or is predisposed to developing OA, for example has an increased risk of developing OA in the future. In particular examples, multiple samples are obtained from the subject at different time points, such as samples obtained at least 1 month apart, at least 6 months apart, or at least 1 year apart.

A sample obtained or derived from the test subject, such as a human or veterinary subject, is manipulated as needed for the detection method used. Although this example describes preparation of a serum sample for analyzing protein expression, one skilled in the art will appreciate that other biological samples can be used (such as urine or synovial fluid), and other methods of analyzing expression can be used. Serum can be obtained, manipulated, and applied to an array (which has been blocked and washed) as described in Example 9.

The array can include antibodies that recognize four or more OA-risk associated proteins, as well as other proteins that serve as controls. In a specific example, the array includes antibodies that recognize at least interleukin-15 (IL-15), soluble vascular adhesion protein 1 (sVAP-1), metalloproteinase-7 (MMP-7), plasminogen activating inhibitor-1 (PAI-1), interleukin 1 alpha (IL-1α), IL-2, macrophage inhibitory protein (MIP)-1α, B-lymphocyte chemokine (BLC), 6-chemokine (Ckine), fibroblast growth factor (FGF)-7, granulocyte macrophage colony stimulating factor (GM-CSF), insulin-like growth factor binding protein (IGFBP)-2, neurotrophin-4 (NT4), ICAM-3, vascular endothelial (VE)-cadherin, and tissue inhibitors of metalloproteinases 1 (TIMP-1). In another specific example, the array includes antibodies that recognize at least macrophage inflammatory protein 1β (MIP-1β), macrophage inflammatory protein 1δ (MIP-1δ), urokinase-type plasminogen activator receptor (UPAR), and vascular cell adhesion molecule-1 (VCAM-1), IL-2, Eot2, IGFBP-4, ICAM-3, monokine induced by interferon γ (MIG), MMP-7, myeloid progenitor inhibitory factor 1 (MPIF-1), TGFβ receptor III (TGF-β RIII), and thymus and activation regulated chemokine (TARC), and can further include antibodies that recognize 6-Ckine.

In a specific example, the array includes antibodies that recognize at least IL-15, sVAP-1, MMP-7, PAI-1, DD5, DD6, Eot2, ICAM-1, MMP-2, P-selectin, IL-1α, IL-2, MIP-1α, BLC, 6-Ckine, FGF-7, GM-CSF, IGFBP-2, NT4, ICAM-3, VE-cadherin, and TIMP-1. In another specific example, the array includes antibodies that recognize at least MIP-1β, MIP-1δ, UPAR, VCAM-1, IL-2, Eot2, IGFBP-4, ICAM-3, MMP-7, MIG, MPIF-1, TGF-β RIII, 6-Ckine, TARC, BDNF, EGF, HCC1, leptin, and prolactin.

In yet another specific example, the array includes antibodies that recognize at least IL-15, sVAP-1, MMP-7, PAI-1, DD5, DD6, Eot2, ICAM-1, MMP-2, P-selectin, MIP-1β, MIP-1δ, UPAR, VCAM-1, BDNF, EGF, HCC1, leptin, prolactin, IL-1α, IL-2, MIP-1α, BLC, 6-Ckine, FGF-7, GM-CSF, IGFBP-2, NT4, ICAM-3, VE-cadherin, TIMP-1, IGFBP4, MIG, MPIF-1, TGF-β RIII, and TARC.

The formed complexes between the proteins in the serum and the antibodies on the array are detected, for example using RCA indirect immunoassay using the methods described in Example 9.

The arrays are scanned and the mean fluorescence intensity for each protein on the array determined. Background fluorescence intensity can be subtracted from all experimental fluorescence intensity if desired. The intensity for each protein can be compared to a control or reference value. For example, a reference fluorescence signal intensity value can be a value or range of values for the OA-risk associated protein expected when OA is present or not present. In one example, the reference value is the protein concentration for a particular OA-risk associated protein in the subject at one or more earlier time points, such as at least 1 month earlier, at least 6 months earlier, at least 1 year earlier, or at least 10 years earlier. In some examples, the control value represents the value for a subject of the same gender, in the same age range (for example ±2 years, ±5 years or ±10 years), or combinations thereof.

To monitor the progression of OA, the change in a target OA-risk associated molecule activity can be monitored over time in the same subject. For example, if the OA-risk associated molecule is one that is upregulated in response to or to cause OA (for example those proteins in Tables 10-13 noted as upregulated), further statistically significant increases in activity in the target OA-risk associated molecule indicate that the OA is worsening or progressing at a faster rate. In contrast, statistically significant decreases in activity in such a target OA-risk associated molecule indicate that the OA is improving or progression has decreased.

If the OA-risk associated molecule is one that is downregulated in response to OA (for example those proteins in Tables 10-13 noted as downregulated), further statistically significant decreases in activity in the target OA-risk associated molecule indicate that the OA is worsening or progressing at a faster rate. In contrast, statistically significant increases in activity in such a target OA-risk associated molecule indicate that the OA is improving or progression has decreased.

In one example, statistically significant increases or decreases include those with a p value of ≦0.05 when compared to the value for the same OA-risk associated molecule at one or more earlier time points in the subject. In another example, statistically significant increases or decreases include those with an increase or decrease in the magnitude of activity, respectively, when compared to the value for the same OA-risk associated molecule at one or more earlier time points in the subject. The increase in magnitude can be an increase of at least 25%, at least 50%, at least 75%, at least 100% or at least 200%. The decrease in magnitude can be a decrease of at least 25%, at least 50%, or at least 75%.

EXAMPLE 13

Arrays for Evaluating OA Risk

This example describes particular arrays that can be used to evaluate OA risk, for example to diagnose OA or to determine if a subject has an increased risk of developing OA in the future.

In one example, the array includes probes (such as an oligonucleotide or antibody) that can recognize at least one OA-risk related molecule (such as a nucleic acid or protein) that is upregulated in response to OA risk, such as one or more of IL-15, MMP-7, sVAP-1, IL-1α, IL-2, MIP-1α, BLC, 6-Ckine, FGF-7, GM-CSF, IGFBP-2, NT4, ICAM-3, TIMP-1, VE-cadherin, MIP-1β, UPAR, IGFBP-4, MIG, MPIF-1, TGF-β RIII, BDNF, HCC, and leptin, or any 1, 2, 3, 4, 5, 6, 7, 8, 9, 10, 11, 12, 13, 14, 15, 16, 17, 18, 19, 20, 21, 22, 23, or 24 of these. For example, the array can include a probe (such as an oligonucleotide or antibody) recognizes IL-15. In yet another example, the array includes probes (such as an oligonucleotide or antibody) that can recognize at least one OA-risk related molecule (such as a nucleic acid or protein) that is downregulated response to OA risk, such as one or more of PAI-1, MIP-1δ, Eot2, TARC, DD5, DD6, ICAM-1, MMP-2, P-selectin, MIP-1δ, EGF, and prolactin, or any 1, 2, 3, 4, 5, 6, 7, 8, 9, 10, 11, or 12 of these.

In a particular example, the array includes probes (such as an oligonucleotide or antibody) that can recognize at least one OA-risk related molecule (such as a nucleic acid or protein) that is upregulated in response to OA risk (such as at least one of IL-15, MMP-7, sVAP-1, IL-1α, IL-2, MIP-1α, BLC, 6-Ckine, FGF-7, GM-CSF, IGFBP-2, NT4, ICAM-3, TIMP-1, VE-cadherin, MIP-1β, UPAR, IGFBP-4, MIG, MPIF-1, TGF-β RIII, BDNF, HCC, and leptin) and at least one gene (or protein) that is downregulated in response to OA risk (such as one or more of PAI-1, MIP-1δ, Eot2, TARC, DD5, DD6, ICAM-1, MMP-2, P-selectin, MIP-1δ, EGF, and prolactin).

In a particular example, the array consists probes (such as an oligonucleotide or antibody) that can recognize IL-15, MMP-7, sVAP-1, IL-1α, IL-2, MIP-1α, BLC, 6-Ckine, FGF-7, GM-CSF, IGFBP-2, NT4, ICAM-3, TIMP-1, VE-cadherin, MIP-1β, UPAR, IGFBP-4, MIG, MPIF-1, TGF-β RIII, BDNF, HCC, and leptin PAI-1, MIP-1δ, Eot2, TARC, DD5, DD6, ICAM-1, MMP-2, P-selectin, MIP-1δ, EGF, and prolactin. However, the array can further include control probes Other exemplary probes that can be used are listed in Tables 8 and 10-13. For example, the array can consist of probes (such as an oligonucleotide or antibody) that recognize the OA-risk associated molecules listed in Table 10, 11, 12, or 13. In another example, the array can consist of probes (such as an oligonucleotide or antibody) that recognize the OA-risk associated molecules listed in all of Tables 10-13.

The OA risk-associated probes can further include one or more detectable labels, to permit detection of hybridization or specific binding signals between the probe and a target sequence.

Compilation of "loss" and "gain" of hybridization or specific binding signals will reveal the status of the individual with respect to the OA risk-associated genes listed in Tables 8 and 10-13.

EXAMPLE 14

Quantitative Spectroscopic Methods

This example describes particular quantitative spectroscopic approaches, such as SELDI, that can be used to detect differential protein activity of OA risk-related proteins (such as those listed in Tables 8 and 10-13), for example as an alternative to using an RCA microarray immunoassay.

In one example, surface-enhanced laser desorption-ionization time-of-flight (SELDI-TOF) mass spectrometry is used to detect changes in differential activity of OA risk-associated proteins, for example by using the ProteinChip™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586, all herein incorporated by reference). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as OA risk-associated proteins. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as OA-risk related proteins) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that recognize OA risk-associated proteins, such as IL-15 and sVAP-1. In one example, antibodies are immobilized onto the surface using a bacterial Fc binding support. The chromatographic surface is incubated with a sample from the subject, such as a sample that includes serum proteins. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

EXAMPLE 15

Nucleic Acid-Based Analysis

The OA risk-related nucleic acid molecules disclose herein (such as those disclosed in Tables 8 and 10-13) can be used in evaluating OA risk, for example for determining whether a subject has OA, determining the risk of a subject for developing OA in the future, determining the severity of OA, monitoring the progression of OA in a subject, and determining a treatment regimen for a subject having OA. For such procedures, a biological sample of the subject can be assayed for an increase or decrease in the activity (such as the expression) of OA risk-related nucleic acid molecules, such as those listed in Tables 8 and 10-13. Suitable biological samples include samples containing genomic DNA or RNA (including mRNA) obtained from cells of a subject, such as those present in peripheral blood, urine, saliva, tissue biopsy, surgical specimen, and synovial fluid.

RNA can be isolated from cells as follows. Total RNA (5-15 μg) can be extracted from cells separated from whole blood using the RNeasy Mini Kit (Qiagen Cat. #75162, Valencia, Calif.), as per the manufacturer's protocol. Briefly, harvested cells are diluted with PBS and centrifuged for 10 minutes at 4000 rpm. The resulting supernatant is discarded and the pellet homogenized and RNA collected. RNA can be labeled using methods known in the art. In one example, RNA is biotin-labeled and cleaned according to Affymetrix guidelines for Human Genome arrays, for example using the Enzo BioArray HighYield RNA Transcript Labeling Kit3 (Affymetrix, P/N 900182) to generate a labeled cRNA target. To ensure the quality of the initial isolated total RNA, DNase can be used to remove contaminant DNA from the sample.

The detection in the biological sample of increased or decreased expression in four or more OA risk-related nucleic acid molecules, such any combination of four or more molecules listed in Tables 8 and 10-13 (such as a combination that includes IL-15 or sVAP-1), can be achieved by methods known in the art. In some examples, expression is determined for at least IL-15, MMP-7, sVAP-1, PAI-1, or for at least MIP-1β, MIP-1δ, UPAR, VCAM-1, 6-Ckine, ICAM-3, and TGFβ-RIII.

Increased or decreased expression of an OA risk-related molecule also can be detected by measuring the cellular level of OA risk-related nucleic acid molecule-specific mRNA. mRNA can be measured using techniques well known in the art, including for instance Northern analysis, RT-PCR and mRNA in situ hybridization. Details of mRNA analysis procedures can be found, for instance, in provided examples and in Sambrook et al. (ed.), *Molecular Cloning: A Laboratory Manual,* 2nd ed., vol. 1-3, Cold Spring Harbor Laboratory Press, Cold Spring Harbor, N.Y., 1989.

Oligonucleotides specific to OA risk-related sequences can be chemically synthesized using commercially available machines. These oligonucleotides can then be labeled, for example with radioactive isotopes (such as $^{32}P$) or with non-radioactive labels such as biotin (Ward and Langer et al., *Proc. Natl. Acad. Sci. USA* 78:6633-57, 1981) or a fluorophore, and hybridized to individual DNA samples immobilized on membranes or other solid supports by dot-blot or transfer from gels after electrophoresis. These specific sequences are visualized, for example by methods such as autoradiography or fluorometric (Landegren et al., *Science* 242:229-37, 1989) or colorimetric reactions (Gebeyehu et al., *Nucleic Acids Res.* 15:4513-34, 1987).

Nucleic acid molecules isolated from cells can be amplified using routine methods to form nucleic acid amplification products. These nucleic acid amplification products can then be contacted with an oligonucleotide probe that will hybridize under stringent conditions with an OA risk-related nucleic acid. The nucleic acid amplification products which hybridize with the probe are then detected and quantified. The sequence of the oligonucleotide probe can bind specifically to a nucleic acid molecule that encodes an OA risk-related molecule listed in Tables 8 and 10-13.

EXAMPLE 16

Protein-Based Analysis

This example describes methods that can be used to detect changes in activity (such as expression or biological activity) of OA risk-related proteins. OA risk-related protein sequences can be used in methods of evaluating OA risk, for example for determining whether a subject has OA, determining the severity of OA in a subject having OA, monitoring OA progression in a subject, determining whether a subject has an increased risk of developing OA in the future, and determining a treatment regimen for a subject who has or is at increased risk for developing OA. For such procedures, a biological sample of the subject is assayed for a change in activity (such as an increase or decrease) of any combination of at least four OA risk-related proteins, such as any combination of that includes at least IL-15 or sVAP in combination with at least two of those listed in Tables 8 and 10-13, or any combination that includes two or more of MIP-1β, MIP-1δ, UPAR, VCAM-1, 6-Ckine, ICAM-3, and TGFβ-RIII in combination with at least two of those listed in Tables 8 and 10-13. In some examples, the amount of OA risk-associated is determined for at least MIP-1β, MIP-1δ, UPAR, VCAM-1, 6-Ckine, ICAM-3, and TGFβ-RIII. In some examples, the amount of OA risk-associated is determined for at least IL-15, sVAP, MMP-7 and PAI-1.

Suitable biological samples include those that contain proteins such as those present in serum (or other blood fraction) or synovial fluid. A change in the amount of four or more OA risk-related proteins in a subject, such as an increase or decrease in four or more OA-related proteins listed in Tables 8 and 10-13, can indicate that the subject has OA or is at risk for developing OA in the future.

The determination of increased or decreased OA risk-related protein levels, in comparison to such expression in a normal subject (such as a subject who has no OA or no risk of OA), is an alternative or supplemental approach to the direct determination of the expression level of OA risk-related nucleic acid sequences by the methods outlined above. The availability of antibodies specific to OA risk-related proteins facilitate the detection and quantitation of OA risk-related proteins by one of a number of immunoassay methods that are well known in the art, such as those presented in Harlow and Lane (*Antibodies, A Laboratory Manual*, CSHL, New York, 1988). Methods of constructing such antibodies are known in the art.

Any standard immunoassay format (such as ELISA, Western blot, or RIA assay) can be used to measure OA risk-related protein levels. A comparison to wild-type (normal) OA risk-related protein levels and an increase or decrease in OA risk-related peptide levels (such as an increase in any combination of at least 4 proteins listed in Tables 8 and 10-13 or a decrease in any combination of at least 4 proteins listed in Tables 8 and 10-13) is indicative of OA or risk of developing OA in the future. Immunohistochemical techniques can also be utilized for OA risk-related protein detection and quantification. For example, a tissue sample can be obtained from a subject, and a section stained for the presence of an OA risk-related protein using the appropriate OA risk-related protein specific binding agents and any standard detection system (such as one that includes a secondary antibody conjugated to horseradish peroxidase). General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

In a specific example an RCA protein array is used to determine if there is differential expression of four or more OA risk-related proteins in a sample obtained from the subject. Such methods are described in the examples above. Briefly, the sample containing proteins is applied to an array containing antibodies that recognize four or more OA risk-related peptides, such as four or more of those listed in Tables 8 and 10-13, under conditions sufficient for the proteins to specifically bind to the appropriate antibody. A biotinylated antibody is then added under conditions sufficient to bind to the captured proteins, thereby generating highly specific immune complexes. A universal anti-biotin antibody conjugated to primer oligonucleotides that are pre-annealed to a complementary circular oligonucleotide is then added under conditions sufficient to bind to the biotinylated antibody. The universal antibody is amplified using RCA, using DNA polymerase that extends the 3' ends of primers around the circles, resulting in long, single stranded RCA products that remain attached to the complex. The RCA products can be detected by hybridization with a labeled (such as a fluorophore, for example Cy-3, Cy-5, or FITC) complementary oligonucleotides.

For the purposes of quantitating OA risk-related proteins, a biological sample of the subject that includes cellular proteins can be used. Quantitation of an OA risk-related protein can be achieved by immunoassay and the amount compared to levels of the protein found in cells from a subject who has no OA or risk of OA in the future. A significant increase in the amount of four or more OA risk-related proteins in the cells of a subject compared to the amount of the same OA risk-related protein found in normal human cells is usually at least 4-fold or greater difference. Substantial overexpression of four or more OA risk-related proteins (such as those listed in Table 8 and 10-13) can be indicative of OA risk. Similarly, a significant decrease in the amount of four or more OA risk-related proteins in the cells of a subject compared to the amount of the same OA risk-related protein found in normal human cells is usually at least 4-fold or greater difference. Substantial underexpression of four or more OA risk-related proteins (such as those listed in Tables 8 and 10-13) can be indicative of increased risk of developing OA in the future.

An alternative method of evaluating OA risk is to quantitate the level of four or more OA risk-related proteins in a subject, for instance in the cells of the subject. This diagnostic tool is useful for detecting reduced or increased levels of OA risk-related proteins, for instance, though specific techniques can be used to detect changes in the size of proteins, for instance. Localization or coordinated expression (temporally or spatially) of OA risk-related proteins can also be examined using well known techniques.

EXAMPLE 17

Expression Profiles (Fingerprints)

With the disclosure of many OA risk-related molecules (as represented for instance by those listed in Tables 8 and 10-13), expression profiles that provide information on evaluating OA risk, for example for determining whether a subject has OA determining the severity of the OA, monitoring the progression of OA, determining whether a subject has an increased risk of developing OA in the future, and determining a treatment regimen for a subject who has or is at risk for developing OA, are now enabled.

OA risk-related expression profiles include the distinct and identifiable pattern of expression (or level) of sets of OA risk-related genes or proteins, for instance a pattern of increased and decreased expression of a defined set of genes or proteins, or molecules that can be correlated to such molecules, such as mRNA levels or protein levels or activities. The set of molecules in a particular profile can include any combination of at least four of the molecules listed in any of Tables 8 and 10-13. In one example, the molecules included in the profile include at least IL-15, MMP-7, sVAP-1, and PAI-1, for example in combination with at least two of DD5, DD6, Eot2, ICAM-1, MMP-2, and P-selectin, or in combination with at least two of IL-1α, IL-2, MIP-1α, BLC, 6-Ckine, FGF-7, GM-CSF, IGFBP-2, T4, ICAM-3, VE-cadherin, and TIMP-1. In another example, the molecules included in the profile include at least MIP-1β, MIP-1δ, UPAR, VCAM-1, 6-Ckine, ICAM-3, and TGFβ-RIII, for example in combination with at least two of BDNF, EGF, HCC1, leptin, MMP-7, and prolactin, or in combination with at least two of IL-2, IGFBP-4, MIG, MMP-7, MPIF-1, Eot2 and TARC.

Particular profiles can be specific for a particular stage or age of normal tissue (such as serum or synovial fluid). Thus, expression profiles can be established for a pre-OA sample (such as normal tissue not subjected to conditions that mimic or induce OA) or cells isolated from OA tissue. Each of these profiles includes information on the expression level of at least four or more genes or proteins whose expression is altered to cause or as a result of OA. Such information can include relative as well as absolute expression levels of specific genes or proteins. Likewise, the value measured can be the relative or absolute level of protein activity, which can be correlated with a "gene expression level." Results from the expression profiles of an individual subject can be viewed in the context of a test sample compared to a baseline or control sample fingerprint/profile.

The levels of molecules that make up a expression profile can be measured in any of various known ways, which may be specific for the type of molecule being measured. Thus, nucleic acid levels (such as direct gene expression levels, such as the level of mRNA expression) can be measured using specific nucleic acid hybridization reactions. Protein levels can be measured using standard protein assays, using immunologic-based assays (such as ELISAs and protein arrays, such as an RCA protein array), or using activity assays. Examples for measuring nucleic acid and protein levels are provided herein; other methods are well known to those of ordinary skill in the art.

Examples of OA risk expression profiles can be in array format, such as a nucleotide or protein array or microarray. The use of arrays to determine the presence or level of a collection of biological macromolecules is now well known. In array-based measurement methods, an array can be contacted with polynucleotides (in the case of a nucleic acid-based array) or proteins (in the case of a protein-based array) from a sample from a subject. The amount or position of binding of the subject's nucleic acid molecules or proteins then can be determined, for instance to produce an expression profile for that subject. Such gene expression profile can be compared to another expression profile, for instance a control expression profile from a subject known to have OA, or known to not have OA. Such a method could be used to determine whether a subject has OA or determine the severity of the OA. In addition, the subject's expression profile can be correlated with one or more appropriate treatments, which can be correlated with a control (or set of control) expression profiles for levels of OA, for instance.

EXAMPLE 18

Rapid Screening Assays

Prior to performing any assays to identify agents that alter the activity (such as the amount of expression) of an OA risk-related molecule, rapid screening assays can be used to screen a large number of agents to determine if they bind to an OA risk-related protein.

Rapid screening assays for detecting binding to HIV proteins have been disclosed, for example in U.S. Pat. No. 5,230, 998, which is incorporated by reference. Briefly, an OA-related protein (such as one or more of those listed in Tables 8 and 10-13, for example IL-15, MMP-7, sVAP-1, or VCAM-1) is incubated with a first antibody capable of binding to the protein, and incubated with one or more test agents. Excess unbound first antibody is washed and removed, and antibody bound to the OA risk-related protein is detected by adding a second labeled antibody which binds the first antibody. Excess unbound second antibody is then removed, and the amount of detectable label is quantitated. The effect of the binding is then determined in percentages by the formula: (quantity of the label in the absence of the test agent)−(quantity of the label in the presence of the test agent/quantity of the label in the absence of the test agent)×100.

Agents that have a high binding affinity to the OA risk-related protein can then be used in other assays more specifically designed to determine the activity (such as the expression) of an OA risk-related molecule in the presence of the agent (such as the methods described in the Examples below).

EXAMPLE 19

In Vitro Screening Assay

This example describes particular in vitro methods that can be used to screen test agents for their ability to alter the activity of an OA-related molecule. However, the disclosure is not limited to these particular methods. One skilled in the art will appreciate that other in vitro assays could be used.

As disclosed in the Examples above, activity of the disclosed OA-related molecules (such as those listed in Tables 8 and 10-13) is increased or decreased as a result of or to causes OA. Therefore, screening assays can be used to identify and analyze agents that normalize such activity (such as decrease activity of a nucleic acid or protein that is increased in response to or to cause OA, increase activity of a nucleic acid or protein that is decreased in response to or to cause OA, or combinations thereof), or further enhance the change in activity (such as further decrease activity of a nucleic acid or protein that is decreased in response to or to cause OA, or further increase activity of a nucleic acid or protein that is increased in response to or to cause OA). For example, it may be desirable to further enhance the change in activity if such a change provides a beneficial effect to the subject or it may be desirable to neutralize the change in activity if such a change provides a harmful effect (such as inflammation) to the subject.

Agents identified via the disclosed assays can be useful, for example, in decreasing one or more symptoms associated with OA, such as a decrease of at least about 10%, at least about 20%, at least about 50%, or even at least about 90%. Once identified, test agents found to alter the activity of an OA risk-related molecule can be formulated in therapeutic products (or even prophylactic products) in pharmaceutically acceptable formulations, and used to treat a subject who has OA or has an increased risk of developing OA in the future.

Cells (such as at least 10,000 cells, for example $1 \times 10^4$-$1 \times 10^6$ cells) that provide a model what happens in vivo in a subject having OA are cultured under hypoxic conditions. For example, chondrocytes can be cultured at 37° C. in hypoxic conditions using the methods described in Yudoh et al. (*Arthritis Res Ther.* 7(2):R380-91, 2005). Briefly, chondrocytes can be obtained commercially or from cartilage, and cultured at 5% $CO_2$ in the presence of $H_2O_2$ at a concentration of 0.1-200.0 μmol/l, such as 0.1 μmol/l. Chondrocytes are incubated under the hypoxic conditions for at least 1 hour, such as at least 4 hours or at least 24 hours. The test agent is added to the cells before, during, or after culturing the cells in $H_2O_2$. In one example, the agent is incubated with the cells at least 1 hour, at least 2 hours, at least 6 hours, or at least 24 hours after culturing the cells in the hypoxic conditions.

In another example, cells from a subject having osteoarthritis are isolated and cultured using methods known in the art (for example see Yudoh et al., *Arthritis Res Ther.* 7(2): R380-91, 2005). Briefly, chondrocytes are isolated from macroscopically intact zones of cartilage as follows. Cartilage tissue is cut into small pieces, washed in phosphate-buffered saline (PBS), and digested in Dulbecco's modified Eagle's medium (DMEM; Sigma, St. Louis, Mo., USA) containing 1.5 mg/ml collagenase B (Sigma) at 37° C. overnight on a shaking platform. Cells are centrifuged, washed with PBS, and plated with fresh DMEM. The resulting chondrocytes are cultured in DMEM supplemented with 10% heat-inactivated foetal calf serum, 2 mmol/l 1-glutamine, 25 mmol/l HEPES, and 100 units/ml penicillin and streptomycin at 37° C. in a humidified 5% CO2 atmosphere. To confirm chondrocyte phenotype is maintained during the passage, cell morphology and potential to produce proteoglycan can be monitored. The test agent is added to the cells for the desired amount of time.

The one or more test agents are incubated with the cells under conditions sufficient for the test agent to have the desired effect on the cell, for example to alter (such as normalize) the activity of an OA risk-related molecule. In one example, the agent is incubated with the cells for at least 1 hour, at least 2 hours, at least 6 hours, at least 24 hours, or at least 1 week.

To determine the effect of the test agents on the activity of one or more OA risk-related molecules, RNA can be isolated from the cells and labeled using methods known in the art. The labeled RNA can be exposed to an array containing one or more nucleic acid molecules (such as a primer or probe) that can specifically hybridize to one or more OA risk-related genes, such at least 1, at least 2, or at least 3 of those listed in Tables 8 and 10-13, for example one or more of IL-15, MMP-7, sVAP-1, MIP-1δ, MIP-1β, UPAR, V-CAM-1, 6-Ckine, ICAM-3, TGB-β RIII, or PAI-1. By detecting hybridization complexes, whether a change in nucleic acid activity in the target OA risk-associated molecule was effected by the test agent can be determined, for example by comparing to a control in the absence of the test agent or to a reference value.

Alternatively, to determine the effect of the test agents on the activity of one or more OA risk-related molecules, proteins from the cells can be analyzed. The proteins (such as a cell lysate or isolated proteins) can be analyzed to detect differential activity of one or more OA risk-related proteins, such at least 1, at least 2, or at least 3 of those listed in Tables 8 and 10-13, for example one or more of IL-15, MMP-7, sVAP-1, MIP-1δ, MIP-1β, UPAR, V-CAM-1, 6-Ckine, ICAM-3, TGB-β RIII, or PAI-1. In one example, the methods described in Example 9 are used. By detecting the proteins, whether a change in protein activity in the target OA risk-associated molecule was effected by the test agent can be determined, for example by comparing to a control in the absence of the test agent or to a reference value.

EXAMPLE 20

In vivo Screening Assay

This example describes particular in vivo methods that can be used to screen test agents for their ability to alter the activity of an OA risk-related molecule. However, the disclosure is not limited to these particular methods. One skilled in the art will appreciate that other in vivo assays could be used (such as other mammals or other means of inducing OA in the test subject).

A mammal that spontaneously develops OA (such as a STR/1N mouse), or a mammal exposed to conditions that induce OA, are used. In a particular example, OA is induced in a rabbit by partial medial meniscectomy under anesthesia (for example an intramuscular injection of ketamine (15 mg/kg body wt) and xylazine (1.5-2 mg/kg body wt)). The rabbit is anesthetized and the skin incised anterior to the medial collateral ligament. After the joint capsule is opened vertically, the anterior insertional ligament of the medial meniscus is transected, and the anterior horn and medial part of the meniscus dissected free from its capsular attachment and from the medial collateral ligament. After the posterior insertional ligament is dissected by means of incision of the posterior capsule, the medial meniscus is removed. After joint irrigation with normal saline, joint capsule and skin are closed with single sutures.

Simultaneous to inducing OA, or at a time before or after, one or more test agents are administered to the subject under conditions sufficient for the test agent to have the desired effect on the subject. Any appropriate method of administration can be used, such as intravenous, intramuscular, transdermal, or direct injection into the affected joint. In one example, the test agent is administered at least 12 hours after the partial medial meniscectomy, such as at least 24 hours, at least 2 days, at least 3 days, at least 7 days, at least 10 days, at least 2 weeks, or at least 1 month after the meniscectomy.

The one or more test agents are incubated in the test mammal under conditions sufficient for the test agent to have the desired effect, for example to alter (such as normalize) the activity of an OA risk-related molecule. In one example, multiple doses of the one or more test agents are administered, for example daily, weekly, or monthly, for example over the course of at least 2 weeks, at least 1 month, or at least 3 months.

The effect of the test agents on the activity of one or more OA risk-related molecules can be determined using methods described herein. For example, serum can be isolated from the mammal following exposure to the test agent, and differential activity of one or more OA risk-related molecules determined, for example using the methods described in Example 9. In another example, RNA isolated from a biological sample of the mammal can be analyzed to determine the activity of one or more OA risk-related molecules, for example using the methods described in Example 15. By detecting the OA risk-associated molecule, whether a change in activity in the target OA risk-associated molecule was effected by the test agent can be determined, for example by comparing to a control in the absence of the test agent or to a reference value.

In yet another example, the animal is examined for other clinical indications of OA, such as swelling of the joint, for example by examining the affected joint with an x-ray. A decrease in the development of symptoms associated with OA in the presence of the test agent provides evidence that the test agent is a therapeutic agent that can be used to decrease or even inhibit OA in a subject.

EXAMPLE 21

Assays for Determining Effective Dose and Effect on Osteoarthritis

This example describes methods that can be used to further evaluate test agents that alter the activity of an OA risk-related molecule, such as those identified using the methods described in Examples 19 and 20. For example, effective doses of the test agents, and the ability of the agent to treat OA can be determined in vitro or in vivo.

Cell-Based Assays

Cells (such as 20,000 to 500,000 chondrocyte cells) are exposed to conditions that mimic OA, such as hypoxic conditions, and the incubation continued for at least 12 hours (such as at least 24 hours or at least 48 hours). The test agent can be applied to the cells before, during, or after mimicking OA. Alternatively, chondrocytes from an OA subject are isolated (such as by using the methods described in Example 19) and the test agent incubated with the cells in culture.

In some examples, several different doses of the potential therapeutic agent are cultured with the cells, to identify optimal dose ranges. For example, milligram, microgram, and nanogram concentrations can be used. Subsequently, assays are conducted to determine the activity of one or more OA risk-related molecules, such as an assay to measure an amount of OA risk-related protein or an amount of OA risk-related nucleic acid expression (for example, see the examples above).

Animal Model Assays

The ability of an agent, such as those identified using the methods provide above, to treat OA, can be assessed in animal models. Several methods of inducing OA in a mammal are known, and particular examples are provided herein. Mammals of any species, including, but not limited to, mice, rats, rabbits, dogs, guinea pigs, pigs, micro-pigs, goats, and non-human primates, such as rhesus macaques, can be used to generate an animal model of OA. Such animal models can also be used to test agents for an ability to ameliorate symptoms associated with OA. In addition, such animal models can be used to determine the LD50 and the ED50 in animal subjects, and such data can be used to determine the in vivo efficacy of potential agents.

An animal that spontaneously develops OA is used, or alternatively, OA is induced in the mammal (see Example 20), and one or more test agents identified in the examples above administered. The amount of test agent administered can be determined by skilled practitioners. In some examples, several different doses of the potential therapeutic agent can be administered to different test subjects, to identify optimal dose ranges. The therapeutic agent can be administered before, during, or after inducing OA. Subsequent to administering the one or more test agents, animals are observed for one or more symptoms associated with OA. A decrease in the development of symptoms associated with OA in the presence of the test agent provides evidence that the test agent is a therapeutic agent that can be used to decrease or even inhibit OA in a subject.

In view of the many possible embodiments to which the principles of our disclosure may be applied, it should be recognized that the illustrated embodiments are only examples and should not be taken as a limitation on the scope of the disclosure. Rather, the scope of the disclosure is defined by the following claims. We therefore claim as our invention all that comes within the scope and spirit of these claims.

We claim:

1. A method of evaluating osteoarthritis (OA) risk in a human subject comprising:
   detecting expression of OA risk-related proteins in a serum sample of the subject, wherein the OA risk-related proteins comprise interleukin-15 (IL-15), matrix metalloproteinase-7 (MMP-7), plasminogen activating inhibitor-1 (PAI-1), and soluble vascular adhesion protein 1 (sVAP-1), and
   comparing expression of the OA risk-related proteins in the subject sample to expression of the OA risk-related proteins in a normal control serum sample,
   wherein detecting an upregulation of at least IL-15, MMP-7 and sVAP-1 and downregulation of at least PAI-1 in the subject sample as compared to the normal sample indicates that the subject has an increased OA risk.

2. The method of claim 1, wherein the OA risk-related proteins further comprise at least four, at least 10, at least 13, at least 16 or at least 20 proteins listed in any of Tables 8 and 10-13.

3. The method of claim 1, wherein the OA risk-related proteins further comprise D-dimer 5 (DD5), DD6, eotaxin 2 (Eot2), intercellular adhesion molecule-1 (ICAM-1), MMP-2, and P-selectin, wherein the presence of downregulation of PAI-1, DD5, DD6, Eot2, ICAM-1, MMP-2, and P-selectin and the presence of upregulation of IL-15, MMP-7 and sVAP-1 indicates that the subject has an increased risk of developing OA in the future.

4. The method of claim 1, wherein the OA risk-related proteins further comprise interleukin 1 alpha (IL-1α), IL-2, macrophage inhibitory protein (MIP)-1α, B-lymphocyte chemokine (BLC), 6-chemokine (Ckine), fibroblast growth factor (FGF)-7, granulocyte macrophage colony stimulating factor (GM-CSF), insulin-like growth factor binding protein (IGFBP)-2, neurotrophin-4 (NT4), ICAM-3, vascular endothelial (VE)-cadherin, and tissue inhibitors of metalloproteinases 1 (TIMP-1), wherein the presence of downregulation of PAI-1, and the presence of upregulation of IL-15, MMP-7, sVAP-1, IL-1α, IL-2, MIP-1α, BLC, 6-Ckine, FGF-7, GM-CSF, IGFBP-2, NT4, ICAM-3, VE-cadherin, and TIMP-1, indicates that the subject has OA.

5. The method of claim 1, wherein the OA risk-related proteins further comprise macrophage inflammatory protein 1β (MIP-1β), macrophage inflammatory protein 1δ (MIP-1δ), urokinase-type plasminogen activator receptor (UPAR), and vascular cell adhesion molecule-1 (VCAM-1), wherein the presence of upregulation of IL-15, sVAP-1, UPAR, VCAM-1, and MIP-1β, and the downregulation of PAI-1 indicates that the subject has an increased OA risk.

6. The method of claim 5, wherein the OA risk-related proteins further comprise brain-derived neurotrophic factor (BDNF), epidermal growth factor (EGF), hemofiltrate CC chemokine 1 (HCC1), leptin, and prolactin, wherein the presence of upregulation of IL-15, sVAP-1, MIP-1α, MIP-1β, HCC1, leptin, MMP-7, UPAR, hVCAM-1, and BDNF, and the downregulation of PAI-1, EGF and prolactin indicates that the subject is at risk for developing OA in the future.

7. The method of claim 5, wherein the OA risk-related proteins further comprise IL-2, Eot2, IGFBP-4, ICAM-3, monokine induced by interferon γ (MIG) myeloid progenitor inhibitory factor 1 (MPIF-1), thymus and activation regulated chemokine (TARC), 6-Ckine, and TGFβ receptor III (TGF-β RIII), wherein the presence of upregulation of IL-15, sVAP-1, TGF-β RIII, IL-2, IGFBP-4, ICAM-3, MIG, MMP-7, MPIF-1, UPAR, VCAM-1, 6-Ckine, MIP-1α, and MIP-1β, and the downregulation of PAI-1, Eot2 and TARC, indicates that the subject has OA.

8. The method of claim 1, wherein the presence of upregulation in any combination of at least 10 OA risk-related proteins listed in Tables 10-11 as upregulated, indicates that the subject has OA.

9. The method of claim 1, wherein the presence of downregulation in any combination of at least 6 OA risk-related proteins listed in Tables 12-13 as down-regulated, indicates that the subject has an increased risk of developing OA in the future.

10. The method of claim 1, further comprising administering to the subject a treatment to avoid or reduce OA disease if the protein activity indicates that the subject has increased OA risk.

11. The method of claim 1, wherein the expression of the OA risk-related proteins in the normal control serum sample is represented by a reference value comprising a level of expression for each of the OA risk-related proteins in an absence of OA risk or a range of expression for each of the OA risk-related proteins in subjects of the same gender and in the same age range as the subject.

12. The method of claim 1 wherein the method is a method of determining the progression of OA, wherein detecting expression of the OA risk-related proteins comprises:
comparing a first and a second expression level of the OA-risk related proteins in the subject determined at a first and a second time point, wherein a statistically significant difference with a p value $\geq 0.05$ between the first and the second expression level of the OA-risk related proteins reflects the progression of OA in the subject.

13. The method of claim 1, wherein detecting expression comprises quantitating an amount of the OA risk-related proteins.

14. The method of claim 13, wherein detectiong expression of OA risk-related proteins comprises:
measuring a quantity of OA risk-related proteins in the subject sample, wherein an increase in the quantity of the OA risk-related proteins in the subject sample relative to a quantity of the OA risk-related proteins in the normal sample is increased expression in those OA risk-related proteins and a decrease in the quantity of the OA risk-related proteins in the subject sample relative to a quantity of the OA risk-related proteins in the normal sample is decreased expression in those OA risk-related proteins.

15. The method of claim 14, wherein a statistically significant difference with a p value $\geq 0.05$ between the quantity of the OA-risk related protein in the subject sample and the normal sample or an at least four-fold difference between the quantity of the OA-risk related protein in the subject sample and the normal sample, indicates that there is differential expression in the OA-risk related protein.

16. The method of claim 1, wherein the proteins are obtained from the serum, and wherein the proteins are incubated under conditions sufficient for the proteins to bind to antibodies that detect the OA risk-related proteins.

17. The method of claim 16, wherein incubating the proteins under conditions sufficient for the proteins to bind to antibodies comprises:
incubating the proteins with the antibodies for a time sufficient to allow specific binding between the proteins and antibodies, thereby forming protein:antibody complexes; and
analyzing the protein:antibody complexes to determine if expression of the proteins was altered.

18. The method of claim 17, wherein analyzing the protein:antibody complexes includes detecting and quantifying the complexes.

19. The method of claim 16, wherein the antibodies specifically bind to any combination of at least four proteins listed in Tables 8 and 10-13.

20. The method of claim 1, wherein the normal sample comprises a serum sample from a subject not having OA risk.

21. The method of claim 1, wherein evaluating OA risk comprises determining whether the subject has OA, determining whether the subject has an increased OA disease risk, determining the progression of OA in the subject, or determining the severity of OA in the subject.

22. The method of claim 10, wherein the treatment comprises an anti-inflammatory agent.

23. The method of claim 1, wherein detecting expression of OA risk-related proteins comprises quantitatively or qualitatively analyzing the proteins.

24. A method of evaluating OA risk in a human subject, comprising:
incubating proteins obtained from serum of the subject with an array comprising antibodies complementary to all 36 OA risk-related proteins listed in Tables 10-13 for a time sufficient to allow specific binding between the proteins and antibodies, thereby forming protein:antibody complexes; and
analyzing the protein:antibody complexes to determine an amount of each of the proteins present in the serum; and
comparing the amount of each of the proteins in the serum to a reference value, wherein the reference value is an amount of each of the proteins in the absence of OA risk, and wherein the presence of an at least four-fold increase of at least IL-15, MMP-7 and sVAP-1 and an at least four-fold decrease of at least PAI-1 in the serum as compared to the reference value indicates that the subject has increased OA risk.

25. The method of claim 24, wherein analyzing the protein:antibody complexes comprises detecting the protein:antibody complex using rolling circle amplification.

* * * * *

UNITED STATES PATENT AND TRADEMARK OFFICE
CERTIFICATE OF CORRECTION

PATENT NO. : 7,662,573 B2
APPLICATION NO. : 11/573711
DATED : February 16, 2010
INVENTOR(S) : Ling et al.

It is certified that error appears in the above-identified patent and that said Letters Patent is hereby corrected as shown below:

On the Title Page:

Other Publications, page 1, column 2, "Kurhijärvi *et al.*" should be --Kurkijärvi *et al.*--.

Other Publications, page 2, column 2, in the Oleksyszyn and Augustine reference, "Stiumulated" should be --Stimulated--.

In the Figures:

Fig. 4, "BNDF" should be --BDNF--.

Fig. 5, "-DD6" should be --DD6--.

Fig. 5, "s-VAP-1" should be --sVAP-1--.

Fig. 5, "MIP-α" should be --MIP-1α--.

Fig. 7A, "VAP-1" should be --sVAP-1--.

In the Specification:

Column 3, line 29, "molecule" should be --molecules--.

Column 4, line 32, "(CKine)" should be --(6-CKine)--.

Column 4, line 43, "MMP-1β" should be --MIP-1β--.

Column 5, line 21, "2 o more" should be --2 or more--.

Column 5, line 56, "at least 34" should be --at least 34)--.

Signed and Sealed this

Thirteenth Day of July, 2010

David J. Kappos
*Director of the United States Patent and Trademark Office*

Column 5, line 63, "HCC" should be --HCC1--.

Column 5, line 66, "EoT2" should be --Eot2--.

Column 6, line 4, "HCC" should be --HCC1--.

Column 6, line 7, "EoT2" should be deleted.

Column 6, line 11, "of at least more two" should be --of at least two--.

Column 6, line 25, "of at least more two" should be --of at least two--.

Column 6, line 26, "an decrease" should be --a decrease--.

Column 6, line 49, "molecules" should be --molecule--.

Column 6, lines 54-55, "differentially activity" should be --differential activity--.

Column 10, line 46, "metallo proteinases" should be --metalloproteinases--.

Column 11, lines 38-39, "at least 35, or at least of the sequences" should be --or at least 35 of the sequences--.

Column 12, line 4, "immunoelectrophorectic" should be --immunoelectrophoretic--.

Column 12, line 16, "osteoartritis" should be --osteoarthritis--.

Column 12, line 48, "complementary" should be --complementarity--.

Column 13, line 51, "such an" should be --such as an--.

Column 13, line 61, "such an" should be --such as an--.

Column 14, line 21, "at least 8, at least 8" should be --at least 8--.

Column 15, line 30, "L-15" should be --IL-15--.

Column 17, line 20, "such OA" should be --such as OA--.

Column 17, line 36, "P-selctin" should be --P-selectin--.

Column 17, line 54, "MMP-7" should be --PAI-1--.

Column 18, line 67, "2003" should be --2003)-- and "*Proteome*" should be --(*Proteome*--.

Column 19, line 27, "proteins" should be --protein--.

Column 19, line 55, "amounts a" should be --amounts of a--.

CERTIFICATE OF CORRECTION (continued)
U.S. Pat. No. 7,662,573 B2

Column 19, line 62, "amount of can be" should be --amount can be--.

Column 20, line 11, "such a" should be --such as a--.

Column 20, line 54, "such an" should be --such as an--.

Column 20, line 63, "such an" should be --such as an--.

Column 21, line 18, "human other mammal" should be --human or other mammal--.

Column 22, line 29, "BNDF" should be --BDNF--.

Column 22, line 30, "BNDF" should be --BDNF--.

Column 22, line 47, "this" should be --these--.

Column 23, line 10, "involves" should be --involve--.

Column 23, line 26, "L-15" should be --IL-15--.

Column 24, line 11, "MIP-1δ" should be --MIP-1β--.

Column 24, line 17, "MMP-1β" should be --MIP-1β--.

Column 24, line 42, "(CKine)" should be --(6-CKine)--.

Column 26, line 13, "MMP-1β" should be --MIP-1β--.

Column 26, line 15, "EoT2" should be --Eot2--.

Column 29, line 60, "PCR,)," should be --PCR),--.

Column 30, line 59, "an" should be --and--.

Column 31, line 64, "predisposition developing" should be --predisposition to developing--.

Column 32, line 9, "predisposition developing" should be --predisposition to developing--.

Column 32, line 55, "Netherlands." should be --Netherlands).--.

Column 33, line 37, "10-13, In" should be --10-13. In--.

Column 34, line 47, "Tables_" should be --Tables 8 and 10-13)--.

Column 35, line 5, "found an" should be --found in an--.

Column 35, lines 16-17, "polysulformes" should be --polysulfornes--.

CERTIFICATE OF CORRECTION (continued)

U.S. Pat. No. 7,662,573 B2

Column 35, line 19, "etyleneacrylic" should be --ethyleneacrylic--.

Column 36, lines 22-23, "such as see" should be --such as--.

Column 37, lines 47-48, "OA risk related-molecule" should be --OA risk-related molecule--.

Column 38, line 11, "activity one" should be --activity of one--.

Column 39, line 7, "1990); Cwirla" should be --1990; Cwirla--.

Column 41, line 3, "such at" should be --such as at--.

Column 41, line 7, "MIP1-δ" should be --MIP-1δ--.

Column 41, line 11, "sample)." should be --sample), are tested.--.

Column 41, line 15, "such at" should be --such as at--.

Column 41, line 21, MIP1-δ" should be --MIP-1δ--.

Column 41, line 29, "a OA-related" should be --an OA-related--.

Column 41, line 64, "control a test substance" should be --control test substance--.

Column 43, line 26, "was obtained" should be deleted.

Column 47, line 63, Table 7, "Souble" should be --Soluble--.

Column 48, line 53, "ILL" should be --μL--.

Column 50, line 38, "in" should be --is--.

Column 52, line 39, "demonstrate" should be --demonstrates--.

Column 53, line 7, "EoT2" should be --Eot2--.

Column 53, line 9, "TGF b III" should be --TGF-b RIII--.

Column 53, line 13, "uPAR" should be --UPAR--.

Column 53, line 20, "6ckine" should be --6Ckine--, and "slopes" should be --slope--.

Column 53, line 48, "values" should be --values.--.

Column 54, line 3, "in" should be --is--.

Column 55, lines 8-9, "uPAR" should be --UPAR--.

Column 55, line 16, "EOT2" should be --Eot2--.

Column 56, line 20, "a heat map plots" should be --heat map plots--.

Column 57, line 4, "(CKine)" should be --(6CKine)--.

Column 57, line 18, "PAI-I" should be --PAI-1--.

Column 57, line 55, "EoT-2" should be --Eot2--.

Column 57, line 62, "s-VAP1" should be --sVAP-1--.

Column 58, line 7, "EoT2" should be --Eot2--.

Column 58, line 8, "sVAP" should be --sVAP-1--.

Column 58, line 46, "That elevated" should be --Elevated--.

Column 58, line 47, "s-VAP" should be --sVAP-1--.

Column 59, line 1, "appreciated" should be --appreciate--.

Column 59, line 18, "OA)." should be --OA.--.

Column 59, line 66, "VAP-1" should be --sVAP-1--.

Column 61, line 38, "was" should be --that was--.

Column 62, line 3, "MMP-1δ" should be --MIP-1δ--.

Column 62, line 18, "appreciated" should be --appreciate--.

Column 62, line 36, "OA)." should be --OA.--.

Column 62, line 62, "EoT2" should be --Eot2--.

Column 63, lines 20, 25, 45, 59, and 66, "EoT2" should be --Eot2--.

Column 63, line 65, "sVAP" should be --sVAP-1--.

Column 64, line 2, "sVAP" should be --sVAP-1--.

Column 64, lines 3, 7, 11, 15 and 19, "EoT2" should be --Eot2--.

Column 64, lines 14 and 18, "sVAP" should be --sVAP-1--.

Column 64, lines 53 and 57, "HCC" should be --HCC1--.

Column 64, line 63, "was" should be --that was--.

Column 65, line 11, "MIP-1" should be --MIP-1β--.

Column 65, line 12, "MIP-18" should be --MIP-1δ--.

Column 65, lines 21, 28, and 33, "HCC" should be --HCC1--.

Column 65, line 63, "in certain example" should be --in a certain example--.

Column 66, line 31, "MIP)-1α" should be --(MIP)-1α--.

Column 66, line 32, "(Ckine)" should be --(6Ckine)--.

Column 66, line 58, "minutes 37°C" should be --minutes at 37°C--.

Column 68, line 16, "in certain example" should be --in a certain example--.

Column 70, line 44, "(Ckine)" should be --(6Ckine)--.

Column 73, line 7, "(Ckine)" should be --(6Ckine)--.

Column 74, line 39, "HCC" should be --HCC1--.

Column 74, line 42, "recognizes" should be --that recognizes--.

Column 74, line 46, "response" should be --in response--.

Column 74, lines 57 and 67, "HCC" should be --HCC1--.

Column 74, line 62, "consists probes" should be --consists of probes--.

Column 75, line 1, "MIP-1δ" should be omitted.

Column 76, line 26, "disclose" should be --disclosed--.

Column 76, line 57, "such any" should be --such as any--.

Column 77, line 48, "of that" should be --that--, and "sVAP" should be --sVAP-1--.

Column 77, lines 53 and 56, "OA risk-associated" should be --OA risk-associated proteins--.

Column 77, line 56, "sVAP" should be --sVAP-l--.

Column 78, lines 51-52, "oligonucleotides" should be --oligonucleotide--.

Column 79, line 23, "OA determining" should be --OA, determining--.

Column 79, line 41, "T4" should be --NT4--.

Column 79, line 63, "a expression" should be --an expression--.

Column 80, line 18, "Such gene" should be --Such a gene--.

Column 81, line 3, "causes" should be --cause--.

Column 81, line 29, "model what" should be --model for what--.

Column 82, lines 7 and 20, "such at" should be --such as at--.

Column 82, lines 9 and 22, "V-CAM-1" should be --VCAM-1--.

Column 82, lines 10 and 23, "TGB-β RIII" should be --TGF-β RIII--.

Column 82, lines 12 and 26, "effected" should be --affected--.

Column 83, line 19, "effected" should be --affected--.

Column 83, line 60, "provide" should be --provided--.

In the Claims:

Column 84, line 58, claim 4, "(Ckine)" should be --(6Ckine)--.

Column 85, lines 3-4, claim 5, "1δ (MIP-1δ)" should be --1α (MIP-1α)--.

Column 85, line 7, claim 5, "VCAM-1, and MIP-1β" should be --VCAM-1, MMP-7, MIP-1α and MIP-1β--.

Column 85, line 14, claim 6, "hVCAM-1" should be --VCAM-1--.

Column 85, line 19, claim 7, "(MIG) myeloid" should be --(MIG), myeloid--.

Column 85, line 33, claim 9, "down-regulated" should be --downregulated--.

Column 85, line 53, claim 12, "p value $\geq$ 0.05" should be --p value $\leq$ 0.05--.

Column 85, line 60, claim 14, "detectiong" should be --detecting--.

Column 86, line 7, claim 15, "p value $\geq$ 0.05" should be --p value $\leq$ 0.05--.

UNITED STATES PATENT AND TRADEMARK OFFICE
CERTIFICATE OF CORRECTION

PATENT NO. : 7,662,573 B2  
APPLICATION NO. : 11/573711  
DATED : February 16, 2010  
INVENTOR(S) : Ling et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 276 days.

Signed and Sealed this

Thirtieth Day of November, 2010

David J. Kappos
*Director of the United States Patent and Trademark Office*